(12) United States Patent
Reff et al.

(10) Patent No.: US 6,893,636 B2
(45) Date of Patent: May 17, 2005

(54) GAMMA-1 AND GAMMA-3 ANTI-HUMAN CD23 MONOCLONAL ANTIBODIES AND USE THEREOF AS THERAPEUTICS

(75) Inventors: Mitchell E. Reff, San Diego, CA (US); William S. Kloetzer, Carlsbad, CA (US); Takehiko Nakamura, Higashiyamato (JP)

(73) Assignee: Biogen Idec MA Inc., San Diego, CA (US)

(*) Notice: Subject to any disclaimer, the term of this patent is extended or adjusted under 35 U.S.C. 154(b) by 178 days.

(21) Appl. No.: 09/019,441

(22) Filed: Feb. 5, 1998

(65) Prior Publication Data

US 2003/0086921 A1 May 8, 2003

Related U.S. Application Data

(63) Continuation-in-part of application No. 08/803,085, filed on Feb. 20, 1997, now Pat. No. 6,011,138.

(51) Int. Cl.$^7$ ...................... A61K 39/395; C12P 21/08; C07K 16/28

(52) U.S. Cl. ................ 424/133.1; 424/143.1; 530/387.3; 530/388.22

(58) Field of Search .................. 530/387.3, 388.22, 530/388.2, 388.7, 388.1, 388.15; 424/133.1, 143.1, 152.1, 156.1, 145.1

(56) References Cited

U.S. PATENT DOCUMENTS

| | | | |
|---|---|---|---|
| 4,940,782 A | 7/1990 | Rup et al. | |
| 4,975,369 A | 12/1990 | Beavers et al. | |
| 5,348,876 A | 9/1994 | Michaelsen et al. | |
| 5,543,144 A | 8/1996 | Chang | |
| 5,585,089 A | * 12/1996 | Queen et al. | |
| 5,635,600 A | 6/1997 | Fanger et al. | |
| 5,648,260 A | 7/1997 | Winter et al. | |
| 5,648,267 A | 7/1997 | Reff | |
| 5,658,570 A | * 8/1997 | Newman et al. | |
| 5,736,137 A | 4/1998 | Anderson | |
| 5,811,524 A | 9/1998 | Brams et al. | |
| 6,001,358 A | 12/1999 | Black et al. | |
| 6,011,138 A | * 1/2000 | Reff et al. | |
| 6,136,310 A | 10/2000 | Hanna et al. | |

FOREIGN PATENT DOCUMENTS

| WO | WO 87/07302 | 12/1987 |
|---|---|---|
| WO | WO 88/06891 | 9/1988 |
| WO | WO 89/00138 | 1/1989 |
| WO | WO 92/17707 | 10/1992 |
| WO | WO 93/02108 | 2/1993 |
| WO | WO 96/12741 | * 5/1996 |
| WO | WO 96/12742 | 5/1996 |

OTHER PUBLICATIONS

Skolnick et al, Trends in Biotech 18(1):34–35, Jan. 2000.*
Abaza et al, J of Protein Chemistry 11(5): 433–444, 1992.*
Van Noort et al. International Reivew of Cytology 178: 127–205, 1998.*
The Merch manual of Diagnosis and Therapy, Seventeenth Edition, 1999, pp. 416–122.*
Ngo et al. The Protein Folding Problem and Tertiary Structure Prediction. Merz & LeGrand, Eds., Birkhauser Boston, pp. 491–495, 1994.*
Paul et al. Fundamental Immunology. 2nd Edition, Raven Press, New York, pp. 705 and 870, 1989.*
Wakai et al. Hybridoma, vol. 12, pp. 25–43, 1993.*
Saxon et al. J. Immunol. vol. 147, pp. 4000–40006, 1991.*
Boulet et al., "Inhibitory Effects of an Anti–Ige Antibody E25 on Allergen–induced Early Asthmatic Response," *Am J Respir Crit Care Med*, (1997) 155:1835–44.
Casale et al., "Use of an anti–IgE humanized monoclonal antibody in ragweed–induced allergic rhinitis," *J Allergy Clin Immunol*, (1997), 100:110–120.
Coyle et al., "Central Role of Immunoglobulin (Ig) E in the Induction of Lung Eosinophil Infiltration and T Helper 2 Cell Cytokine Production: Inhibition by a Non–anaphylactogenic Anti–IgE Antibody," *J Exp Med*, (1996), 183:1303–1310.
Fahy et al., "The Effect of an Anti–IgE Monoclonal Antibody on the Early–and Late–Phase Responses to Allergen Inhalation in Asthmatic Subjects," *Am J Respir Crit Care Med*, (1997), 155:1828–34.
Ohashi et al., "Immunotherapy Affects the Seasonal Increase in Specific IgE and Interleukin–4 in Serum of Patients with Seasonal Allergen Rhinitis," *Scan J Immunol*, (1997), 46(1):67–77.
Ohashi et al., "Serum levels of specific IgE, soluble interleukin–2 receptor, and soluble intercellular adhesion molecule–1 in seasonal allergic rhinitis," *Annals of Allergy, Asthma, and Immunol*, (1997), 79:213–220.
Ohashi et al., "Ten–Year Follow–Up Study of Allergic–Specific Immunoglobulin E and Immunoglobulin G4, Soluble Interleukin–2 Receptor, Interleukin–4, Soluble Intercellular Adhesion Molecule–1 and Soluble Vascular Cell Adhesion Molecule–1 in Serum of Patients on Immunotherapy for Perennial Allergic Rhinitis," *Scand J Immunol*, (1998), 47:167–178.

(Continued)

*Primary Examiner*—Christina Chan
*Assistant Examiner*—Phuong Huynh
(74) *Attorney, Agent, or Firm*—Pillsbury Winthrop LLP

(57) ABSTRACT

Monoclonal antibodies which specifically bind human CD23, the low affinity receptor for IgE (FceRII/CD23), and contain either a human gamma-1 or human gamma-3 constant domain, are disclosed. The antibodies are useful for modulating or inhibiting induced IgE expression. Accordingly, they have practical utility in the treatment or prophylaxis of disease conditions wherein inhibition of induced IgE production is therapeutically desirable, including allergic conditions, autoimmune diseases and inflammatory diseases.

27 Claims, 10 Drawing Sheets

OTHER PUBLICATIONS

Peebles et al., "Ragweed–specific antibodies in bronchoalveolar lavage fluids and serum before and after segmental lung challenge: IgE and IgA associated with eosinophil degranulation," *J Allergy Clin Immunol*, (1998), 101:265–273.

Pullerits et al., "An intranasal glucocorticoid inhibits the increase of specific IgE intiated during birch pollen season," *J Allergy Clin Immunol*, (1997), 100:601–605.

Ward E.S. and Ghetie V., "The effector functions of immunoglobulins: implications for therapy," 1995, *Therapeutic Immunology*, 2:77–94.

Luo et al., "Cross–linking of CD23 antigen by its natural ligand (IgE) or by anti–CD23 antibody prevents B lymphocyte proliferation and differentiation", J. Immunol., 146(7):2122–9 (1991).

Groves et al., "Production of an ovine monoclonal antibody to testosterone by an interspecies fusion", Hybridoma, vol. 6(1):71 (1987).

Robbins, Pathologic Basis of Disease, 5th Ed., ed. by Cotran et al., W.B. Saunders Co., Philadelphia, PA, 1994, pp. 197–199.

Seaver, Genetic Engineer News, 14(14): pp. 19, 21 (Aug., 1994).

Haak–Frendscho et al., "Administration of an anti–IgE antibody inhibits CD23 expression and IgE production in vivo", Immunology, 82:306 (1994).

Delespesse et al., "Human IgE–binding factors", Immunology Today 10:159, (1989).

Durum et al., "Proinflammatory Cytokines and Immunity," in Fundamental Immunology, Third Edition, Chapter 21, ed. by Paul et al., Raven Press, Ltd., New York, p. 826 (1993).

Vercelli et al., "Induction of human IgE synthesis required interleukin 4 and T/B cell interactions involving the T cell receptor/CD3 complex and MHC class II antigens", J. Exp. Med., 169:1295 (Apr. 1989).

Presta et al., "Humanization of an antibody directed against IgE", J. Immunology, 151(5):2623 (Sep. 1993).

Strike et al., "Production of human–human hybridomas secreting antibody to sheep erythrocytes after in vitro immunization", J. Immunol., 132(4): 1798 (Apr. 1984).

Cruse et al., Illustrated Dictionary of Immunology, CRC Press, Boca Raton, Fla., 1995, p. 69.

Capon et al., "Designing CD4 immunoadhesins for AIDS therapy", Nature, 337:525 (Feb. 1989).

Rector et al., "Detection and characterization of monoclonal antibodies specific to IgE receptors on human lymphocytes by flow cytometry", Immunol., 55: 481–488 (1985).

Suemura et al., "Monoclonal anti–Fc epsilon receptor antibodies with different specificities and studies on th expression of Fc epsilon receptors on human B and T cells", J. Immunol., 137: 1214–1220 (1986).

Noro et al., "Monoclonal antibody (H107) inhibiting IgE binding to Fc epsilon R(+) human lymphocytes", J. Immunol., 137: 1258–1263 (1986).

Yu et al., "Negative feedback regulation of IgE synthesis by murine CD23", Nature, 369: 753–756 (1994).

Bonnefoy et al., "Regulation of IgE synthesis by CD23/CD21 interaction", Int. Arch. Allergy Immunol., 107: 40–42 (1995).

Aubry et al., "CD21 is a ligand for CD23 and regulates IgE production," Nature, 358:505–507 (1992).

Bonnefoy et al., "Receptors for IgE", Curr. Opin. Immunol., 5: 944–949 (1993).

Grosjean et al., "CD23/CD21 interaction is required for presentation of soluble protein antigen by lymphoblastoid B cell lines to specific CD4+ T cell clones", Eur. J. Immunol., 24: 2982–2988 (1994).

Pene et al., "Interleukin 5 enhances interleukin 4–induced IgE production by normal human B cells. The role of soluble CD23 antigen", Eur J. Immunol., 18: 929–935 (1988).

Saxon et al., "Soluble CD23 containing B cell supernatants induce IgE from peripheral blood B–lymphocytes and costimulate with interleukin–4 in induction of IgE", J. Allergy Clin. Immunol., 86 (3 pt 1) 333–344 (1990).

Hassner and Saxon, "Isotype–specific human suppressor T cells for IgE synthesis activated by IgE–anti–IgE immune complexes", J. Immunol., 132: 2844 (1984).

Carroll et al., "Mouse x human heterohybridomas as fusion partners with human B cell tumors", J. Immunol. Methods 89: 61 (1986).

Boerner et al., "Production of antigen–specific human monoclonal antibodies from in vitro–primed human splenocytes", J. Immunol., 147: 86 (1991).

Bourget et al., "CD20 monoclonal antibodies decrease interleukin–4–stimulated expression of the low–affinity receptor for IgE (Fc epsilon RII/CD23) in human B cells by increasing the extent of its cleavage," Eur. J. Immunol., 25(7):1872–76 (1995).

Bonnefoy et al., "A new role for CD23 in inflammation", Immunol. Today, 17(9): 418–20 (1996).

Plater–Zyberk et al., "Marked amelioration of established collagen–induced arthritis by treatment with antibodies to CD23 in vivo" Nature Medicine, 1(8):781–785 (1995).

The Merck Manual, $16^{th}$ Edition, Berkow, R. ed., Rahway, NJ, pp. 1305–1312 and 1334–1338 (1992).

Busse et al., "Results of a Phase I, Single–dose, Dose–escalating Trial of a Primatized Anti–Cd23 Monoclonal Antibody (IDEC–152) in Patients With Allergic Asthma," J. of Allergy and Clinical Immunol., 107(2): abstract No. 354 (Feb. 2001).

Nakamura et al., "In vitro IgE inhibition in B cells by anti–CD23 monoclonal antibodies is functionally dependent on the immunoglobulin Fc domain", Intl. J. of Immunopharmacol., 22:131–41 (2000).

Bettler et al., "Binding site for IgE of the human lymphocyte low–affinity Fcε receptor (Fc εRII/CD23) is confined to the domain homologous with animal lectins", Proc. Natl. Acad. Sci., USA, 86:7118–22 (1989).

Webster's II New Riverside University Dictionary, Houghton–Mifflin Co., Boston, p. 933 (1984).

Yoshikawa et al., "Soluble FcεRII/CD23 in patients with autoimmune diseases and Epstein–Barr virus–related disorders: analysis by ELISA for soluble FcεRII/CD23", Immunomethods, 4(1):65–71 (Feb. 1994).

Muino et al., "The importance of specific IgG and IgE autoantibodies to retinal S antigen, total serum IgE, and sCD23 levels in autoimmune and infectious uveitis", J. Clin. Immunol., 19(4):215–222 (Jul. 1999).

Soh et al., "IgE and its related phenomena in bullous pemphigoid", Br. J. Dermatol., 128:371–377 (1993).

Fries et al., "Monocyte receptors for the Fc portion of IgG studies with monomeric human IgG1: normal in vitro expression of Fcγ receptors in HLA–B8/Drw3 subjects with defective Fcγ–mediated in vivo clearance", J. Immunol., 129: 1041–1049 (1982).

Kurlander and Batker et al., "The binding of human immunoglobulin G1 monomer and small, covalently cross-linked polymers of immunoglobulin G1 to human peripheral blood monocytes and polymorphonuclear leukocytes", J. Clin. Invest., 69: 1–8 (1982).

Woof, "The monocyte binding domain(s) on human immunoglobulin G", Mol. Immunol., 21:523–527 (1984).

Burton and Woof, "Human antibody effector function", *Human Antibody Effector Function*, Adv. Immunol., 51: 1–84 (1992).

Karas et al., "Characterization of the IgG–Fc receptor on human platelets", Blood, 60:1277–1282 (1982).

Van de Winkel and Anderson, "Biology of human immunoglobulin G Fc receptors", J. Leuk. Biol., 49:511–524 (1991).

Huizinga et al., "Binding characteristics of dimeric IgG subclass complexes to human neutrophils", J. Immunol., 142:2359–2364 (1989).

Bosma et al., "A severe combined immunodeficiency mutation in the mouse", Nature, 301:527 (1983).

Mosier et al., "Transfer of a functional human immune system to mice with severe combined immunodeficiency", Nature, 335:256 (1988).

Mosier et al., "Immunodeficient mice xenografted with human lymphoid cells: new models for in vivo studies of human immunobiology and infectious diseases", J Clin Immunol., 10:185–91 (1990).

Abedi et al., "Immunoglobulin production in severe combined immunodeficient (SCID) mice reconstituted with human peripheral blood mononuclear cells", Eur. J. Immunol., 22:823 (1992).

Mazingue et al., "Obtention of a human primary humoral response against schistosome protective antigens in severe combined immunodeficiency mice after the transfer of human peripheral blood mononuclear cells", Eur. J. Immunol., 21:1763 (1991).

Kilchherr et al., "Regulation of human IgE response in hu–PBL–SCID mice", Cellular Immunology, 151:241 (1993).

Spiegelberg et al., "Role of interleukin–4 in human immunoglobulin E formation in hu–PBL–SCID mice", J. Clin. Invest., 93:711 (1994).

Carballido et al., "IL–4 induces human B cell maturation and IgE synthesis in SCID–hu mice. Inhibition of ongoing IgE production by in vivo treatment with an IL–4/IL–13 receptor antagonist", J. Immunol., 155:4162 (1995).

King et al., "Expression, purification and characterization of a mouse–human chimeric antibody and chimeric Fab' fragment", Biochem. J., 281:317–23 (1992).

Queen et al., "A humanized antibody that binds to the interleukin 2 receptor", Proc. Nat. Acad. Sci. USA, 86:10029 (1989).

Love et al., "Recombinant antibodies possessing novel effector functions", Methods Enzymol., 178:515–27 (1989).

Hutzell et al., "Generation and characterization of a recombinant/chimeric B72.3 (human $\gamma_1$)", Cancer Res., 51:181 (1991).

Chiang et al., "Direct cDNA cloning of the rearranged immunoglobulin variable region", Biotechniques, 7(4):360–6 (1989).

Heinrich et al., "Characterization of a human T cell–specific chimeric antibody (CD7) with human constant and mouse variable regions", J. Immunol., 143:3589 (1989).

Hardman et al., "Generation of a recombinant mouse–human chimaeric monoclonal antibody directed against human carcinoembryonic antigen", Int. J. Cancer, 44:424 (1989).

Orlandi et al., "Cloning immunoglobulin variable domains for expression by the polymerase chain reaction", Proc. Nat. Acad. Sci. USA, 86(10):3833–7 (1989).

Norman et al., "Reversal of Acute Allograft Rejection With Monoclonal Antibody," *Transpl. Proc.*, 17:39–41 (1985).

Sarfati et al., "Elevation of IgE–binding factors in serum of patients with B cell–derived chronic lymphocytic leukemia", Blood, 71:94–98 (1988).

Saragovi et al., "Design and synthesis of a mimetic from an antibody complementarity–determining region", Science, 16;253(5021):792–5.

Bonnefoy et al., J. Immunol., 138: 2970–2978 (1987).

Flores–Romo et al., Science, 261: 1038–1046 (1993).

Sherr et al., J. Immunol., 142: 481–489 (1989).

Pene et al., Proc. Natl. Acad. Sci., USA, 85: 6880–6884 (1988).

Bonnefoy et al., Eur. J. Immunol 20: 139–144 (1990).

Sarfati et al., J. Immunol 141: 2195–2199 (1988).

Wakai et al., Hybridoma 12: 25–43 (1993).

Saxon et al., J. Immunol., 147: 4000–4006 (1991).

D'Ambrosio et al., Science, 268: 293–297 (1995).

Leconant et al., Immunol., 88: 35–39 (1996).

Aubry et al., Nature, 358: 505–507 (1992).

Nambu et al., Immunol. Lett., 44: 163–167 (1995).

Sarfati et al., Immunol., 53: 197–205 (1984).

Pene et al., J. Cell Biochem., 39: 253–269 (1989).

Sarfati et al., Immunol., 76: 662–667 (1992).

Angal et al., Mol. Immunol., 30: 105–108 (1993).

Pène et al, "Interleukin 5 enhances interleukin 4–induced IgE production of normal human B cells . . . ", Eur. J. Immunol., 18:929–935, 1988.

Sarfati et al, "In vitro synthesis of IgE by human lymphocytes", Immunol., 53:197–205 (1984).

Saxon et al, "Inhibition of human IgE production via FcεR–II stimulation results from a decrease in the mRNA for secreted . . . chains", J. Immunol., 147(11):4000–4006, 1991.

Sherr et al, "Binding the low affinity FcεR on B cells suppresses ongoing human IgE Synthesis", J. Immunol., 142(2):481,489, 1989.

Bonnefoy et al, "A new role for CD23 in inflammation", Immunol. Today, 17(9):418–420, 1996.

Bonnefoy et al, "Inhibition of human interleukin 4–induced IgE synthesis by a subset of anti–CD23/FcεRII monoclonal antibodies", Eur. J. Immunol., 20:139–144, 1990.

Angal et al, "A single amino acid substitution abolishes the heterogeneity of chimeric mouse/ human (IgG4) Antibody", Mol. Immunol. 30(1):105–108, 1993.

Urlaub et al, "Effect of gamma rays at the dihydrofolate reductase locus: deletions and inversions" Somatic Cell and Mol. Genetics, 12(6):555–566, 1986.

D'Ambrosio et al, Recruitment and Activation of PTP1C in Negative Regulation of Antigen Receptor Signaling by FcγRIIB1, Science, 268:293–297, 1995.

Man Sung Co et al., "Humanized anti–lewis Y antibodies: in vitro properties and pharmacokinetics in Rhesus monkeys", Can. Res., 56:1118–1125, 1996.

Ono et al, "Deletion of SHIP or SHP–1 reveals two distinct pathways for inhibitory signaling", Cell, 90:293–301, 1997.

Parren et al, "Characterization of IgG FcR–Mediated proliferation of human T cells induced by mouse and human anti–CD3 monoclonal antibodies", J. Immunol., 148(3):695–701, 1992.

Steplewski et al, "Biological activity of human–mouse IgG1, IgG2, IgG3 and IgG4 chimeric monoclonal antibodies with antitumor specificity", Proc. Natl. Acad. Sci., 85(13):4852–4856, 1988

Lund et al, "Human FcγRI and FcγRII interact with distinct but overlapping sites on human IgG", J. Immunol., 147(8):2657–2662, 1991.

Man Sung Co et al, "Chimeric and humanized antibodies with specificity for the CD33 antigen", J. Immunol., 148(3):1149–1154, 1992.

Wakai et al, "Anti–CD23 monoclonal antibodies: comparisons of epitope specificities and modulating capacities for . . . production", Hybridoma, 12(1):25–43, 1993.

Shakib et al, "A study of the interrelationship between circulating IgG subclass anti–IgE autoantibodies, IgE and . . . asthma", Allergol. et Immunopathol., 21(1):20–24, 1993.

Spiegelberg, "Fc Receptors for IgE and Interleukin–4 induced IgE and IgG4 Secretion", J. Invest. Dermatol., 94(6):49S–52S 1990.

Maliszewski, "Induction of B cell activities by interleukin 4 is inhibited by a receptor–specific monoclonal antibody in vitro", Eur. J. Immunol., 20:1735–1740, 1990.

Yanagihara et al, "Suppression of IgE production by IPD–1151T (Suplatast Tosilate), a new dimethylsulfonium agent: (1) regulation . . . response", Japan J. Pharmacol., 61:23–30 (1993).

Hjulström, "No role of interleukin–4 in CD23/IgE–mediated enhancement of the murine antibody response in vivo", Eur. J. Immunol., 25:1469–1472, 1995.

Escura et al, "Regulation and targeting to T–cell immune responses by IgE and IgG antibodies", Immunol., 86:343–350, (1995).

Bonnefoy et al, "Production and characterization of a monoclonal antibody specific for the human lymphocyte low affinity receptor fyIgE", J. Immunol., 138:2970–2978, 1987.

Gustavsson et al, "CD23/IgE–mediated regulation of the specific antibody response in vivo", J. Immunol., 152(10):4793–4800, 1994.

Yanigihara et al, Éstablishment of sensitive radioimmunoassay for the detection of human IgE–binding factor (soluble CD23), Int. Arch. of Allergy Immunol., 98:189–199, 1992.

Flores–Romo et al, "Inhibition of an in vivo antigen–specific IgE response to antibodies to CD23", Science, 261:1038–1041, 1993.

Luo et al, "Cross–linking of CD23 antigen by its natural ligand (IgE) or by anti–CD23 antibody prevents B lymphocite proliferation and differentiation", 146(7):2122–2129, 1991.

Pène et al, "IgE production by normal human lymphocites is induced by interleukin 4 and suppressed by interferons γ and α . . . $E_2$", Proc. Natl. Acad. Sci., 85:6880–6884, 1988.

Sarfati et al, "Possible role of human lymphocyte receptor for IgE (CD23) or its soluble fragments in the in vitro synthesis of human IgE[1]", J. Immunol., 141(7):2195–2199, 1988.

Henchoz–Lecoanet et al., "The Epstein–Barr virus–binding site on CD21 is involved in CD23 binding and interleukin–4–induced IgE and IgG4 . . . B cells", J. Immunol., 88:35–39, 1996.

Bonnefoy et al, "Receptors for IgE", Cur. Opinion in Immunol., 5:944–949, 1993.

Pène et al, "Modulation of IL–4–induced human IgE production in vitro by IFN–γ and IL–5: the role of soluble CD23 (s–CD23)", J. Cell. Biochem., 39:253–264 (1989).

Aubry et al, "CD21 is a ligand for CD23 and regulates IgE production", Nature, 358:505–507, 1992.

Grosjean et al, "CD23/CD21 interaction is required for presentation of soluble protein antigen by lymphoblastoid B cell . . . clones", Eur. J. Immunol., 24:2982–2986, 1994.

Nambu et al, "Functional significance of CD23– on CD23–transfected Th2 clone", Immunol. Letters, 44:163–167, 1995.

Burton et al, "Human Antibody Effector Function", Adv. Immunol., 51:1–84, 1992.

* cited by examiner

Summary of *in vitro* Mab studies on primate monoclonal antibody 5E8 and PRIMATIZED® versions of 5E8

| Antibody | Apparent Kd (nM) | *In vitro* IgE suppression |
|---|---|---|
| primate 5E8 | 0.5, 1.5, 1.8, 4.4 | +++ |
| p5E8G4P | 0.3, 1.0 | + |
| p5E8G4PN- | 0.3 | + |
| p5E8G1 | 0.7 | +++ |
| p5E8G1N- | 0.7 | +++ |

◄──────► PRIMATIZED®

FIGURE 4

Effects of primate anti-human CD23 monoclonal antibody 2C8 and 2C8 F(ab')$_2$ on IL-4 induced IgE production

ND GAMMA-3 ANTI-HUMAN
GAMMA-1 AND GAMMA-3 ANTI-HUMAN CD23 MONOCLONAL ANTIBODIES AND USE THEREOF AS THERAPEUTICS

CROSS REFERENCE TO RELATED APPLICATION

This application is a continuation-in-part of U.S. application Ser. No. 08/803,085, filed Feb. 20, 1997, now U.S. Pat. No. 6,011,138, issued Jan. 4, 2000.

FIELD OF THE INVENTION

The present invention relates to monoclonal antibodies which specifically bind human CD23, the low affinity receptor for IgE (FceRII/CD23), and contain either a human gamma-1 or human gamma-3 constant domain, and their usage as therapeutic agents.

BACKGROUND OF THE INVENTION

IgE is a member of the immunoglobulin family that mediates allergic responses such as asthma, food allergies, type 1 hypersensitivity and the familiar sinus inflammation allergic rhinitis and conjunctivitis, and as a result, causes widespread suffering throughout the general population. IgE is secreted by, and expressed on the surface of, B-cells. IgE synthesized by B-cells can be anchored in the B-cell membrane by a short transmembrane domain linked to the mature IgE sequence. Membrane and secreted versions of IgE are formed in the same cell by differential splicing of the IgE RNA transcript.

IgE also can be bound to B-cells (and T cells, monocytes, Langerhans cells, follicular dendritic cells, natural killer cells, eosinophils and platelets) through its Fc region to a low affinity IgE receptor (FceRII, hereafter "FCEL", and to mast cells and basophils through its Fc region to a high affinity IgE receptor FceRI, (hereinafter "FCEH"). The low affinity IgE receptor is generally referred to in the literature as CD23.

Upon exposure of a mammal to an allergen, antigen presenting cells process the antigen for presentation to helper T cells. These helper T cells secrete cytokines such as IL-4 which assist B-cells to undergo clonal amplification and secrete more allergen-specific IgE. This newly synthesized IgE in turn is released into the circulation where it binds to mast cells and basophils through the high affinity receptor on their cell surface. Such mast cells and basophils are thereby sensitized to the specific allergen. The next exposure to the same allergen causes binding to specific IgE on the surface of mast cells, and basophils, thereby crosslinking the FceRI on these cells and thus activating their release of histamine and other factors which are responsible for clinical hypersensitivity and anaphylaxis.

The art has reported antibodies capable of binding to FCEL (CD23)-bound IgE but not IgE bound to FCEH (see, for example, WO 89/00138 and U.S. Pat. No. 4,940,782). These antibodies are disclosed to be clinically advantageous because they bind to IgE which is bound to the low affinity receptor (FCEL) or to circulating IgE's, but do not bind to IgE bound to the high affinity receptor (FCEH). Therefore, these antibodies will not activate mast cells or basophils.

Moreover, anti-CD23 antibodies have been reported to have potential as therapeutics, e.g., for the treatment of allergic disorders, inflammatory diseases, and autoimmune diseases. For example, Bonnefoy et al., WO 9612741, report that ligands which bind CD23, e.g., monoclonal antibodies, are useful in the treatment or prophylaxis of inflammatory, autoimmune and allergic diseases.

The usage of monoclonal antibodies to CD23, as both IgE agonists and antagonists has been reported. IgE antagonists have been reported to have potential utility in treatment of conditions or diseases wherein IgE suppression is therapeutically desirable, e.g., allergic conditions such as allergic rhinitis and conjuntivitis, atopic dermatitis and asthma. For example, Bonnefoy et al., WO 8707302 (1987), report monoclonal antibodies to human CD23, which are assertedly useful for assaying the presence of IgE receptors on cell types and as therapeutics in diseases wherein modulation of IgE is therapeutically desirable.

In part because of their potential as therapeutics and diagnostics, many groups have reported the generation of monoclonal antibodies to CD23. See, e.g., Rector et al., Immunol., 55:481–488 (1985); Suemura et al., J. Immunol., 137:1214–1220 (1986); Noro et al., J. Immunol., 137:1258–1263 (1986); Bonnefoy et al., J. Immunol., 138:2970–2978 (1987); Flores-Romo et al., Science, 261:1038–1046 (1993); Sherr et al.; J. Immunol., 142:481–489 (1989); and Pene et al., Proc. Natl. Acad. Sci., USA, 85:6880–6884 (1988). Moreover, as discussed supra, the usage of such antibodies specifically to inhibit IgE production in systems where IgE synthesis is cytokine (IL-4) induced has also been reported. (Flores-Romo et al (Id.); Sherr et al. (Id.); Bonnefoy et al. (WO 8707302); Bonnefoy et al. (WO 8707302); Bonnefoy et al. (WO 9612741)); Bonnefoy et al., Eur. J. Immunol 20:139–144 (1990); Sarfati et al., J. Immunol 141:2195–2199 (1988) and Wakai et al., Hybridoma 12:25–43 (1993). Also, Flores-Romo et al. (Id.) disclose that Fabs prepared from anti-CD23 antibodies inhibit antigen-specific induced IgE responses in vivo in the rat. However, notwithstanding what has been reported, the mechanism by which anti-CD23 antibodies modulate IgE expression and in particular, the manner by which they block IL-4 induced IgE production remains unclear.

It has been suggested that anti-CD23 antibodies inhibit IgE production by signaling through CD23 present on the surface of IgE secreting B cells. It has been proposed that the function of CD23, which is upregulated on IgE secreting B cells, is feedback inhibition of IgE production (Yu, et al. Nature 369, 753–756 (1994)). This has been theorized because mice in which the CD23 gene has been removed have increased and sustained IgE production compared to controls (Yu, et al.). In addition, it has been reported that binding to CD23 by IgE complexes or by a monoclonal antibody to anti-CD23 suppresses ongoing IgE synthesis by a lymphoblastoid cell line that constitutively secretes IgE (Sherr et al. (Id.)). It appears that this is due to down regulation of the messenger RNA for the secreted IgE heavy chain in this cell (Saxon et al., J. Immunol., 147:4000–4006 (1991)). However, the exact mechanism by which IgE expression is inhibited has yet to be explained in systems in which IgE secretion is IL-4 induced.

It has also been reported that crosslinking of Fc gamma RII with surface Ig (B cell receptor) on B cells leads to down regulation of Ig expression. (D'Ambrosia et al., Science, 268:293–297 (1995). A similar mechanism can be proposed for B cells secreting IgE which also have cell surface CD23 and Fc gamma RII. An anti-human CD23 antibody bound to a cell by antigen (CD23) and also bound to Fc gamma RII through Fc interactions could transmit a signal to suppress IgE secretion through Fc gamma RII.

Mechanisms involved in IgE inhibition by anti-CD23 antibodies have been proposed that include blocking interactions other than the interaction between membrane CD23 and IgE. Related to this, CD23, which is a member of the C-type lectin family, has been shown to interact with several other ligands such as CD21, CD11b and CD11c present on a variety of cell types including T cells and monocytes. In this context CD23 can be envisioned as a cellular adhesion molecule.

Therefore, it has been proposed that the CD21–CD23 interaction may be involved in antigen presentation and subsequent IgE production. Models suggest CD21 on B cells sending an activation signal for IgE production after binding to CD23 on activated T cells present primarily in atopic individuals. (Lecoanet et al., *Immunol.*, 88:35–39 (1996); and Bonnefoy et al., *Int. Amer. Allergy Immunol.*, 107:40–42 (1995).) Blocking this interaction with an anti-CD23 could block induced IgE production. (Aubry et al., *Nature*, 358:505–507 and *Immunol.*, 5:944–949 (1993); Grosjean et al. Curr. Opin. *Eur. J. Immunol.*, 24:2982–2988 (1994); Henchoz-Lecoanet et al., *Immunol.*, 88:35–39 (1996) Nambu et al., *Immunol. Lett.*, 44:163–167 (1995); Bonnefoy et al., *Int. Amer. Allergy Immunol.*, 107:40–42 (1995).) It is also possible that antigen presentation is upregulated by CD23 on antigen presenting B cells binding to CD21 on T cells.

Yet another mechanism which would potentially explain the effects of CD23 on IgE production involves soluble forms of CD23. It has been reported that CD23 is cleaved from the cell surface releasing several different forms of soluble CD23 or IgE binding factors. (Sarfati et al., *Immunol.*, 53:197–205 (1984).) Soluble CD23 is a cytokine, with one of its reported activities being the augmentation of IL-4 induced IgE production from B cells. (Pene et al., *J. Cell Biochem.*, 39:253–269 (1989); Pene et al., *Eur. J. Immunol.*, 18:929–935 (1988); Sarfati et al., *J. Immunol.*, 141:2195–2197 (1988); Sarfati et al. (1984) (Id.); (Saxon et al., *J. Clin. Immunol. Allergy*, 86 (3 pt 1) 333–344 (1990). Also, certain forms of soluble CD23 have been reported to inhibit IgE production (Sarfati et al., *Immunol.*, 76:662–667 (1992)). Accordingly, anti-CD23 antibodies potentially may block IgE production by 1) inhibiting the IgE augmenting effects of soluble CD23 and/or 2) blocking the proteolytic release of soluble CD23 from the cell surface.

Thus, based on the foregoing, it is clear that there is significant complexity and uncertainty in the art with respect to the functions of more specifically CD23 and effects on IgE production, and further with respect to the means by which ligands specific thereto affect IgE production.

OBJECTS OF THE INVENTION

Thus, it is an object of the invention to produce novel ligands (antibodies) specific to CD23 and to use such antibodies to elucidate the mechanism by which anti-CD23 antibodies modulate IgE expression.

It is another object of the invention to produce novel ligands (antibodies) which bind CD23, in particular human CD23, having improved ability to inhibit induced IgE expression.

It is a more specific object of the invention to produce anti-human CD23 antibodies containing human gamma-1 or human gamma-3 constant domains.

It is another object of the invention to produce multivalent anti-human CD23 antibodies which may be more effective by virtue of their enhanced potential for cross linking CD23 and Fc receptors.

It is another object of the invention to provide pharmaceutical compositions containing anti-human CD23 monoclonal antibodies comprising human gamma-1 or gamma-3 constant domains which are capable of inhibiting induced IgE production.

It is another object of the invention to use an anti-human CD23 monoclonal antibody comprising a human gamma-1 or human gamma-3 constant domain for treatment or prophylaxsis of disease conditions wherein inhibition of induced IgE production is therapeutically desirable.

More specifically, it is an object of the invention to treat or prevent allergic conditions, autoimmune diseases and inflammatory diseases using an anti-human CD23 monoclonal antibody comprising either a human gamma-1 or human gamma-3 constant domain.

Figure 3:
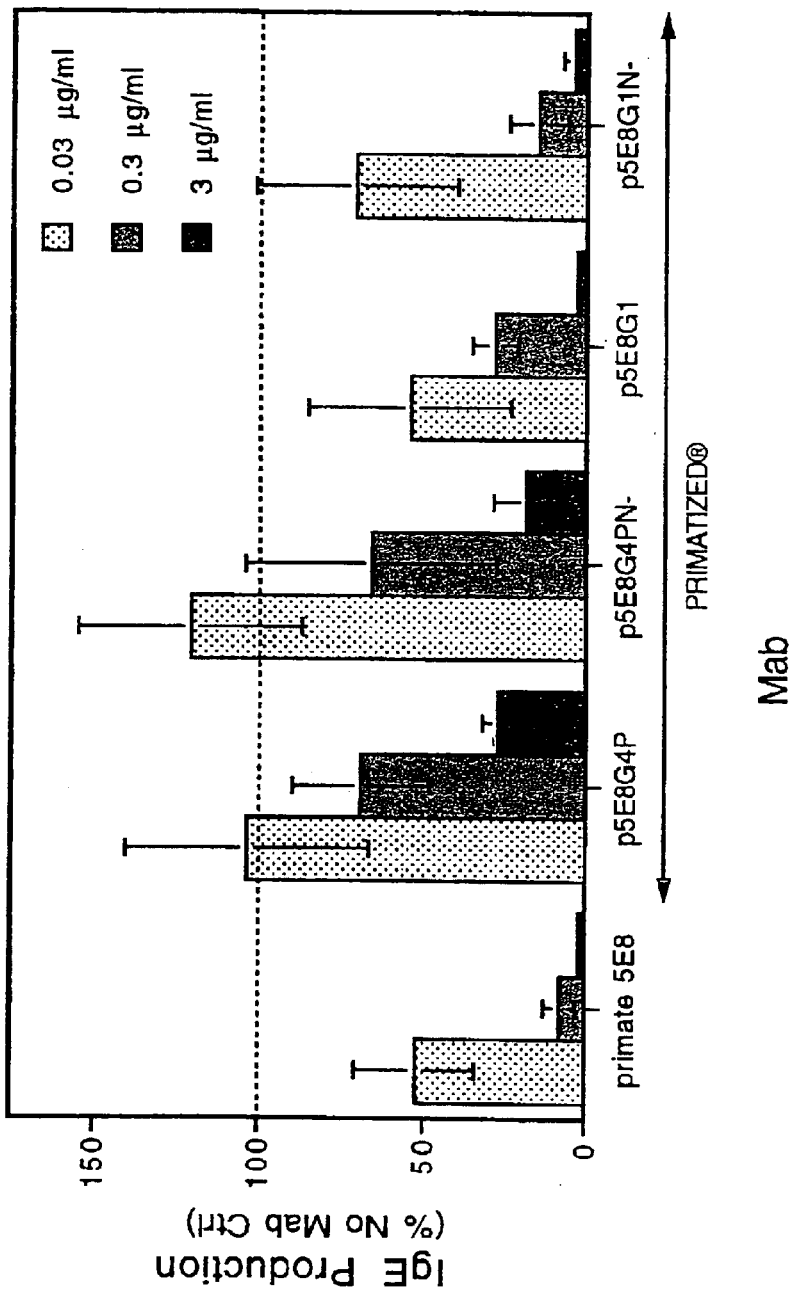
FIG. 3 compares the in vitro IgE inhibitory activity of a particular primate anti-human CD23 monoclonal antibody 5E8 to four different PRIMATIZED® versions of said primate monoclonal antibody, the sequences of which are described below.

p5E8G4P- This PRIMATIZED® antibody contains the following sequences:

Human kappa light chain constant region and a human gamma 4 constant region which contains a P mutation (Angal et al., *Mol. Immunol.*, 30:105–108 (1993));

p5E8G4PN- This PRIMATIZED® antibody contains the human kappa light chain constant region and a human gamma 4 constant region having a P mutation (Angal et al. *Mol. Immunol.*, 30:105–108 (1993)). This antibody also contains a mutation in the heavy chain variable region which changes an asparagine residue (potential carbohydrate attachment site) to a lysine;

p5E8G1 This PRIMATIZED® antibody contains the human kappa light chain constant region and a human gamma 1 constant region;

p5E8G1N- This PRIMATIZED® antibody contains the human kappa light chain constant region and human gamma 1 constant region. This antibody also contains a mutation in the heavy chain variable region which changes an asparagine residue (carbohydrate attachment site) to a lysine;

FIG. 4 contains a table which compares the apparent Kd in nM of the antibodies identified in FIG. 3 and summarizes their IgE suppressive activity.

Figure 5:
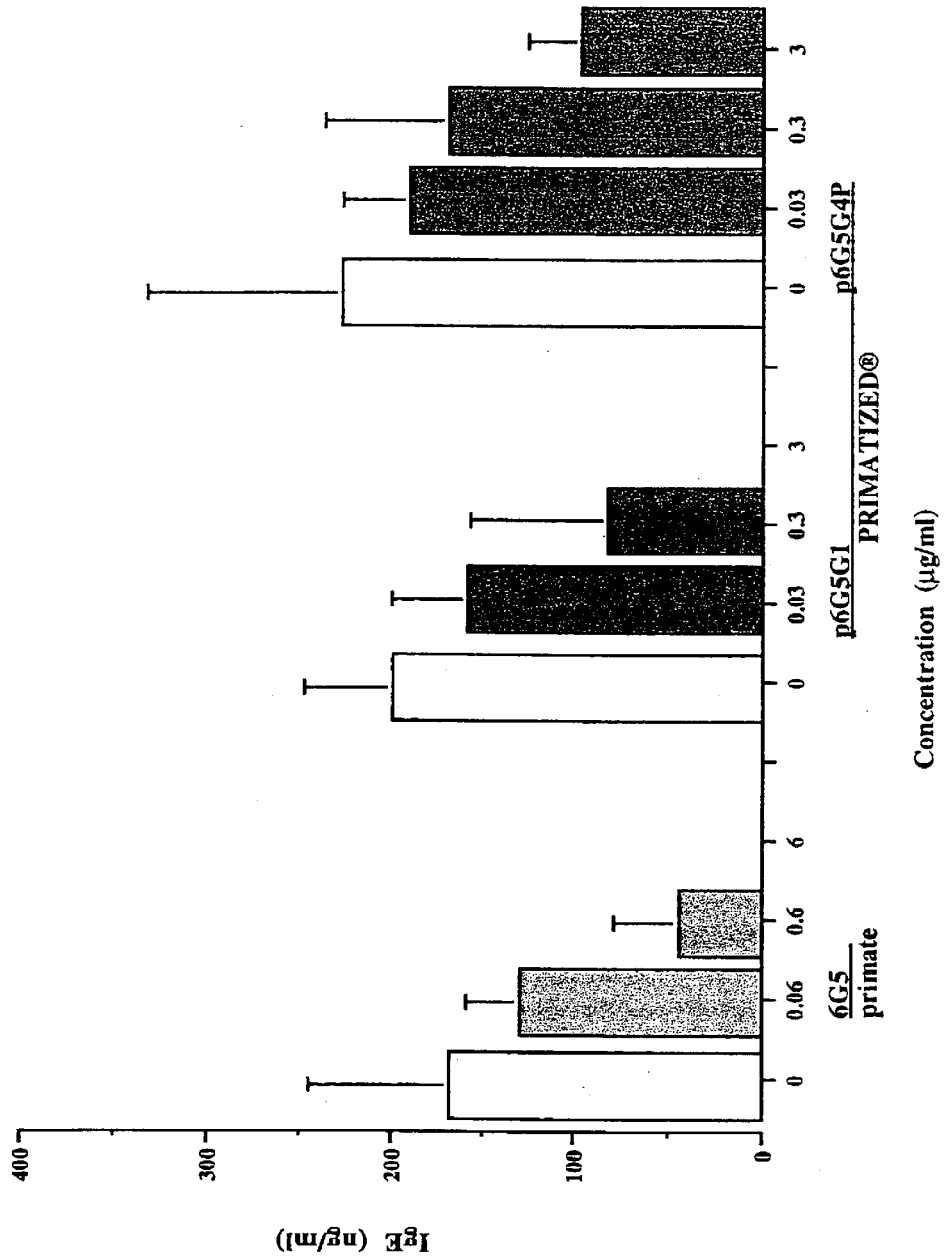
Figure 6:
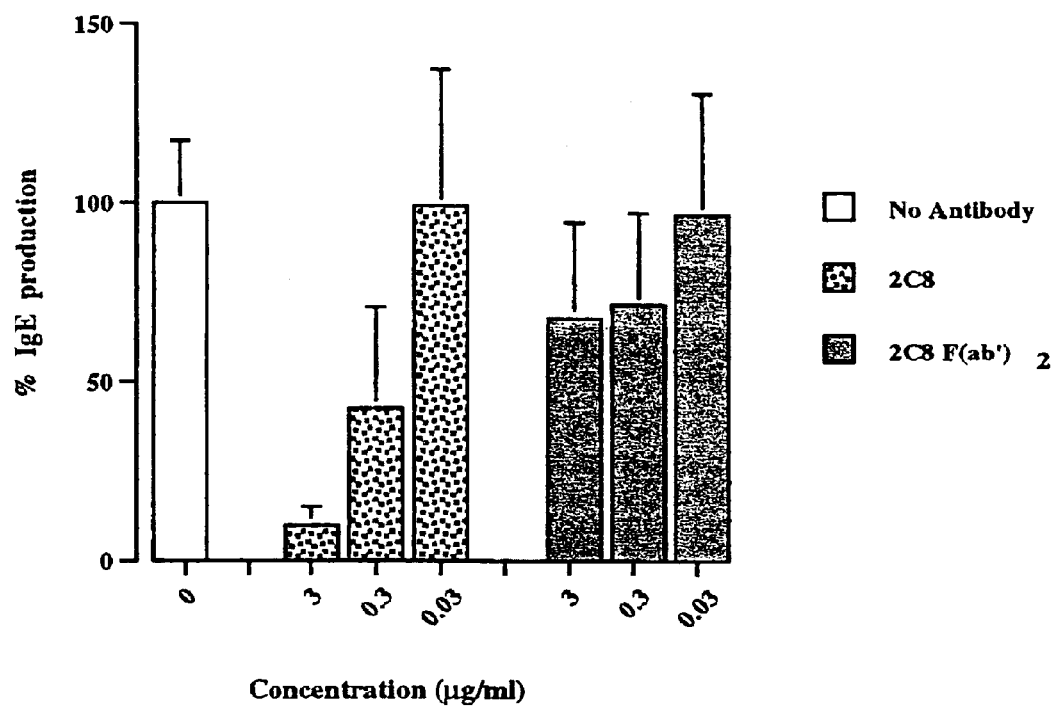
Figure 7:
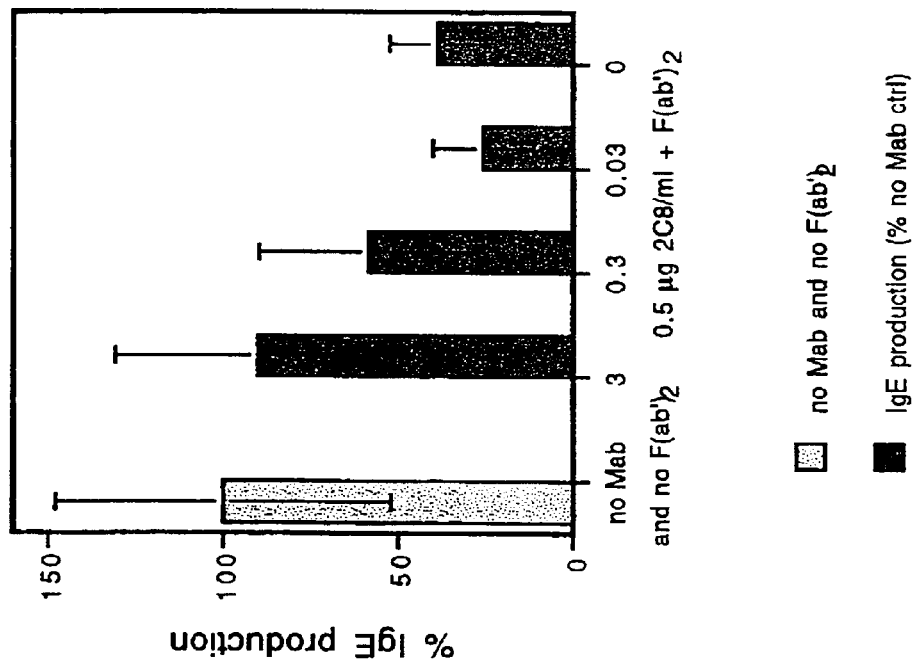

FIG. 5 compares the in vitro IgE inhibitory activity of a particular primate anti-human CD23 monoclonal antibody, 6G5, to two different PRIMATIZED® versions of 6G5 which are described below:

p6G5G1 This PRIMATIZED® antibody contains the human lambda light chain constant region and the human gamma 1 constant region;

p6G5G4P This PRIMATIZED® antibody contains the human lamda light chain constant region and the human gamma 4 constant region with a P mutation (Angal et al., *Mol. Immunol.*, 30:105–108 (1993));

FIG. 6 compares the in vitro IgE inhibitory activity of primate anti-human CD23 monoclonal antibody 2C8 to F(ab')$_2$ derived from 2C8;

FIG. 7 shows that the F(ab')₂ derived from 2C8 antagonizes the suppression of in vitro IgE activity of primate anti-human CD23 monoclonal antibody 2C8.

Figure 8:
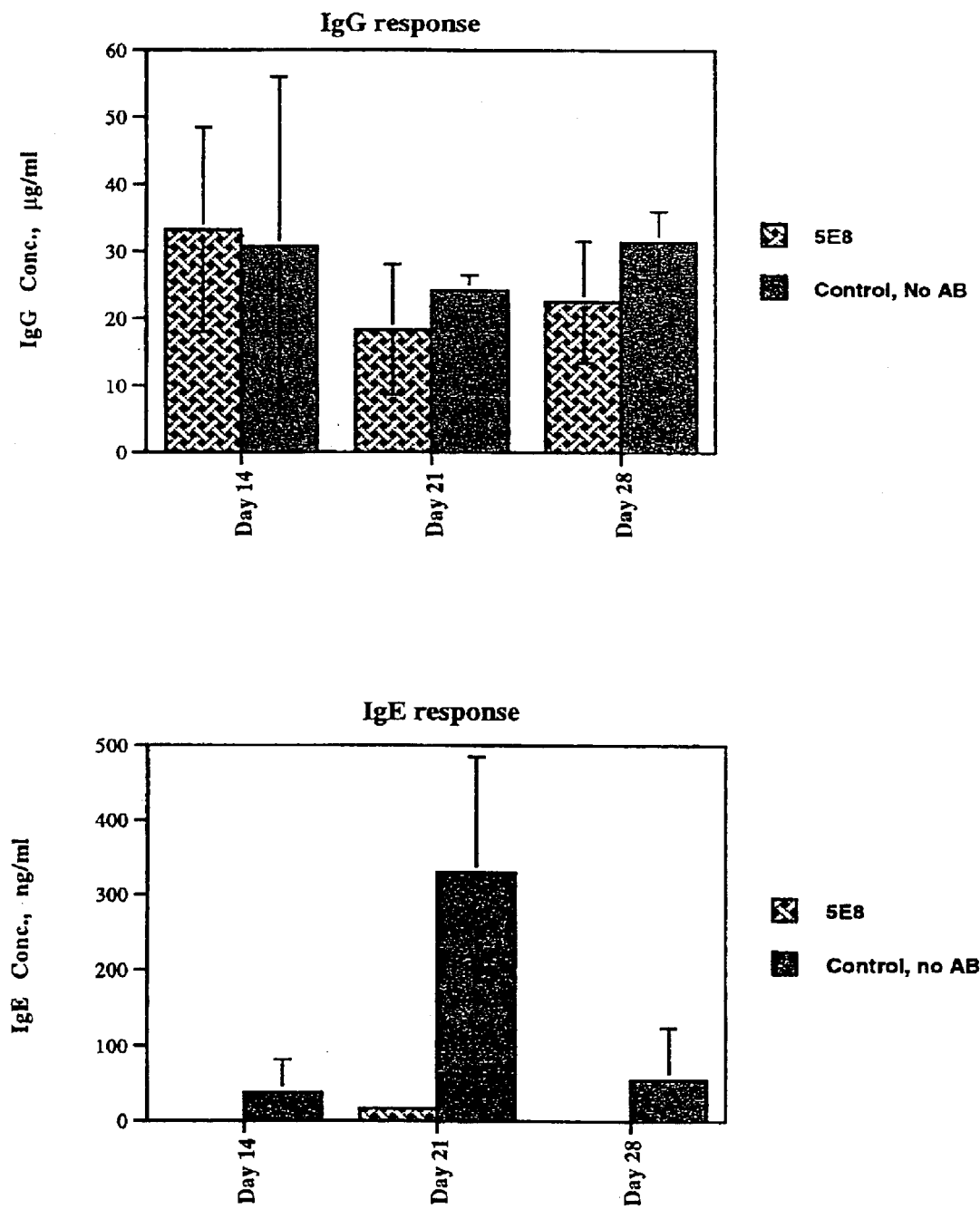
Figure 9:
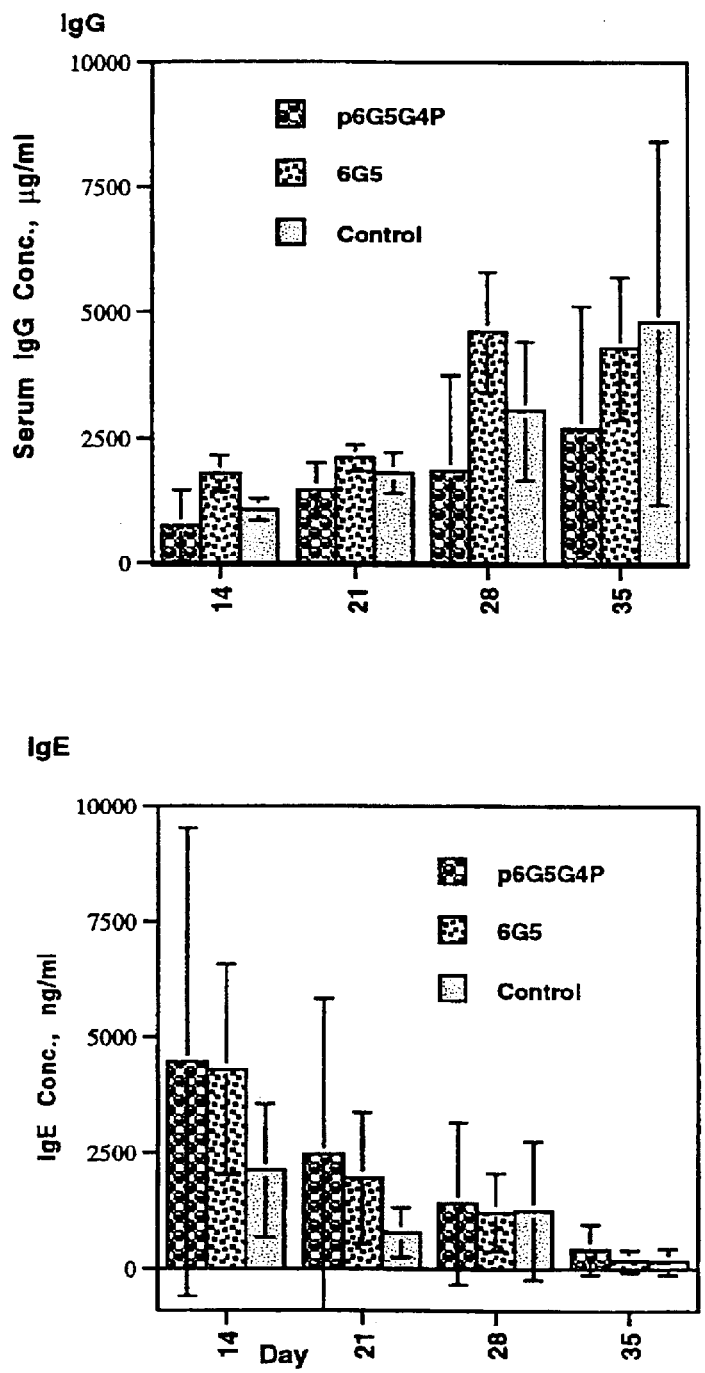

FIG. 8 shows the in vivo IgE inhibitory activity of a particular primate anti-human CD23 monoclonal antibody, 5E8, in a SCID animal model;

FIG. 9 compares the in vivo inhibitory activity of primate anti-human 6G5 and a PRIMATIZED® version thereof p6G5G4P.

Figure 10:
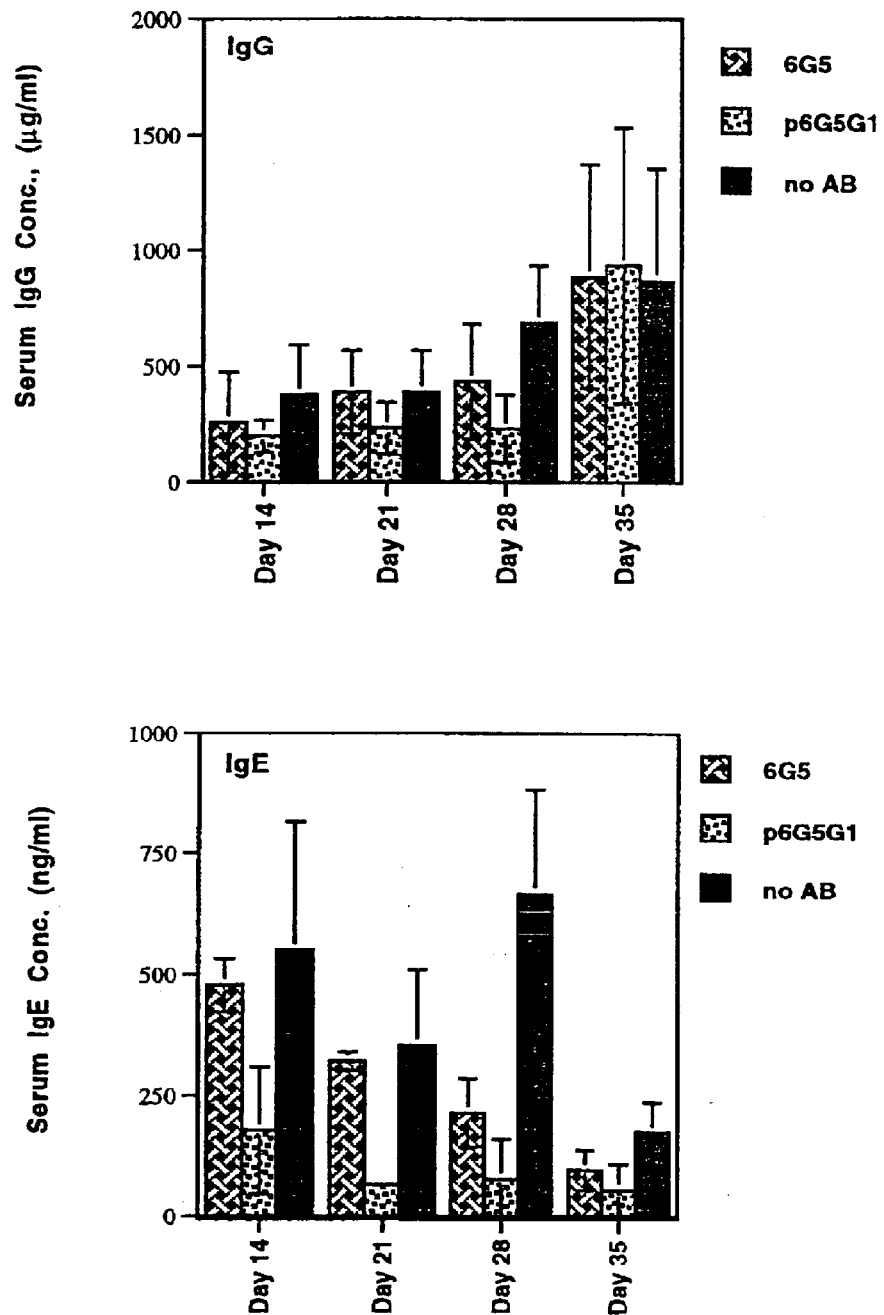

FIG. 10 shows the in vivo IgE inhibitory activity of the primate anti-human CD23 monoclonal antibody 6G5 and a PRIMATIZED® version thereof, p6G5G1.

DEFINITION OF TERMS USED IN THIS APPLICATION

Chimeric Antibody

A recombinant antibody containing regions from two different antibodies, usually different species antibodies, most typically rodent variable sequences and human constant domain sequences.

Anti-Human CD23 Gamma 1 Antibody

An antibody that specifically binds human CD23 which contains a human gamma 1 constant region or fragment or modification thereof which inhibits induced IgE production. This includes, in particular, antibodies containing rodent or primate variable domains or antigen binding portions, humanized, PRIMATIZED®, and human anti-human CD23 monoclonal antibodies which comprise a human gamma 1 constant domain, fragment, or modification thereof, which inhibit induced IgE production in vitro.

Anti-Human CD23 Gamma 3 Antibody

An antibody that specifically binds human CD23 which contains a human gamma 3 constant region or fragment or modification thereof which inhibits induced IgE production. This includes, in particular, antibodies containing rodent or primate variable domains or antigen binding portions, humanized, PRIMATIZED®, and human anti-human CD23 monoclonal antibodies which comprise a human gamma 3 constant domain, fragment, or modification thereof, which inhibit induced IgE production in vitro.

Modifications of Antibody Constant Domains

Antibodies according to the present invention containing mutations, substitutions or deletions of the constant region, that may create a desired change in the level of efficiency, i.e. in FcR binding, without changing the basic effector functions mediated by the constant region.

PRIMATIZED® Antibody

A recombinant antibody containing primate variable sequences or antigen binding portions, and human constant domain sequences.

Humanized Antibody

A recombinant antibody containing a non-human variable region or antigen binding portion which has been modified to more closely mimic a human antibody variable region and thereby eliminate or minimize potential immunogenicity if administered to humans without sacrificing the specificity or affinity of the immunoglobulin. There are several known methods of humanization, including, "veneering" which comprises select modification of surface residues, framework replacement, (CDR grafting) and molecular modeling.

Gamma 1 Constant Domain

A particular type of constant domain sequence which confers upon an antibody specific effector activities. In the present application, gamma 1 constant domain refers to a human gamma 1 constant domain, fragment or modification thereof, which retains gamma 1 effector functions in combination with anti-CD23 variable domain sequences or antigen binding portions. Modifications include human gamma-1 constant domains which comprise the deletion, substitution or addition of one or more amino acid residues. This effector function is manifested by the ability of an antibody containing such a constant domain to inhibit induced IgE production.

Gamma 3 Constant Domain

A particular type of constant domain sequence which confers upon an antibody specific effector activities. In the present application, gamma 3 constant domain refers to a human gamma 3 constant domain, fragment or modification thereof, which retains gamma 3 effector functions in combination with anti-CD23 variable domain sequences or antigen binding portions. Modifications include human gamma-3 constant domains which comprise the deletion, substitution or addition of one or more amino acid residues. This effector function is manifested by the ability of an antibody containing such a constant domain to inhibit induced IgE production.

CD23

This refers to the low affinity receptor for IgE, FcεRII/CD23.

Anti-CD23 Antibody

An antibody that specifically binds CD23, preferably human CD23.

DETAILED DESCRIPTION OF THE INVENTION

As discussed supra, while many groups have previously reported the production of anti-CD23 antibodies and the use thereof as antagonists and agonists for modulating IgE production, the exact mechanism by which such antibodies modulate IgE expression in systems where IL-4 induces IgE production remains unclear. Thus, it would be beneficial if the means by which such antibodies modulate IgE expression were elucidated, or at least better explained, as such information would be potentially useful in designing therapeutics for treatment of diseases wherein modulation of IgE production is therapeutically desirable. In particular, it would be beneficial if improved antibodies specific to CD23 were obtained having improved capacity to inhibit induced IgE production, as enhanced IgE levels are believed to be involved in numerous disease processes, e.g., allergic conditions, inflammatory conditions and autoimmune diseases. Such diseases include by way of example, atopic dermatitis, eczema, allergic rhinitis and conjuntivitis, Job's syndrome, and asthma.

Toward that end, the present inventors have surprisingly discovered that anti-human CD23 monoclonal antibodies which contain human gamma-1 constant domains inhibit IgE production in systems where IgE production is induced by IL-4 significantly better than CD23 monoclonal antibodies of other effector types, e.g., those comprising human gamma-4 constant domains or CD23 monoclonal antibodies or antibody fragments lacking effector functions altogether. Because human gamma-3 constant domains have been shown to mediate the same effector functions as human gamma-1, anti-human CD23 monoclonal antibodies containing human gamma-3 constant domains are also included.

There are currently five defined effector functions for the IgG (gamma) class of antibodies. Two of these functions, complement activation and FcγRN interaction, are not found in the in vitro assays described in the present invention, and are therefore not likely to be involved in the molecular mechanism. Three other FcγR receptors have been identified which interact with the IgG class of antibodies: FcγRI, FcγRII (of which there are at least six different proteins) and FcγRIII (with at least two different proteins). All three of these receptors interact with both IgG1 and IgG3.

FcγRI is the only one of the three having an appreciable affinity for IgG. It binds both monomeric gamma-1 and gamma-3 with a $K_a$ of about $5\times10^8$ $W^{-1}$. However, its affinity for human gamma-4 is about 10-fold less, and it does not bind human gamma-2 at all (Fries et al., 1982, J. Immunol. 129: 1041–1049; Kurlander and Batker, 1982, J. Clin. Invest. 69: 1–8; Woof, 1984, G. Mol. Immunol. 21: 523–527; see also Burton and Woof, 1992, *Human Antibody Effector Function*, Adv. Immunol. 51: 1–84).

Although the affinity of human FcγRII and FcγRIII for human IgG is generally very low ($K_a<10^7$ $M^{-1}$), affinity for human IgG1 and human IgG3 increases significantly ($K_a\approx 2$ to $5\times10^7$ $M^{-1}$) when they are bound to antigen (Karas et al., 1982, Blood 60: 1277–1282). The affinity of human FcγRII for human IgG2 bound to antigen has given conflicting results. Human FcγRIII does not bind to human IgG2. Human FcγRII and human FcγRIII do not bind to human IgG4 (Van de Winkel and Anderson, 1991, J. Leuk. Biol. 49: 511–524; Huizinga et al., 1989, J. Immunol. 142: 2359–2364).

While Fc mediated effector functions are sometimes significant to the therapeutic activity of antibodies, this discovery was surprising in the case of anti-CD23 antibodies because the role of effector function in the IgE inhibitory activity of anti-CD23 antibodies had not been previously reported. In fact, previous evidence had suggested that antibody effector function was not significant to the ability of anti-CD23 antibodies to inhibit induced IgE production. For example, Flores-Romo et al., *Science*, 261:1038–1041 (1993) had reported that Fabs prepared from a polyclonal anti-CD23 antibody inhibited an in vivo induced IgE antigen-specific response.

The discovery that effector functions mediated through the constant region of the anti-CD23 antibodies are apparently involved was made after the present inventors isolated various primate antibodies specific to CD23 having anti-IgE inhibiting activity and compared these antibodies to PRIMATIZED® versions with respect to their ability to inhibit IL-4 induced IgE production in vitro and in vivo. Antibodies constructed with a human gamma-4 constant region failed to inhibit IgE antigen-specific responses in vitro, whereas antibodies containing a human gamma-1 constant region were succesful.

Because one (or more) of the three classes of FcγR receptors, FcγRI, FcγRII or FcγRIII, is likely involved in the specific effector function mediated through the gamma-1 domain, and because these classes of receptors also bind to antibodies containing gamma-3 domains, it is logical that anti-CD23 antibodies containing gamma-3 domains will also be successful at inhibiting IgE-antigen specific-response in vitro.

More specifically, and as described in greater detail infra, five primate monoclonal antibodies which specifically bound both cellular and soluble CD23 were isolated from an Old World monkey (macaque) according to the methodology which is disclosed in commonly assigned application Ser. No. 08/379,072 which issued as U.S. Pat. No. 5,658,570 on Aug. 19, 1997, and which is incorporated by reference in its entirety herein. This application described in detail a means for producing monoclonal antibodies to desired antigens, desirable human antigens, in Old World monkeys and their advantages in relation to antibodies of other species as therapeutics, for example reduced or potentially lack of immunogenicity in humans because of the phylogenetic closeness of humans and Old World monkeys. In fact, because of the phylogenetic closeness of these species, it is difficult to distinguish Old World monkey immunoglobulins from human immunoglobulins by sequence comparison.

Four of these five primate monoclonal anti-human CD23 antibodies were demonstrated to be capable of inhibiting IL-4 induced IgE production in an in vitro B cell assay described in detail infra and the most potent was also shown to inhibit IL-4 induced IgE in a SCID mouse animal model (also described in detail infra). Based on this IgE inhibitory activity, and expected low immunogenicity in humans, such antibodies are potentially suitable as therapeutics for treating diseases wherein inhibition of IgE production is therapeutically desirable.

However, in order to further reduce immunogenicity, it was elected to PRIMATIZE® two primate monoclonal antibodies (a type of chimerization of antibodies) according to the methodology which is also described in U.S. Ser. No. 08/379,072 (U.S. Pat. No. 5,658,570), which is incorporated by reference herein. PRIMATIZATION® essentially refers to the production of recombinant antibodies developed by IDEC Pharmaceuticals Corporation which comprise primate variable regions and human constant regions. PRIMATIZATION® of the two primate anti-human CD23 monoclonal (5E8 and 6G5) antibodies having potent IgE inhibiting activity was effected in order to eliminate any potential immunogenicity attributable to the primate constant domains in humans.

Again, because of the inventors' initial expectation from published literature that Fc effector function was not necessary for induced IgE inhibition, human gamma 4 versions of these particular antibodies were initially produced. However, quite surprisingly, it was found that the gamma-4 versions produced from both of these primate monoclonal antibodies were ineffective, i.e., they required significantly higher concentrations of PRIMATIZED® gamma 4 antibody than the primate antibody to inhibit IL-4 induced IgE production in in vitro assays.

Moreover, even more surprising was the discovery that when the same two primate antibodies were then converted to human gamma-1 versions (by substitution of the primate constant domains with human gamma-1 constant domains), that these gamma-1 antibodies very effectively inhibited induced IgE production in vitro. Thus, our results suggested that Fc effector function is apparently significant to the ability of anti-human CD23 antibodies to inhibit induced IgE production. This hypothesis was confirmed when a third primate anti-human CD23 monoclonal, i.e., the 2C8 antibody, which was shown by us to inhibit IgE production in vitro, was converted to a F(ab')$_2$, which was found to be substantially incapable of inhibiting induced IgE production in vitro. In fact, this F(ab')$_2$ was found to antagonize the suppressive effects on induced IgE blocking activity of the primate anti-human CD23 monoclonal antibody 2C8.

In addition, it was found that removing a glycosylation site in the heavy chain variable region of one of the antibodies (5E8) had no effect on binding of the antibody to CD23 (as evidenced by obtained Kd values), or on induced IgE inhibition. Thus, the differences in IgE inhibition were shown to apparently not involve glycosylation differences.

The PRIMATIZED® gamma 1 version of primate 6G5 was found to inhibit induced IgE expression in SCID mice while the same concentration of either the primate 6G5 or the PRIMATIZED® p6G5G4p did not inhibit induced IgE expression. Therefore, an antibody containing human gamma-1 constant domains was found to be even more effective in an in vivo animal model than the primate monoclonal antibody. Furthermore, the inventors anticipate that anti-CD23 antibodies containing human gamma-3 constant domains will be just as effective as those having gamma-1 constant domains, because gamma-1 and gamma-3 constant domains have affinity for the same classes of Fc receptors.

Accordingly, based on these results, it has been surprisingly discovered that an active Fc region, in particular that of human gamma-1 or human gamma-3, is significantly involved in the mechanism of IL-4 induced IgE inhibition by anti-human CD23 monoclonal antibodies. This discovery is quite unexpected especially based on earlier reports that Fabs derived from polyclonal anti-CD23 antibodies were capable of inhibiting induced IgE production, and also based on the various theories as to how CD23 affects induced IgE expression.

Accordingly, the present invention relates to anti-human CD23 antibodies containing human gamma-1 or gamma-3 constant domains and their use as therapeutics based on their ability to effectively inhibit IgE expression.

The skilled artisan can prepare anti-human CD23 antibodies containing either human gamma-1 or gamma-3 constant domains by methods which are well known in the art for the manufacture of chimeric antibodies. Essentially, such methods comprise producing anti-human CD23 antibodies in a desired host or in vitro, cloning a hybridoma or cell line which produces an anti-human CD23 monoclonal antibody exhibiting desirable characteristics, e.g., adequate CD23 binding affinity, cloning the nucleic acid sequences which encode such antibody from said hybridoma or cell line, e.g. by polymerase chain reaction using suitable primers, isolating the variable domains contained therein, recombining such variable domains with human gamma-1 or gamma-3 constant domains and the appropriate human light chain constant domain, and expressing the resultant nucleic acid sequence encoding a chimeric anti-human CD23 gamma-1 or gamma-3 immunoglobulin in a suitable expression system. Preferably, the anti-human CD23 antibodies of the invention will have apparent CD23 binding affinities ranging from 0.1 nM to 1000 nM, more preferably at least 50 nM, and most preferably at least 5 nM.

Host cells suitable for expression of recombinant immunoglobulins are well known in the art. For example, recombinant antibodies may be expressed in Chinese hamster ovary (CHO) cells, DG44 or DUXB11; or CHO cells CHO K-1; mouse myeloma cells SP2/0 or X63-Ag8.653 or NSO; rat myeloma cells YB2/0; baby hamster kidney cells, BHK; human embryonic kidney line, 293; monkey kidney cells, CV1; human lung fibroblasts, WI38; human cervical carcinoma cells, HELA; insect cells, plant cells, yeast or in bacteria. Further, vectors suitable for expression of immunoglobulins are also well known in the art and are commercially available.

A particularly preferred vector system is the translationally impaired vector system disclosed in U.S. Ser. No. 08/147,696 which issued as U.S. Pat. No. 5,648,267 on Jul. 15, 1997, which comprises a translationally impaired dominant selectable marker (neo) containing an intron into which a desired heterologous DNA is inserted. This vector system has been found to provide for very high yields of recombinant proteins, e.g., immunoglobulins. However, the subject anti-CD23 antibodies may be produced in any vector system which is suitable for expression of functional immunoglobulins.

Also, the present invention embraces human monoclonal antibodies of the gamma-1 or gamma-3 types which are specific to human CD23. Methods for isolation of human monoclonal antibodies are also well known in the art and include in vitro methods, e.g., in vitro immunization of human B cells in tissue culture, and in vivo methods, e.g. synthesis of human monoclonal antibodies in SCID mice. A preferred means of producing human monoclonal antibodies in SCID mice which combines in vitro priming of human spleen cells which are then introduced into SCID mice is disclosed in U.S. Ser. No. 08/488,376 which issued as U.S. Pat. No. 5,811,524 on Sep. 22, 1998 (incorporated by reference in its entirety herein). This method is advantageous as it provides for the reproducible recovery of monoclonal antibodies having high affinity against a desired antigen, e.g., a human antigen.

Also, the present invention embraces human monoclonal antibodies which compete with the primate anti-human CD23 monoclonal antibodies 5E8 and 6G5 for binding to CD23.

EXAMPLE 1

Production of Primate Anti-CD23 Antibodies

Five primate monoclonal antibodies specific to CD23 were isolated from macaques substantially according to the methodology disclosed in Ser. No. 08/379,072 (U.S. Pat. No. 5,658,570), which has been incorporated by reference herein. The exact techniques utilized are described in detail below.

Methodology for Isolation and Characterization of Anti-Human CD23 Monoclonal Antibodies
Purification of the Immunogen sCD23 from 8866 Cells During purification, soluble CD23 (sCD23) was quantified by a three-step ELISA using a murine anti-CD23 antibody (Binding Site; catalog # MC112) as a capture. The antigen was partially purified from cultures of 8866 cells maintained in suspension bioreactors using RPMI 1640 (JRH Biosciences; catalog # 56–509) supplemented with 10% fetal bovine serum (JRH Biosciences) and 4 mM glutamine (JRH Biosciences; catalog # 90114) at 37° C. Carbon dioxide was used to maintain pH 7.1. After removing cells by 0.45 μm filtration, phenylmethyl sulfonyl fluoride (final concentration 0.2 mM, Sigma Chemical Co.; catalog # P-7626) and ethylenediaminetetraacetic acid (final concentration 3 mM, Sigma Chemical Co.; catalog # EDS) were added to the supernate and the solution stored at 2–8° C. The cell-free supernate was concentrated approximately 15 to 20-fold using a hollow-fiber ultrafiltration cartridge (A/T Technology; catalog # UFP-10-C-9A; 10,000 d MWCO) or tangential flow ultrafiltration cartridge (Filtron Corporation; 10,000 d MWCO) at ambient temperature. The concentrated supernate was sterile filtered and stored at −70° C. Thawed concentrates were de-lipidated by adding SM-2 BioBeads (BioRad Industries; catalog # 152-3920) at 5 g/L and stirring overnight at 2–8° C. The resin was removed by filtration and the solution stored at 2–8° C. For some preparations of sCD23, concentrates were fractionated using axninonium sulfate (35–70% (w/v); Fisher; catalog # A702-3) before or after de-lipidation.

The de-lipidated solution was subsequently purified using affinity chromatography at 2–8° C. The affinity matrix was prepared by covalently linking a murine anti-CD23 monoclonal antibody (BU38) to Sepharose using CNBr-activated Sepharose 4B (Sigma Chemical Co.; catalog # C-9142). The BU38 antibody was purified to >90% homogeneity from ascites (Binding Site; catalog # CUS830) using Protein A chromatography. The delipidated solution was applied to the affinity column (1.5×5 cm) equilibrated with 1×PBS (Gibco BRL; catalog # 70013-0.32), pH 7.2 and the column washed with 1×PBS, pH 7.2, containing 0.05% NP40 (Sigma Chemical Co.) to remove non-bound protein. Soluble CD23 was eluted using 3.5 M $MgCl_2$ (Fisher; catalog # M33-500). Fractions containing sCD23 were combined and dialyzed (Baxter Spectra/Por; catalog # D1615-1) against 1×PBS, pH 7.2 at 2–8° C. After dialysis, the protein solution was concentrated by centrifugation using Centriprep 10 spin filters (Amicon Corporation; MWCO 10,000 d) and preparations stored at −70° C. The purity of sCD23 was estimated to be >70% using SDS-PAGE analysis (4–20% pre-cast gels, Novex Corporation) and Coomasie staining.

Immunization of Primates and Isolation of Immune Cells

Cynomolgus monkeys (White Sands Research Center, Alamogordo, N. Mex.) were immunized with soluble CD23 which had been purified from the supernatant of human RPMI 8866 cells (B cell lymphoma, Hassner and Saxon, *J. Immunol.*, 132:2844 (1984)). Each monkey was immunized every third week with 200 µg soluble CD23 in 500 µl PBS mixed with 167 µl Temuritide (adjuvant peptide) (Sigma, St. Louis, Mo., Catalog # A-9519) and 333 µl 3X PROVAX® (IDEC Pharmaceuticals Corporation). Immunization was effected intradermally, intraperitoneally, intramuscularly and subcutaneously. The titer of anti-CD23 antibodies in the serum of the monkeys was measured by ELISA on 8866 cells and compared to a pre-bleed from the same monkeys.

Monkey PRO 978, with a serum titer of fifty thousand was sacrificed, and the spleen and lymph nodes were surgically removed, and shipped on ice to IDEC pharmaceuticals, submerged in sterile RPMI-1640 (Gibco BRL, Gaithersburg, Md., Catalog # 21870-050) supplemented with 10% fetal calf serum, 2 mM L-glutamine, 2 mM sodium pyruvate and 50 µg/ml gentamicin. Immediately upon arrival the spleen was homogenized by squeezing it through a wire mesh with a glass pistil. Red blood cells were lysed in an ammonium chloride based hypotonic buffer and the remaining lymphocytes collected and washed in RPMI-1640 at least three times. Lymph nodes were homogenized similarly into a single cell suspension, collected and washed at least three times in RPMI-1640.

Production of Hybridomas

After the last wash, the cells were counted, and the primate cells obtained above were then somatically fused to the mouse-human heterohybridoma cell line H6K6/B5 (Carroll et al., *J. Immunol. Methods*, 89:61 (1986)) using standard techniques (Boerner et al., *J. Immunol.*, 147:86) (1991)) and plated into 96 well dishes (175 dishes or 14,700 wells for the spleen, and 17 dishes or 1386 wells for the lymph nodes) at 300,000 cells per well.

This procedure involved the mixing of lymphocytes and the above-identified fusion partner, at a 2:1 ratio, which cells were slowly resuspended into 50% PEG 1500 (Sigma, Catalog # P5402) for 1 minute. These cells were then allowed to rest for 1 minute and then slowly further resuspended in excess RPMI-1640. Afterward, the cells were again allowed to rest, this time for 15 minutes before a light spin at 250×g. The cells were then resuspended in RMPI-1640 growth media, which was supplemented with 20% Fetal Calf Serum, 2 mM L-Glutamine, Sodium Pyruvate, Non-Essential Amino Acids and 50 µg/ml Gentamicin, containing 100 µM Hypoxanthine, 16 µM Thymidine (BoehringerMannheim, Germany, # 623091) and 5.8 µM Azaserine (Sigma, Catalog # A 1164) (HTA). HTA is a selection agent which provides the survival of successfully fused cells (primate lymphocyte fused with heterohybridoma fusion partner).

Approximately 65% of the wells showed growth (10,500 wells). These wells were then screened for the presence of anti-human CD23 antibody by a three step cell ELISA.

ELISA Procedure

The first step of the ELISA comprised the transferral of fifty microliters of supernatant from each well to ninety-six well plates which had previously been coated with $10^5$ 8866 cells (CD23 positive cell line) per well. These plates were made by first coating the plates with 50 µl of aqueous solution containing twenty µg/ml Poly L-Lysine (Sigma Catalog # P1399, MW 150,000–300,000) for thirty minutes at room temperature. The remaining solution was removed ("flicked out") and the plates left to dry. Once dry, fifty µl of 8866 cells in PBS were transferred and spun at 600 g for five minutes. The 8866 cells were covalently bound to the plate by adding fifty µl 0.5% glutaraldehyde (Sigma Catalog # G6257) in phosphate buffered saline (PBS) for 15 minutes. The glutaraldehyde was removed (flicked out) and the plates blocked with one hundred fifty µl 100 mM glycine (Sigma Catalog # G-2879) in 0.1% BSA-PBS. After the addition of supernatants, the plates were incubated at 37° C. for one to two hours and washed seven to nine times with tap water, and a goat anti-human IgG antibody coupled to horse radish peroxidase (HRPO) (Southern Biotech, Birmingham, Ala., Catalog # 2040-05) diluted 1:2000 into 1% dry skimmed milk (Vons) in PBS-0.05% Tween 20 (Sigma, Catalog # P1379) was added. The plates were incubated for forty-five minutes at 37° C., and again washed seven to nine times in tap water. The presence of the HRPO was detected by a color development after the addition of a TMB reagent (Kirkegaard & Perry, Gaithersburg, Md., Catalog # 50-76-02 and 50-65-02), 100 µl/well. The reaction was stopped by adding twenty-five µl 4N $H_2SO_4$. Optical density (OD) was measured at 470 nM on a spectrophotometer (Titertek Multiscan). The OD values greater than two times the background were scored as positive.

The second step in the ELISA was effected to confirm that the supernatants which had been scored positive in the first ELISA reacted to CD23 and not to some irrelevant antigen. This was effected by testing the supernatants on SupT1 cells (ERC BioServices Corporation, Rockville, Md., Catalog # 100), a CD23 negative human cell line, using the same ELISA procedure. Supernatants that scored similarly in both tests were discarded. These results indicated that fifty-six of the 10,500 wells with growth showed the presence of a primate monoclonal antibody that bound to 8866 cells in two separate screenings at different times and did not bind to SupT1 cells.

The third step of the ELISA was conducted to determine whether the supernatants identified according to the first two ELISA steps, reacted with soluble CD23. In this third ELISA, 96 well plates were coated at 4° C. overnight with 2 µg/ml BG-6 (Biosource International, Camarillo, Calif., Catalog # CT-CD23-CF), a mouse monoclonal antibody that binds to soluble CD23 but does not block CD23-IgE binding, contained in a 50 mM bicarbonate buffer, pH 9.3. After removing the coating buffer, fifty µl of semi-purified soluble CD23 at a predetermined dilution in PBS were added to the plate and incubated for two hours at room temperature. After washing the plate with tap water seven to nine times, 50 µl supernatants from selected wells were added. After washing the plate in tap water seven to nine times, 50 µl rabbit anti-human IgG (mouse adsorbed)-HRPO (Southern Biotech, Catalog # 6145-05) diluted 1:4000 in 1% dry skimmed milk in PBS with 0.05% Tween 20 were added, incubated for two hours at 37° C., washed seven to nine times in tap water and developed with TMB as described above. Wells with OD's greater than two times the background were again scored as positive.

Twenty-one of the fifty-six wells that showed binding to 8866 cells also bound to sCD23 in the ELISA. These wells were expanded and subcloned at least twice by plating out cells at one cell per three wells. After approximately three months, five stable hybridomas producing primate monoclonal antibodies to CD23 were obtained.

Antibody Purification by Protein A Methods

Essentially, antibodies are purified by centrifugation of the culture supernatant to remove cells and debris. The resultant centrifuged samples are then filtered through a 0.2 µm filter. A protein A sepharose Fast flow column is then prepared and equilibrated using PBS (pH 7.4). The supernatant is then loaded on the column at an appropriate flow rate (2 ml/min). After loading, the wash column is washed with 10 column volume of PBS (pH 7.4). The antibody is then eluted from the column with elution buffer (0.2 M acetic acid, 0.1 M glycine pH 3.5) at 1 ml/min flow rate. One milliliter fractions/tube (2.0 M Tris-Hcl pH 10.0) including 100 µl of Tris, are then collected. Afterward, spectrophotometer readings are taken at 280 nm. The resultant fractions with high absorbance at 280 nm containing the antibody are then collected and dialyzed against PBS overnight. The product is then sterilized by filtration through 0.22 µm membrane and stored at −20° C.

Figure 1:
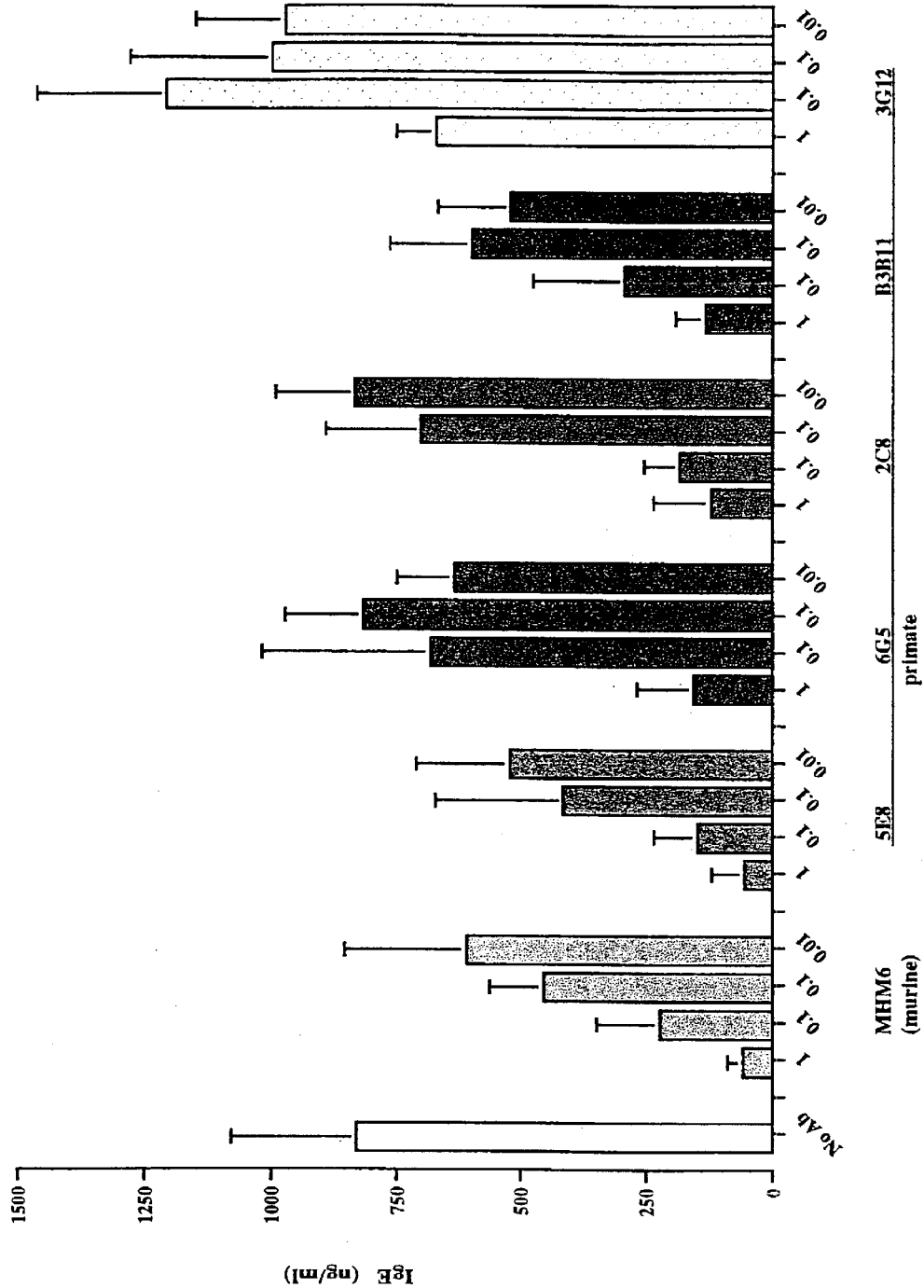
FIG. 1 compares the in vitro IgE inhibitory activity of a murine anti-human CD23 monoclonal antibody (MHM6), to five primate anti-human CD23 monoclonal antibodies (5E8, 6G5, 2C8, B3B11, and 3G12)

Four of these five primate anti-human CD23 monoclonal antibodies (1H6, 2C8, 5E8 and 6G5) were demonstrated to inhibit IgE production in an in vitro assay which measures IgE production by IL4-hydrocortisone induced peripheral blood mononuclear cell (PBMC) cultures. These results are shown in FIG. 1. The assay conditions are described below. The fifth primate monoclonal anti-human CD23 antibody B3B11 was inactive in this assay.

IL-4 Stimulated IgE Production by Peripheral Blood Mononuclear Cells

As discussed supra, the subject primate antibodies and PRIMATIZED® forms thereof were assessed for their ability to inhibit IgE production in an in vitro assay which measured the effect of such antibodies on IgE production by IL-4 stimulated peripheral blood mononuclear cells.

Materials for in vitro IL-4 IgE Assay

Forty-eight well flat bottom cluster plates (Costar Catalog # 3548) (1.5 million PBMCs per ml per well (48 well plate))

Human recombinant IL-4 (Genzyme Catalog # 2181-01; 10 µg (2.5×10$^7$ units).

anti-CD23 Mabs:

murine Mab (MHM6; DAKO. Catalog # M763)

primate Mabs (no preservatives)

PRIMATIZED® (no preservatives)

HB 101 basal medium: (Irvine Scientific Catalog # T000)

HB101 supplement: (Irvine Scientific Catalog # T151)

Fetal Bovine Serum: (FBS; Bio-Whittaker Catalog # 14-501F)

dimethylsulfoxide: (DMSO; Fisher Scientific Catalog # D128-500)

hydrocortisone: (Sigma Catalog # H-0888)

puromycin: (Sigma Catalog # P-7255)

cyclohexamide: (Sigma Catalog # C-7698)

Histopaque®: (Sigma Catalog # H-8889)

Hank's Buffered Salt Solution: (HBSS; Irvine Scientific Catalog # 9232)

1% FBS in HBSS concentrated Dulbecco's phosphate buffered saline (10× DPBS; Bio-Whittaker, Catalog # 17-517Q)

Bath Clear Microbicide (Fisher, Catalog # 13-641-334) in DPBS

Solutions

| | |
|---|---|
| puromycin solution: | 40 µg/ml in HB101 growth medium |
| cyclohexamide solution: | 200 µg/ml in HB101 growth medium |
| hydrocortisone solution: | 0.1 M solution in DMSO |
| anti-CD23 murine Mabs were extensively dialyzed to remove preservatives | |
| HB101 growth medium | |
| HB101 basal medium | 500 ml |
| HB101 supplement in 10 ml sterile filtered distilled H$_2$O | 5 ml |
| FBS | 10 ml |
| hydrocortisone solution (final conc. 5 µM) | 0.25 ml |

In Vitro Assay Procedure

Buffy coat cells 1:4 are diluted using HBSS at room temperature. These cells are derived from whole blood after an overnight incubation at room temperature to resolve and separate the plasma components, clotted platelets and fibrin, and buffy coat cells.

Thirty microliters of diluted buffy coat are then overlayed onto fifteen microliters of Histopaque in fifty ml conical tubes. These tubes are then centrifuged for twenty minutes at 1700 rpm at room temperature without brakes (IEC 216 swinging bucket rotor). The white PBMC layer is then collected using a sterile pipette, taking care not to disturb the other layers. The PBMCs (peripheral blood mononuclear cells) are the buffy coat cells which have been sedimented by centrifugation partially through a HISTOPAQUE® density gradient to form a distinctly visible white layer of cells. These cells are collected with a pipette, rinsed with HBSS, and then counted using a hemocytometer. Typically, 300 to 600 million PBMCs can be recovered from a single 450 ml buffy coat package.

The collected PBMCs are then washed three times in 1% FBS/HBSS. The washed cells are collected by centrifugation for seven minutes at 1300 rpm at 7° C.

The number of cells collected is then determined using a hemocytometer. The cell concentration is adjusted to about three million cells per milliliter of HB101 growth medium.

Approximately about 1.5 million cells (0.5 ml) are then added to each well of a 48 well plate. In general, five replicate samples are prepared for each experiment. The perimeter wells of each plate are not used for cell samples. Accordingly, these wells are filled, e.g., using 0.5 ml of 0.05% BathClear/DPBS.

0.5 ml HB101 growth medium containing desired amounts of IL-4 and Mab is then added to the wells. The IL-4 used is recombinant DNA-generated human interleukin 4. The Mab used in the assay is a murine, primate or PRIMATIZED® antibody. Typically, IL-4 is added at a final concentrate of 100 U/ml and Mab is added at a final concentrate ranging from 0.01 to 3 µg/ml.

The cells are then incubated for nine to eleven days at 37° C. in a moist incubator set at 5% CO$_2$. After incubation, the supernatant fluids are collected and the IgE content is measured.

IgE ELISA

The following list identifies materials and solutions used in the IgE ELISAs.

Materials and Solutions Needed for IgE ELISA
sulfuric acid, 4 M
coating buffer: 10 mM sodium bicarbonate buffer, pH 9.6
concentrated phosphate buffered saline (10×PBS) stock solution:

| | |
|---|---|
| $NaH_2PO_4$ | 26.6 gm |
| $Na_2HPO_4$ | 289 gm |
| NaCl | 1064 gm |
| distilled $H_2O$ | 10 L | blocking buffer: 10% FBS/PBS
dilution buffer: 1% BSA/0.05% Tween 20/PBS
washing buffer: 0.05% Tween 20/PBS
goat anti-human IgE (epsilon chain-specific), unlabeled: (Tago Catalog # 4104)
human IgE standard: (The Binding Site Catalog # BP094)
goat anti-human IgE, HRP-labeled: (Tago Catalog # AHI 0504)
TMB peroxidase substrate: (KPL Catalog # 50-76-02)
peroxidase solution B: (KPL Catalog # 50-65-02)
working substrate solution: mix substrate and Solution B at 1:1 ratio
Immulon II microtiter plates (Dynatech Labs Catalog # 011-010-3455).

IgE ELISA Procedure

Each well of a microtiter plate is coated using 100 μl of a coating buffer containing 2 μg/ml goat anti-human IgE.

The coated plate is then incubated overnight at 4° C.

After incubation, each well in the plate is then washed three times with 200 μl of Tween 20/PBS. After washing, the non-specific binding sites are blocked with 200 μl blocking buffer/well for 1 hour at 37° C.

One hundred μl of samples or standards are then added to each well; which wells are then incubated over-night at 4° C. After incubation, the samples are tested with or without dilution. A standard concentration curve is prepared for each plate using several dilutions of IgE ranging from 0.1 to 50 ng/ml.

After overnight incubation, each plate is washed five times with Tween 20/PBS.

One hundred μl of horseradish peroxidase (HRP) labeled goat anti-human IgE diluted 1:10,000 in dilution buffer is then added to each drained well. The plate is then incubated for 4 hours at 37° C.

The plates are then washed 5 times with Tween 20/PBS and 3 times with water.

One hundred μl of 3,3',5,5'-tetramethylbenzidine working substrate solution is then added to each well. The plate is then incubated for twenty-five minutes in the dark at room temperature. After incubation the developing reaction is stopped by the addition of fifty μl of 4 M sulfuric acid.

The absorbency is then read concurrently at 450 and 540 nm. The 540 nm absorbency values are subtracted as background.

Assay for Kd Measurement of Primate Monoclonal Anti-human CD23 Antibodies

Scatchard Analysis Procedure

1. Radiolabeling Procedure

IODO-BEADS are washed with 100 mN Phosphate Buffer, pH 7.4 twice using 1 mL of buffer per 2 beads. The beads are then dried on filter paper.

The two beads are then added to 100 μl $^{125}I$ solution, containing about 1 mCi of I, diluted with 200 μl of the phosphate buffer, and left at room temperature for 5 minutes.

The antibody (50 μgs) is added to the preloaded beads. The reaction time for maximal incorporation of radioactivity is 6 minutes.

The reaction is stopped by removing the radiolabeled antibody from the reaction vessel.

Gel filtration is then performed to remove excess $^{125}I$ or unincorporated $^{125}I$ from the radiolabeled antibody solution. This is effected by passing the radiolabeled antibody over a column made up of 1.5 mL Sephadex-G25, 1.5 mL DEAE Sephadex-A25 and 0.5 mL Amberlite. The radiolabeled antibody is eluted off in a total volume of 5 mL at a concentration of about 10 μg/mL. (Elution Buffer: 1×PBS containing 10% Gelatin, 2% Sodium Azide and 1% BSA).

2. Optimization Assay (Direct Binding Study)

The specific activity of the 10 μg/mL radiolabeled solution is determined by taking a 1 μl sample and running the sample on a gamma counter.

Example $1×10^5$ cpm/μd×1000 μl/10 μg antibody $1×0^5$ cpm/μg antibody $1×0^4$ cpm/ng antibody Molecular wt. of antibody=75,000 ng/nmole Specific activity: $1×0^4$ cpm/ng×75,000 ng/nmole=$7.5×0^8$ cpm/nmole The antigen-coated plate is blocked (to eliminate non-specific binding, e.g., with mB7.1-CHO) and the background plate (i.e., Untransfected-CHO) for one hour at room temperature with 200 μl/well of blocking buffer (Blocking Buffer: 1×PBS containing 10% Gelatin, 2% Sodium Azide, 1% BSA and 10% FBS).

The plate(s) are then washed, typically ten times by hand with tap water.

The 10 μg/mL radiolabeled antibody (50 μls) is then titrated by two-fold serial dilutions across the plate(s) using a multichannel pipette. Incubate for one hour at room temperature.

The plate(s) are again washed about 6–7 times with 200 μl/well of wash buffer (Wash Buffer:—1×PBS containing 10% Gelatin and 2% Sodium Azide).

The radioactivity counts in each well are then determined by running the wells on a gamma counter.

The optimal radiolabeled antibody concentration is the concentration in which the difference between the specific counts and background counts is at a maximum.

3. Scatchard Analysis of Competition Assay

The 10 μg/mL radiolabeled solution is diluted to the optimal concentration determined in the Direct Binding experiment.

The antigen-coated plate and the background plate are blocked for one hour at room temperature with 200 μl/well of blocking buffer.

The plate(s) are then washed, e.g., about 10 times, by hand with tap water.

The "cold" (no radiolabel) antibody is then titrated by two-fold dilutions in a separate U-bottom microtitre plate. The starting concentration of the "cold" antibody should be at least 100 times greater than that of the optimal radiolabeled antibody concentration.

Example

Optimal Radiolabeled Conc.: 0.5 μg/mL

"Cold" Antibody Conc.: 100 μg/mL (Note: 1:2 titration in the first well will adjust the "cold" antibody concentration to 50 μg/mL.)

Fifty μl/well of optimal radiolabeled antibody are then added to the wells containing "cold" antibody.

One hundred μl/well of the mixed solution are then transferred to the corresponding wells of the antigen-coated plate, and incubated for one hour at room temperature.

Also, it is desirable also that the following controls be effected:

a) Direct binding of radiolabeled antibody to antigen-coated plate (5 wells), b) Direct binding of radiolabeled antibody to background plate (5 wells).

After incubation, the plate(s) are washed, e.g., about 6–7 times, with 200 μl/well of wash buffer.

The radioactivity counts in each well are then determined by running the wells on a gamma counter.

These calculations are determined by calculating the specific counts in each well tested by subtracting the background counts from the counts bound to the antigen-coated plate.

4. Calculations for Scatchard Analysis

The Molar Concentration of Bound antibody [B] can then be determined as follows:

Example: At 50 μg/mL "cold antibody"

Specific counts bound: 4382 cpm

Counts bound in the presence of 50 μg/mL "cold" ab: 215 cpm

Difference: 4382 cpm–215 cpm=4167 cpm $$\text{Specific Activity (radiolabeled ab)}: 5.54 \times 10^9 \text{ cpm/nmole}$$

$$4167 \text{ cpm} \div 5.54 \times 10^9 \text{ cpm/nmole} = 7.52 \times 10^{-7} \text{ nmole}$$

$$7.53 \times 10^{-7} \text{ nmole} \div 0.05 \text{ mL (sample vol.)}$$

$$= 1.50 \times 10^{-5} \text{ nmole/mL}$$

$$= 1.50 \times 10^{-8} \text{ μmole/mL}$$

$$[B] = 1.50 \times 10^{-11} \text{ mole/mL}(M)$$

$$50 \text{ μg/mL} \times 1\text{μmole}/75{,}000 \text{ μg} = 6.67 \times 10^{-4} \text{ μmole/mL}$$

$$= 6.67 \times 10^{-7} \text{ mmole/mL}(M)$$

$$[T] = 66667 \times 10^{-11} \text{ mmole/mL}(M)$$

Free Molar Conc. = Total minus Bound $$[F] = (66667 \times 10^{-11}) - (1.50 \times 10^{-11})$$

$$= 6666.5 \times 10^{-11} \text{ mmole/mL}(M)$$

Calculate B/F.

Plot B versus B/F on Cricket Graph software.

Activity and Affinity of Anti-Human CD23 Antibodies According to the Invention

Four of the five isolated primate anti-human CD23 monoclonal antibodies (B3B11, 2C8, 5E8 and 6G5) were found to inhibit IgE production in the above-identified in vitro assay which measures IgE production by IL4-hydrocortisone induced peripheral blood mononuclear cell (PBMC) cultures. These results are shown in FIG. 1. The fifth primate monoclonal anti-human CD23 antibody 3G12 was inactive in this assay.

Figure 2:
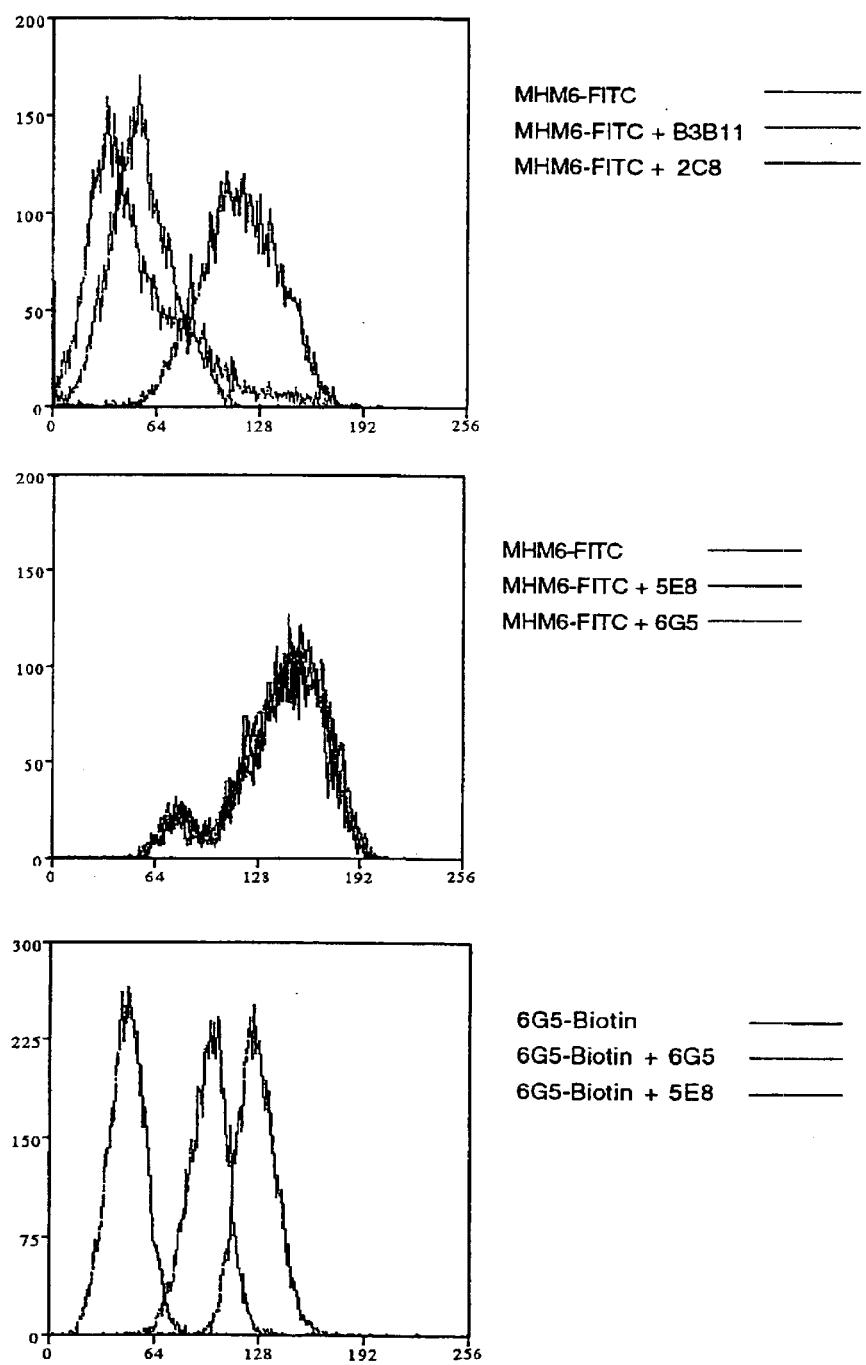
FIG. 2 shows that primate monoclonal antibodies 5E8 and 6G5 bind an epitope on human CD23 that is distinct from commercially available murine anti-human CD23 monoclonal antibody MHM6 (middle panel, FIG. 2) and compete with each other (lower panel, FIG. 2). Primate anti-human CD23 monoclonal antibodies 2C8 and, B3B11 compete with MHM6 top panel, FIG. 2).

Two of the four primate monoclonal anti-human CD23 antibodies (B3B11 and 2C8) found to be active in this in vitro assay were found to compete with a commercially available mouse anti-human CD23 antibody MHM6 (CAKO A/S, Glostrup, Denmark Catalog # M763). (FIG. 2, top panel.) However, in repeated assays these antibodies were not as potent IgE inhibitors as MHM6 (data not shown). By contrast, the other primate anti-CD23 monoclonal antibodies (5E8 and 6G5) were found to compete with each other and did not complete with MHM6. (FIG. 2, middle and bottom panels.) Moreover, the primate anti-human CD23 monoclonal antibody 5E8 was found to be a potent inhibitor of IL-4 induced IgE in the in vitro assay. (See FIGS. 1 and 3.)

Modified Hu-SCID-Mouse Model for Human IgE Synthesis and Measuring the Inhibition of IL-4 Induced IgE Production by Anti-CD23 Antibodies In Vivo A modified hu-PBMC-SCID mouse model was also developed to detect the effect of the subject antibodies on induced human IgE production in vivo. PBMCs obtained from two donors were cultured with IL-4 in vitro for two days. PBMCs were pooled and used to reconstitute groups of C.B.-17 SCID mice with and without antibodies. Mice were bled on day 14, 21, 28 and 35 and serum IgG and IgE levels were determined by ELISA. This in vivo model was used to assay primate and two different versions of PRIMATIZED® antibodies to CD23 for their ability to inhibit the production of IgE.

A modified SCID mouse model was used because it is known that severe combined immunodeficiency scid/scid (SCID) mice, C.B.-17 (Bosma et al., *Nature*, 301:527 (1983)) reconstituted with human peripheral blood mononuclear cells (hu-PBMC-SCID) can produce significant quantities of human immunoglobulins (Ig) (Mosier et al., *Nature*, 335:256 (1988); Mosier et al., *J. Clin. Immunol.*, 10:185 (1990); Abedi et al.,*J. Immunol.*, 22:823 (1992); and Mazingue et al., *Eur. J. Immunol.*, 21:1763 (1991).) The predominant isotype of human immunoglobulin (Ig) produced in hu-PBMC-SCID mice is IgG. Generally, IgM, IgA and IgE isotypes are found in very low or non-detectable levels except in cases where PBMC is obtained from donors with certain autoimmune or allergic disease conditions. It has also been reported that manipulation of hu-PBMC SCID mouse model with certain cytokines may be provided for the generation of significant levels of non-IgG iso-types, including IgE (Kilchherr et al., *Cellular Immunology*, 151:241 (1993); Spiegelberg et al., *J. Clin. Investigation*, 93:711 (1994); and Carballido et al.,*J. Immunol.*, 155:4162 (1995)). The hu-PBMC-SCIDs, has been also used to generate antigen specific Ig provided the donor has been primed for the antigen in vivo.

Therefore, the aim of the present inventors was focused on establishing a suitable human IgE producing hu-PBMC-SCID mouse model that could be used to test the efficacy of therapeutic for treatment of IgE related diseases such as allergic disorders, including the subject anti-CD23 antibodies.

Materials and Methods

The following materials and methods were used in the hu-PBMC-SCID mouse model described below.

SCID mice: C.B-17 scid/scid immunodeficient mice were obtained from Taconic (C.B.-17/IcrTac-scidfDF) and maintained in IDEC Pharmaceuticals' animal facility. Mice were housed in sterilized microbarrier units with sterilized bedding. Animal studies were performed in accordance with the "Guide for the Care and Use of Laboratory Animals" specified by the Committee on Care of Laboratory Animal Resources Commission on Life Science-National Research Council (Guide for the Care and Use of Laboratory Animals, DHHS Publ. No. (NIH) 86-23, Bethesda, Md., NIH, 1985).

Human PBMC: PBMCs were isolated from buffy coats obtained from a blood bank by centrifugation through Ficoll-Hypaque (Histopaque-1077) as recommended by the manufacturer (Sigma Diagnostics Catalog # 1077-1). Lymphocyte preparation at the interface of the gradient were harvested and washed three times in Hanks Balanced Salt Solution (HBSS) (Bio-Whittaker Catalog # 10-527F). For each experiment PBMCs were obtained from two separate donors and cultured separately in vitro. PBMCs were resuspended at $1-3 \times 10^6$ cells/ml concentration in HB-Basal medium plus 1% HB101 lyophilized supplement (Irvine Scientific Catalog # T000 & T151) containing 5% FCS plus 1000 IU/ml of IL-4 (Genzyme, Inc. Catalog # 2181-01) and incubated for 48 hours at 37° C. with 5% $CO_2$. After incubation, the cells from different buffy coats were harvested, pooled and used to reconstitute SCID mice.

In Vivo Assay Conditions

Groups of mice (four to five per group) were injected with fifty-sixty×$10^6$ lymphocytes in 200–300 μl volume of HBSS intraperitoneally (i.p.) on day zero. For the groups that received anti-CD23 antibody, on day zero, PBMCs were mixed with anti-CD23 antibody (200 to 400 μg/mouse) before i.p., injection and the second injection was given on day seven. All mice received 5000 IU per mouse of IL-4 i.p., between day zero to day five. A group which was not injected with antibody served as the control group. Mice were bled from a retro-orbital vein and the serum was analyzed for IgG and IgE on days fourteen, twenty-one, twenty-eight and thirty-five by ELISA.

FIG. 8 shows that the primate anti-human CD23 monoclonal antibody 5E8 is effective in inhibiting IL-4 induced IgE production in vivo in the SCID mouse model.

Cloning and Expression of PRIMATIZED® Anti-human CD23 Monoclonal Antibodies

In order to clone primate immunoglobulin variable domains, Poly A+ RNA was separately isolated from approximately $2 \times 10^6$ cells from the primate heterohybridomas secreting the anti-human CD23 monoclonal antibodies 6G5 and 5E8 by using the Micro-FastTrack MRNA isolation Kit (Invitrogen Catalog # K1520-02) according to methods set forth by the manufacturer.

The first strand of cDNA was synthesized from the poly A+ RNA by using the cDNA Cycle Kit (Invitrogen Catalog # L1310-01) according to conventional methods.

The light and heavy chain variable regions of 6G5 and 5E8 were then isolated by PCR from cDNA using PCR primers that were selected based upon different consensus families of human immunoglobulins. 5' primers were selected which corresponded to the beginning of the leader sequences of the light and heavy variable region and 3' primers were selected which corresponded to the J region (The specific primers used to PCR amplify the lambda light chain variable domain of 6G5, the kappa light chain variable domains of 5E8, and the heavy chain variable domains of 6G5 and 5E8 are set forth in Tables 1–3). PCR was performed according to standard methods (30 cycles with 1 minute at 94° C., 1.5 minutes at 54° C. and 2 minutes at 72° C. in a Hot start 100 tube (Gibco BRL Catalog # 10332-013). PCR was set up in 50 μl reactions containing 5 μl out of 80 μl cDNA (from $2 \times 10^6$ cells) as a template, 2 μl of 5 nM dNTP, 1 μl of Taq polymerase, 5 μl of Taq polymerase buffer, 2 μl of the 5' primer (25 pmoles/μl), 2 μl of the 3' primer (25 pmoles/μl), and 36 μl of water. (Taq polymerase and buffer were obtained from Stratagene Catalog # 600131, dNTP from Boehringer Mannheim Catalog #1581295.)

A) Construction of the Plasmids N5LG1+6G5 and N5LG4P+6G5

1) Cloning the Light Chain Variable Domain of Primate Monoclonal Anti-human CD23 Antibody 6G5 by PCR The first PCR amplification of the light chain variable region from the cDNA of primate monoclonal antibody 6G5 showed bands which were consistent in situ with the lambda light chain variable region. These bands appeared in all reactions using the three different early leader sequence primers. (See Tables 1–3.) However, the PCR product obtained using primer 745 (Family 2) was considered more specific because of the relatively greater intensity of the PCR product band.

This PCR product was isolated using a Qiaquick Gel Extraction Kit (Qiagen Catalog # 28704). The purified PCR fragment was digested with Bgl II and Avr II restriction endonucleases, and ligated into the mammalian expression vector N5LG1 which was digested with the same restriction endonucleases. Twenty microliters of the ligation mixture containing the purified PCR product from one fifty microliter PCR reaction, 100 mg N5LG1 vector, two microliters of 10× ligation buffer (NEB Catalog # 202S) and two microliters of T4 ligase (NEB Catalog # 202S), were then incubated at 14° C. overnight.

The mammalian expression vector N5LG1 contains genetic sequences (e.g., regulatory sequences, coding sequences) which provide for the expression of four separate proteins in a mammalian cell. They are:

(i) a partial immunoglobulin light chain with the human lambda light chain constant region and unique restriction endonuclease sites for inserting light chain variable domains;

(ii) a partial immunoglobulin heavy chain with the and human gamma 1 chain constant region coding sequences and unique restriction endonuclease sites for inserting heavy chain variable domains;

(iii) a neomycin phosphotransferase gene used to select for cells that have incorporated the plasmid and are resistant to the antibiotic Geneticin (Gibco BRL Catalog # 10131-1209); and (iv) a murine dihydrofolate reductase gene (DHFR) which provides for the selection and genomic amplification when cells are cultured in the presence of methotrexate (MTX, Sigma Catalog # A-6770) (Reff et al., *Blood*, 83:433–445 (1994).

After ligation, the mixture was digested using Pme I restriction endonuclease, which digests the parent N5LG1 plasmid, but not the N5LG1 plasmid which has been ligated to the light variable domain of 6G5. After digestion, the mixture was transformed into Epicurian coli® XL1-Blue competent cells (Stratagene Catalog # 200249) as follows.

One hundred microliters of competent cells were mixed with 10 μl of the above ligation mixture, set on ice for 30 minutes, then heated at 45° C. for 30 seconds. This mixture was placed on ice for 2 minutes, and 900 μl of SOC, prewarmed to room temperature, was then added. (SOC is LB broth Gibco BRL Catalog # 10855-013, plus 0.02 M MgCl₂, 0.02 M MgSO₄ and 0.02 M D-glucose.) After incubation at 37° C. for an hour, the mixture was centrifuged at 4000 g for a minute, and 800 μl of supernatant discarded. The rest of the mixture was plated onto a LB agar (Gibco BRL Catalog # 12945-044) dish containing 50 μg/ml ampicillin (Amp, Gibco BRL Catalog # 13075-015). Plasmid DNA was isolated from individual colonies of *E. coli* that grew on the Amp plate by using the Wizard® Miniprep DNA purification system (Promega Catalog # A7510).

The isolated plasmid DNA was then characterized by digestion with Bgl II and Avr II followed by agarose gel electrophoresis. An ethidium stained DNA band of 400 bp was indicative of a potential successful cloning of a light chain variable domain.

To confirm this was an immunoglobulin light chain variable domain, sequencing was done using the Sequenase 7-Deaza -dGTP DNA Sequencing Kit (USB catalog # 70990) with sequencing primers 607 and GE 108. (See Sequencing Primers in Table 4.)

A second independent PCR amplification of the light chain from cDNA of primate monoclonal antibody 6G5 was effected using a 5' primer early leader sequence of lambda light chain family 2 (primer 745) (SEQ ID NO: 15) and the 3' J region primer 926 (SEQ ID No: 17. (See Primers for PCR of the lambda light chain variable domain of 6G5 in Tables 1–3 (SEQ ID NOs: 9–25). The isolated PCR product (see technique above) was cloned into TA vector by using the Original TA Cloning(Kit (Invitrogen Catalog # K2000-01). The isolated mjniprep DNA (see technique above) was examined under agarose gel electrophoresis after digestion with EcoR I restriction endonuclease. The resultant PCR product comprised in the TA vector was then sequenced (as described previously) using Sp6 (SEQ ID NO: 26) and M13(−40) (SEQ ID NO: 27) forward primers (See Sequencing primers in Table 4 (SEQ ID NOs: 26–35)). The resultant light chain sequence was identical to that of light chain from the first PCR. This entire sequence of the light chain variable domain of primate monoclonal anti-human CD23 antibody 6G5 is presented below as an alignment of the nucleotide sequence (SEQ ID NO:1) and the encoded amino acid sequence (SEQ ID NO:2).

Light Chain Variable Region of Primate
Monoclonal Antibody Anti-human CD23 6G5
Leader

```
Met Ala Trp Thr Leu Leu Leu Val Thr Leu Leu Thr
ATG GCC TGG ACT CTG CTC CTC GTC ACC CTC CTC ACT

-1
Gln Gly Thr Gly Ser Trp Ala
CAG GGC ACA GGA TCC TGG GCT (SEQ ID NO: 1 - bases
1-57)
```

Mature Protein Numbering is Kabat

Framework 1

```
 1                                9  11
Gln Ser Ala Pro Thr Gln Pro Pro Ser Val Ser Gly
CAG TCT GCC CCG ACT CAG CCT CCC TCT GTG TCT GGG
```

```
                20               23
Ser Pro Gly Gln Ser Val Thr Ile Ser Cys
TCT CCT GGA CAG TCG GTC ACC ATC TCC TGC (SEQ ID
NO: 1 - bases 58-123)
```

CDR 1

```
 24            27 27A 27B 27C 28
Thr Gly Thr Ser Asp Asp Val Gly Gly Tyr Asn Tyr
ACT GGA ACC AGC GAT GAC GTT GGT GGT TAT AAC TAT

34
Val Ser
GTC TCC (SEQ ID NO: 1 - bases 124-165)
```

Framework 2

```
 35                   40
Trp Tyr Gln His His Pro Gly Lys Ala Pro Lys Leu
TGG TAC CAA CAC CAC CCA GGC AAA GCC CCC AAA CTC

49
Met Ile Tyr
ATG ATT TAT (SEQ ID NO: 1 - bases 166-210)
```

CDR2

```
 50                        56
Asp Val Ala Lys Arg Ala Ser
GAT GTC GCT AAG CGG GCC TCA (SEQ ID NO: 1 - bases
211-231)
```

Framework 3

```
 57         60
Gly Val Ser Asp Arg Phe Ser Gly Ser Lys Ser Gly
GGG GTC TCT GAT CGC TTC TCT GGC TCC AAG TCT GGC 70                                      80
Asn Thr Ala Ser Leu Thr Ile Ser Gly Leu Gln Ala
AAC ACG GCC TCC CTG ACC ATC TCT GGG CTC CAG GCT

88
Glu Asp Glu Ala Asp Tyr Tyr Cys
GAG GAG GAG GCT GAT TAT TAC TGT (SEQ ID NO: 1 -
bases 232-327)
```

CDR 3

```
 89  90                   95 95A  96 97
Cys Ser Tyr Thr Thr Ser Ser Thr Leu Leu
TGT TCA TAT ACA ACC AGT AGC ACT TTG TTA (SEQ ID
NO: 1 - bases 328-357)
```

Framework 4

```
 98      100                   106 106A 107
Phe Gly Arg Gly Thr Arg Leu Thr Val Leu Gly
TTC GGA AGA GGG ACC CGG TTG ACC GTC CTA GGT (SEQ
ID NO: 1 - bases 358-390)
```

2) Cloning the Heavy Chain Variable Domain of Primate Monoclonal Anti-human CD23 Antibody 6G5 by PCR The first PCR amplification of the heavy chain variable domain from cDNA of primate monoclonal antibody 6G5 was performer by using the set of early leader sequence primers described supra and the 3' J region primer GE244 (SEQ ID NO: 23). These primers are in Tables 1–3 (SEQ ID NOs: 9–25) infra. This reaction resulted in a 350 base PCR product. This 350 base product (purified as described supra), was digested with Nhe I and Sal I, and ligated into N5LG1 and digested with the same endonucleases in the first PCR amplification. The resultant ligation mixture was transformed into host cells using the same techniques for cloning the light chain. Plasmid N5LG1 containing the 350 base PCR product was then isolated and sequenced (using sequencing primers 266 (SEQ ID NO: 32) and 268) (SEQ ID NO: 33). (These Sequencing primers are set forth in Table 4 (SEQ ID NOs: 26–35).)

Sequencing revealed that the PCR product contained only part of the heavy variable domain and comprised a deletion in its amino terminus (Sequence began at frame-work 2, codon 36).

A second independent PCR reaction was conducted to amplify and isolate the heavy chain variable domain of primate monoclonal antibody 6G5 using a 5' early leader sequence primer for family 1 (MB1503) (SEQ ID NO: 18) and a 3' J' region primer GE244 (SEQ ID NO: 23). (These primers are also contained in Tables 1–3 (SEQ ID NOs: 9–25)) The resultant PCR product was then cloned into the NSLG1 using the same techniques described supra. Its sequence was found to be identical to the first PCR product.

Therefore, in order to clone the whole heavy variable domain of 6G5 including the missing 5' terminus a new longer 3' primer (MB 1533) (SEQ ID NO: 25) which included the CDR3 and framework 4 regions of the 6G5 heavy variable chain was then used in a third independent PCR reaction with the family 1 5' primer (MB1503) (SEQ ID NO: 18). (These primers are also contained in Tables 1–3 (SEQ ID NOs: 9–25).)

After PCR, a larger 420 base PCR product was observed on the agarose gel. This PCR product was isolated as described previously, and cloned into a TA vector. The resultant PCR product contained in the TA vector was then sequenced. Sequencing revealed that this DNA contained the whole heavy variable domain and that the 3' part was identical to that of previously cloned partial heavy chain variable domain from the first two PCR reactions.

A fourth independent PCR was performed using the same primers as the third PCR amplification. This resulted in a PCR product which was isolated and cloned into the TA vector as described previously. The sequence of the fourth independent PCR product was found to be identical to that obtained in the third PCR amplification. This sequence, which comprises the heavy chain variable domain of primate monoclonal anti-human CD23 antibody 6G5, is presented below as an alignment of the nucleotide sequence (SEQ ID NO: 3) and the encoded amino acid sequence (SEQ ID NO:4).

Heavy Chain Variable Region of Primate
Monoclonal Antibody Anti-human CD23 6G5

Leader

Met Lys His Leu Trp Phe Phe Leu Leu Leu Val Ala
ATG AAA CAC CTG TGG TTC TTC CTC CTC CTG GTG GCA

-1
Ala Pro Arg Trp Val Leu Ser

-continued
GCT CCC AGA TGG GTC CTG TCC (SEQ ID NO: 3 - bases 1–57)

Mature Protein (Numbering is Kabat)

Framework 1

1                                           10
Gln Leu Gln Leu Gln Glu Ser Gly Pro Gly Val Val
CAG CTG CAG CTG CAG GAG TCG GGC CCA GGA GTG GTG

20
Lys Pro Ser Glu Thr Leu Ser Leu Thr Cys Ala Val
AAG CCT TCG GAG ACC CTG TCC CTC ACC TGC GCT GTC

30
Ser Gly Gly Ser Val Ser
TCT GGT GGC TCT GTC AGC (SEQ ID NO: 3 - 58–147)

CDR 1

31              35 35a
Ser Ser Asn Trp Trp Thr
AGT AGT AAC TGG TGG ACC (SEQ ID NO: 3 - bases 148–165)

Framework 2

36                  40
Trp Ile Arg Gln Pro Pro Gly Lys Gly Leu Glu Trp
TGG ATC CGC CAG CCC CCA GGG AAG GGA CTG GAG TGG

49
Ile Gly
ATT GGA (SEQ ID NO: 3 - bases 166–207)

CDR2

50      52 52A 53                                   60
Arg Ile Ser Gly Ser Gly Gly Ala Thr Asn Tyr Asn
CGT ATC TCT GGT AGT GGT GGG GCC ACC AAC TAC AAC

65
Pro Ser Leu Lys Ser
CCG TCC CTC AAG AGT (SEQ ID NO: 3 - bases 208–258)

Framework 3

66              70
Arg Val Ile Ile Ser Gln Asp Thr Ser Lys Asn Gln
CGA GTC ATC ATT TCA CAA GAC ACG TCC AAG AAC CAG 80      82 82a 82b 82c 83
Phe Ser Leu Asn Leu Asn Ser Val Thr Ala Ala Asp
TTC TCC CTG AAC CTG AAC TCT GTG ACC GCC GCG GAC 90          94
Thr Ala Val Tyr Tyr Cys Ala Arg
ACG GCC GTG TAT TAC TGT GCC AGA (SEQ ID NO: 3 - bases 259–354)

CDR 3

```
95                      100 100a 100b 100c 100d 101
Asp Trp Ala Gln Ile Ala Gly Thr  Thr  Leu  Gly
GAT TGG GCC CAA ATA GCT GGA ACA  ACG  CTA  GGC

102
Phe
TTC (SEQ ID NO: 3 - bases 355-390)
```

Framework 4

```
103                           110         113
Trp Gly Gln Gly Val Leu Val Thr Val Ser Ser
TGG GGC CAG GGA GTC CTG GTC ACC GTC TCC TCA (SEQ
ID NO: 3 - bases 391-423)
```

3) Construction of Mammalian Expression Vectors

In order to insert the cloned heavy chain variable domains of 6G5 into a mammalian expression vector, the heavy chain variable domain in the TA vector (obtained in the 3rd independent PCR) was digested with Nhe I and Sal I and cloned into the N5LG1 vector which was digested with the same restriction enzymes and which vector already contains the light chain variable domain. The resultant mammalian expression vector was named N5LG1+6G5.

To construct the N5LG4P+6G5 vector, both the light and heavy chain variable domains were isolated from N5LG1+6G5 by digestion of Bgl II and Avr II, and Nhe I and Sal I respectively. The mammalian expression vector N5LG4P vector is identical to the N5LG1 vector described above, except the human gamma 1 was replaced with a human gamma 4 constant region containing a mutation of a serine to a proline in the hinge region to increase stability of the immunoglobulin and improve pharmacokinetics in vivo ("P" mutation). The light chain variable domain was cloned in the plasmid first and the heavy chain variable domain was cloned into the vector containing the light chain variable domain using techniques previously described. This mammalian expression vector was named N5LG4P+6G5.

B. Construction of the Plasmids N5KG4P+5E8, N5KG1+5E8, N5KG4P+5E8N-, and N5KG1+5E8N-

1. Cloning the Light Chain Variable Domain of Primate Monoclonal Anti-human CD23 Antibody 5E8 by PCR The first PCR reaction of the light chain variable domain from FEE cDNA was carried out using a set of kappa early leader sequence primers and the 3' J region primer GE204 (SEQ ID NO: 13). (See primers for PCR of the kappa light chain variable domain of 5E8 in Tables 1–3 (SEQ ID NOs: 9–25)). A 420 base PCR product was obtained. The isolated 420 base PCR product was digested with Bgl II and BsiW I restriction endonucleases, cloned into the mammalian expression vector N5KG4P and sequenced using GE108 (SEQ ID NO: 29) and 377 (SEQ ID NO: 30) primers (which are contained in Table 4 (SEQ ID NOs: 26–35)): The mammalian expression vector N5KG4P is identical to the vector N5LG4P except it contains the human kappa light chain constant region is place of the human lambda light chain constant region. Sequencing of this 420 polynucleotide DNA revealed that it contains the entire kappa light chain variable domain.

A second independent PCR of the light chain variable region was performed using the 5' family 1 primer GE201 (SEQ ID NO: 9) and the 3' primer GE204 (SEQ ID NO: 13). (See primers for PCR of the kappa light chain variable domain of 5E8 in Tables 1–3 (SEQ ID NOs: 9–25)). The isolated PCR product was cloned into the TA vector (using methods previously described) and sequenced using Sp6 (SEQ ID NO: 26) and T7 promoter (SEQ ID NOs: 28) primers. Sequencing revealed that this PCR product was identical to that obtained from the first PCR. The entire sequence of the light chain variable domain of primate monoclonal anti-human CD23 antibody 5E8 is presented below, as an alignment of the nucleotide sequence (SEQ ID NO: 5) and the encoded amino acid seauence (SEQ ID NO:6).

Light Chain Variable Region of Primate Monoclonal Antibody Anti-human CD23 5E8

Leader

```
Met Asp Met Arg Val Pro Ala Gln Leu Leu Gly Leu
ATG GAC ATG AGG GTC CCC GCT CAG CTC CTG GGG CTC

-1
Leu Leu Leu Trp Leu Pro Gly Ala Arg Cys
CTT CTG CTC TGG CTC CCA GGT GCC AGA TGT (SEQ ID
NO: 5 - bases 1-66)
```

Mature Protein Numbering is Kabat

Framework 1

```
1                                          10
Asp Ile Gln Met Thr Gln Ser Pro Ser Ser Leu Ser
GAC ATC CAG ATG ACC CAG TCT CCA TCT TCC CTG TCT 20          23
Ala Ser Val Gly Asp Arg Val Thr Ile Thr Cys
GCA TCT GTA GGG GAC AGA GTC ACC ATC ACT TGC (SEQ
ID NO: 5 - bases 67-135)
```

CDR 1

```
24                          30                  34
Arg Ala Ser Gln Asp Ile Arg Tyr Tyr Leu Asn
AGG GCA AGT CAG GAC ATT AGG TAT TAT TTA AAT (SEQ
ID NO: 5 - bases 136-168)
```

Framework 2

```
35                      40
Trp Tyr Gln Gln Lys Pro Gly Lys Ala Pro Lys Leu
TGG TAT CAG CAG AAA CCA GGA AAA GCT CCT AAG CTC

49
Leu Ile Tyr
CTG ATC TAT (SEQ ID NO: 5 - bases 169-213)
```

CDR2

```
50                                  56
Val Ala Ser Ser Leu Gln Ser
GTT GCA TCC AGT TTG CAA AGT (SEQ ID NO: 5 - bases
214-234)
```

Framework 3

```
57          60
Gly Val Pro Ser Arg Phe Ser Gly Ser Gly Ser Gly
GGG GTC CCA TCA AGG TTC AGC GGC AGT GGA TCT GGG
```

-continued

```
                70                          80
Thr Glu Phe Thr Leu Thr Val Ser Ser Leu Gln Pro
ACA GAG TTC ACT CTC ACC GTC AGC AGC CTG CAG CCT

88
Glu Asp Phe Ala Thr Tyr Tyr Cys
GAA GAT TTT GCG ACT TAT TAC TGT  (SEQ ID NO: 5 -
bases 235-330)
```

CDR 3

```
89  90                              97
Leu Gln Val Tyr Ser Thr Pro Arg Thr
CTA CAG GTT TAT AGT ACC CCT CGG ACG  (SEQ ID NO:
5 - bases 331-357)
```

Framework 4

```
98      100                     107
Phe Gly Gln Gly Thr Lys Val Glu Ile Lys
TTC GGC CAA GGG ACC AAG GTG GAA ATC AAA  (SEQ ID NO:
5 - bases 358-387)
```

2) Cloning the Heavy Chain Variable Domain of Primate Monoclonal Anti-human CD23 Antibody 5E8 by PCR The first PCR of the heavy chain variable domain of 5E8 was performed using a set of 5' early leader heavy chain sequence primers and the 3' primer GE210 (SEQ ID NO: 24). (See primers for PCR of the heavy chain variable domain of 6G5 and 5E8 in Table 1 (SEQ ID NOs: 9–13)). A 420 base PCR product appeared in the family 3 primer reaction. The PCR product was purified and then digested with Nhe I and Sal I and cloned into the mammalian expression vector N5KG4P vector (as described previously). The PCR product was sequenced using the 268 (SEQ ID NO: 33) and 928 (SEQ ID NO: 35) primers. (See sequencing primers in Table 4 (SEQ ID NOs: 26–35).)

A second independent PCR of the heavy chain variable domain of 5E8 was performed using the family 3 5' primer GE207 (SEQ ID NO: 20) and the 3' primer GE210 (SEQ ID NO: 24). (See primers for PCR of the, heavy chain variable domain of 6G5 and 5E8 in Tables 1–3 (SEQ ID NOs: 9–25)). The isolated PCR product was cloned into a TA vector using the same techniques previously described and sequenced by using Sp6 (SEQ ID NO: 26) and T7 (SEQ ID NO: 28) primers. Sequencing revealed that the TAC at codon 91 had been changed into TGC.

In order to determine the appropriate codon at 91, a third independent PCR was performed using the same primers as the second PCR (see above). The PCR product was again cloned into a TA vector and sequenced using Sp6 (SEQ ID NO: 26) and T7 (SEQ ID NO: 28) primers. The sequence was found to be identical to the heavy chain variable sequence obtained in the first PCR. Therefore, the TGC at position 91 in the second independent PCR product is apparently the result of an error introduced during PCR. This entire sequence of the heavy chain variable domain of primate monoclonal anti-human CD23 antibody 6G5 is presented below, as an alignment of the nucleotide sequence (SEQ ID NO: 7) and the encoded amino acid sequence (SEQ ID NO:8).

Heavy Chain Variable Region of Primate Monoclonal Antibody Anti-human CD23 5E8

Leader

```
Met Glu Phe Gly Leu Ser Trp Val Phe Leu Val Pro
ATG GAG TTT GGG CTG AGC TGG GTT TTC CTT GTT CCT

-1
Leu Leu Lys Gly Val Gln Cys
CTT TTG AAA GGT GTC CAG TGT  (SEQ ID NO: 7 - bases
1-57)
```

Mature Protein Numbering is Kabat

Framework 1

```
  1                                      10
Glu Val Gln Leu Val Glu Ser Gly Gly Gly Leu Ala
GAG GTG CAG CTG GTG GAG TCT GGG GGC GGC TTG GCA

20
Lys Pro Gly Gly Ser Leu Arg Leu Ser Cys Ala Ala
AAG CCT GGG GGG TCC CTG AGA CTC TCC TGC GCA GCC

30
Ser Gly Phe Arg Phe Thr
TCC GGG TTC AGG TTC ACC  (SEQ ID NO: 7 - bases
58-147)
```

CDR 1

```
 31          35 35a 35b
Phe Asn Asn Tyr Tyr Met Asp
TTC AAT AAC TAC TAC ATG GAC  (SEQ ID NO: 7 - bases
148-168)
```

Framework 2

```
 36                    40
Trp Val Arg Gln Ala Pro Gly Gln Gly Leu Glu Trp
TGG GTC CGC CAC GCA CCA GGG CAG GGG CTG GAG TGG

49
Val Ser
GTC TCA  (SEQ ID NO: 7 - bases 169-210)
```

CDR2

```
 50      52 52A 53                            60
Arg Ile Ser Ser Ser Gly Asp Pro Thr Trp Tyr Ala
CGT ATT AGT AGT AGT GGT GAT CCC ACA TGG TAC GCA

65
Asp Ser Val Lys Gly
GAC TCC GTG AAG GGC  (SEQ ID NO: 7 - bases
211-261)
```

Framework 3

```
 66              70
Arg Phe Thr Ile Ser Arg Glu Asn Ala Asn Asn Thr
AGA TTC ACC ATC TCC AGA GAG AAC GCC AAC AAC ACA 80      82 82a 82b 82c 83
Leu Phe Leu Gln Met Asn Ser Leu Arg Ala Glu Asp
CTG TTT CTT CAA ATG AAC AGC CTG AGA GCT GAG GAC
```

-continued

```
              90                  94
Thr Ala Val Tyr Tyr Cys Ala Ser
ACG GCT GTC TAT TAC TGT GCG AGC  (SEQ ID NO: 7 -
bases 262-357)
```

CDR 3

```
 95                      100 101
Leu Thr Thr Gly Ser Asp Ser

TTG ACT ACA GGG TCT GAC TCC  (SEQ ID NO: 7 -
bases 358-378)
```

Framework 4

```
103                      110          113
Trp Gly Gln Gly Val Leu Val Thr Val Ser Ser

TGG GGC CAG GGA GTC CTG GTC ACC GTC TCC TCA  (SEQ
ID NO: 7 - bases 379-411)
```

3) Construction of Mammalian Expression Vectors

The heavy variable domain in N5KG4P was digested with Nhe I and Sal I, purified, and cloned into N5KG4P which contains the light chain variable domain of 5E8. This plasmid was then digested with the restriction endonucleases as previously described. This resulted in a vector containing both the light and heavy variable domain of 5E8. This vector was named N5KG4P+5E8. The heavy and light variable domains of N5KG4P+5E8 were then both inserted into the mammalian expression vector N5KG1 to create the N5KG1+5E8 vector.

4) Alteration of an Amino Acid in the Heavy Chain Variable Region of Primate Monoclonal Antibody 5E8 by Site Specific Mutagenesis and Construction of Mammalian Expression Vectors Based upon the sequence of 5E8 heavy variable domain, there is a potential glycosylation site of the immunoglobulin at asparagine codon 75. This potential glycosylation site corresponds to a conserved asparagine-linked glycosylation motif having the following tripeptide sequence: (Asn)—(Any amino acid except proline)—(Serine or threonine). Therefore, a glycosylation mutant of 5E8, which would be unable to be glycosylated at this position because of modification of this glycosylation motif, was generated by replacing the asparagine codon 75 with a lysine (which is found in many human immunoglobulins at this position). Site specific mutagenesis was effected by the following methods.

A first PCR was done using N5KG4P+5E8 as a template and a 3' primer (corresponding to codon 71 to 79) and which contains a mutation at codon 75 (AAC changed to AAG, Primer MB1654 (SEQ ID NO: 39), and a 5' primer at the beginning of the leader sequence (Primer MB1650) (SEQ ID NO: 36). (See PCR Primers Used for the Generation of a Glycosylation Mutant of the Heavy Chain Variable Region 5E8 set forth in Table 5 (SEQ ID NOs: 36–39)).

A second PCR was performed on the same template by using a 5' primer (corresponding to codon 71 to 79) containing the same mutation (Primer MB1653) (SEQ ID NO: 38) and a 3' primer from the end of framework 4 (Primer MB1651) (SEQ ID NO: 37) (See PCR Primers Used for the Generation of a Glycosylation Mutant of the Heavy Chain Variable Region of 5E8 in Table 5 (SEQ ID NOs: 36–39).)

These two PCR products were isolated and mixed in equal molar ratios. A third independent PCR was then carried out by using the mixture of the first and second PCP products as a template with a 5' primer used in the first PCR (MB1650) (SEQ ID NO: 36) and a 3' primer used in the second PCR (MP 1651) (SEQ ID NO: 37) (See PCP Primers Used for the Generation of a Glycosylation Mutant of the Heavy Chain Variable Region in Table 5 (SEQ ID NOs: 36–39).) The PCR product obtained in third PCR was found to contain the heavy variable domain coding region of 5E8 wherein the asparagine 75 had been changed to lysine.

The third PCR product was purified, digested with restriction endonucleases Sal I and Nhe I, and cloned into the N5KG4P containing the light variable domain only. The PCR product was sequenced to confirm that it comprised the mutant heavy variable domain. This mammalian expression plasmid was named N5KG4P+5E8N-.

To construct of N5KG1+5E8N-, both light and heavy variable domains from N5KG4P-5E8N- were digested with Bgl II and BsiW I, and Nhe I and Sal I respectively. The light variable domain was cloned first and then the heavy variable domain was inserted into the mammalian expression plasmid N5KG1, to create the plasmid N5KG1+5E8N-.

TABLE 1

Primers for PCR of the kappa light chain variable domain of 5E8

| NAME | Light chain Vk —early leader 5' (Bgl II) | | | FAMILY |
|---|---|---|---|---|
| | -22 -21 -20 -19 -18 | 17 -16 | -15 -14 | |
| GE201 | 5' AT CAC <u>AGA TCT</u> CTC ACC ATG GAC ATG AGG GTC (SEQ ID NO: 9) | CCC GCT | CAG    3' | 1 |
| GE200 | 5' AT CAC <u>AGA TCT</u> CTC ACC    ATG AGG CTC (SEQ ID NO: 10) | CCT GCT | CAG    3' | 2 |
| GE202 | 5' AT CAC <u>AGA TCT</u> CTC ACC    ATG GAA (A/G)CC (SEQ ID NO: 11) | CCA GC(T/G) | CAG    3' | 3 |
| GE203 | 5' AT CAC <u>AGA TCT</u> CTC ACC    ATG GTG TTG (SEQ ID NO: 12) | CAG ACC | CAG GTC 3' | 4 |

TABLE 1-continued

Primers for PCR of the kappa light chain variable domain of 5E8

Light chain Vk-3' primer (BsiW I)

```
            113 112 111 110 109 108 107 106  105  104 103
GE204  5' GG TGC AGC CAC CGT AGC TTT GAT (C/T)TC CA(G/C) CTT 3'
       (SEQ ID NO: 13)
```

TABLE 2

Primers for PCR of the lambda light chain variable domain of 6G5

| NAME | Light chain Vl —early leader 5' (Bgl II) | FAMILY |

```
                -20  -19  -18    -17    -16   -15
744  5' AT CAC AGA TCT CTC ACC ATG (G/A)CC TG(G/C) TCC    CCT    CT 3'   1
     (SEQ ID NO: 14)
                                                    25
745  5' AT CAC AGA TCT CTC ACC ATG GCC     TGG    (A/G)CT C(T/C)G CT 3'   2
     (SEQ ID NO: 15)

910  5' AT CAC AGA TCT CTC ACC ATG GC(A/C) TGG    A(T/C)C CCT    CTC 3'   3
     (SEQ ID NO: 16)
```

Light chain Vl-3' primer (Avr II)

```
              110 109 108 107 106 105 104
926  5' (AC)10 CTT GGG CTG ACC TAG GAC GGT  3'
     (SEQ ID NO: 17)
```

TABLE 3

Primers for PCR of the heavy chain variable domains from 6G5 and 5E8

| NAME | Heavy chain-early leaders 5' (Sal I) | Family |

```
                     -20 -19 -18 -17 -16 -15
MB1503 5' GCG ACT AAG TCG ACC ATG GAC TGG ACC TGG    3'              1
       (SEQ ID NO: 18)

MB1502 5' GCG ACT AAG TCG ACC ATG AAA CAC CTG TGG    3'              2,4
       (SEQ ID NO: 19)

GE207  5' GCG ACT AAG TCG ACC ATG GAG TTT GGG CTG AGC 3'             3
       (SEQ ID NO: 20)

GE208  5' GCG ACT AAG TCG ACC ATG GGG TCA ACC GCC ATC 3'             5
       (SEQ ID NO: 21)

GE209  5' GCG ACT AAG TCG ACC ATG TCT GTC TCC TTC CTC 3'             6
       (SEQ ID NO: 22)
```

Heavy chain-3' primer (Nhe I)

```
                120 119 118 117 116 115 114 113 112 111 110
GE244  5' GC CAG GGG GAA GAC CGA TGG GCC CTT GGT GCT AGC TGA GGA GAC GG 3'
       (SEQ ID NO: 23)

GE210  5'                GA TGG GCC CTT GGT GCT AGC TGA GGA GAC GG 3'

(SEQ ID NO: 24)

MB1533 5'                              GGT GCT AGC TGA GGA GAC GGT
                        109 108 107 106 105 104 103 101 100 99
                        GAC CAG GAC TCC CTG GCC CCA GAA GCC TAG 3'
       (SEQ ID NO: 25)
```

TABLE 4

Sequencing Primers

| | | |
|---|---|---|
| Sp6 primer | 5' AT TTA GGT GAC ACT ATA (SEQ ID NO: 26) | 3' |
| M13 (-40) Forward Primer | 5' GTT TTC CCA GTC ACG A (SEQ ID NO: 27) | 3' |
| T7 Promoter Primer | 5' AT ATA CGA CTC ACT ATA GGG (SEQ ID NO: 28) | 3' |
| GE 108 Primer | 5' CCG TCA GAT CGC CTG GAG ACG CCA (SEQ ID NO: 29) | 3' |
| 377 Primer | 5' GCA GTT CCA GAT TTC AAC TG (SEQ ID NO: 30) | 3' |
| 607 PRIMER | 5' CCA GGC CAC TGT CAC GGC TTC (SEQ ID NO: 31) | 3' |
| 266 PRIMER | 5' CAG AGC TGG GTA CGT CCT CA (SEQ ID NO: 32) | 3' |
| 268 PRIMER | 5' GCC CCC AGA GGT GCT CTT GG (SEQ ID NO: 33) | 3' |
| 876 PRIMER | 5' ACA CAG ACC CGT CGA CAT GG (SEQ ID NO: 34) | 3' |
| 928 PRIMER | 5' GCT CTC GGA GGT GCT CCT GG (SEQ ID NO: 35) | 3' |

TABLE 5

PCR Primers Used for the Generation of a
Glycosylation Mutant of the Heavy Chain Variable
Region of 5E8

```
                      Sal I    -20 -19 -18 -17 -16
MB    5' ACA GAC CCG TCG ACC ATG GAG TTT GGG CTG 3'
1650  (SEQ ID NO: 36)

Nhe I
              118 117 116 115 114 113 112 111 110
MB    5' CCC CTT GGT GCT AGC TGA GGA GAC GGT 3'
1651  (SEQ ID NO: 37)

71  72  73  74  75  76  77  78  79
MB    5' AGA GAG AAC GCC AAG AAC ACA CTG TTT 3'
1653  (SEQ ID NO: 38)

79  78  77  76  75  74  73  72  71
MB    5' AAA CAG TGT GTT CTT GGC GTT CTC TCT 3'
1654  (SEQ ID NO: 39)
```

C) Construction of Gamma-3 Vectors

Numerous methods exist for conversion of murine antibodies to chimeras in which the heavy and light chain constant regions are substituted with human versions or in which all but the CDRs (complementary determining regions) are substituted with their human equivalents. (See King et al., Biochem. J. 281:317–23, 1992; Queen et al., Proc. Nat. Acad. Sci. USA 86(24):10029–33, 1989; Love et al., Methods Enzymol. 178:515–27, 1989; Hutzell et al., Cancer Res. 51:181, 1991; Chiang et al., Biotechniques 7(4):360–6, 1989; Heinrich et al., *J. Immunol.* 143:3589, 1989; Hardman et al., Int. J. Cancer 44:424, 1989; Orlandi et al., Proc. Nat. Acad. Sci. USA 86(10):3833–6, 1989).

Further, the previous sections specifically demonstrate that construction of vectors for expression of PRIMATIZED® gamma-1 and gamma-4 antibodies may be accomplished by amplifying the DNA encoding the light and heavy chain variable regions using PCR, and cloning these regions into an expression vector or vectors encoding the appropriate human constant region domains. Thus, it should be clear that similar constructs may be made which encode other human constant region domains, so long as appropriate mammalian expression vectors are available which also contain cloning sites which allow insertion of the amplified variable region DNA from the primate antibodies.

It should also be apparent that the PCR primers used to amplify the variable region DNA may be designed to accommodate various restriction cloning sites depending on the vector used.

Vectors encoding the constant region domain from human IgG3 are available in the art, and may be used for constructing the PRIMATIZED® antibodies of the present invention. For instance, Co et al. have used separate vectors expressing human light and heavy chain constant regions for constructing chimeric and humanized antibodies, and provide heavy chain vectors for both human gamma-1 and gamma-3. For cloning the variable domain regions of the antibody of interest into these vectors, an XbaI restriction site is conveniently located just before the constant regions in the $J_k4$ and the $J_H3$ intronic segments for the light and heavy chains, respectively (Co et al., 1996, Cancer Res. 56: 1118–1125; Co et al., 1992, *J. Immunol.* 148: 1149–1154).

Thus, by designing PCR primers which incorporate XbaI restriction sites, or sites which create the same single stranded overhangs as the XbaI resptriction enzyme (i.e. NheI, SpeI), the variable regions from a primate antibody may be associated with the human gamma-3 constant region domain using the vectors described in Co et al. Alternatively, linkers or adaptors may be used to facilitate cloning.

It is also possible to construct a cDNA version of the human gamma-3 constant region using DNA synthesis techniques and insert it into the N5KG1 vectors described herein in place of the human gamma-1 constant region between the NheI and BamHI sites. Depending on which restriction sites are most convenient for cloning the particular variable region of interest, there are also other gamma-3 vectors which have been described in the art, and any of these may be used to construct and express the gamma-3 antibodies of the present invention. (See, for example, Parren et al., 1992, *J. Immunol.* 148(3): 695–701; Steplewski et al., 1988, Proc. Natl. Acad. Sci. USA 85: 4852–4856; and U.S. Pat. No. 4,975,369, herein incorporated by referenced).

D) Variations of PRIMATIZED® Antibodies

The present invention also encompasses PRIMATIZED® antibodies containing mutations, substitutions or deletions of the constant region. Such mutations may be constructed using site-directed mutagenesis techniques as described above for the glycosylation mutant, which are well-known techniques for those of skill in the art.

The mutated antibodies of the present invention are designed with the purpose of creating a desired change in the level of therapeutic efficiency, i.e. in FcR binding. However, it should be understood that any mutation in the constant region of the antibodies should not alter the basic effector functions as mediated by the gamma-1 or gamma-3 constant region domains. It may also be possible to alter other subclasses of gamma antibodies by mutagenesis such that they have similar effector functions as an antibody containing a gamma-1 or a gamma-3 domain. Such antibodies are also encompassed by the present invention.

For example, the regions of the IgG constant region involved in FcR binding and interaction with the C1q complement component have been characterized, and mutations have been identified which either increase or decrease binding affinity. As disclosed in U.S Pat. No. 5,648,260, herein incorporated by reference, changing Leu 235 to Glu in the human IgG3 constant region destroys the interaction of the mutant for the human Fc gamma Rl receptor. Furthermore, mutations on adjacent or close sites in the hinge link region (i.e. replacing residues 234, 235, 236 or 237 by Ala) indicate that alterations in residues 234, 235, 236 and 237 at least affect affinity for the Fc gamma Rl receptor.

Similarly, in U.S. Pat. No. 5,348,876, also incorporated by reference, it was shown that by decreasing the length of the hinge region of the human IgG3 constant region and altering the amino acid sequence of this region, C1q binding and thus complement mediated cytolysis were further improved. In fact, the variants bound more C1q than wild type IgG3 and much more than IgG1.

Thus, it is clear from the art that mutations may be used to create therapeutic antibodies with decreased affinities for human Fc receptors, perhaps for the treatment of more mild medical conditions. In addition, mutations may be identified which increase effector function activity, thereby leading to stronger versions for therapeutic use. It should be recognized that manipulations of gene sequence to create alterations in drug efficiency are envisioned, and well within the spirit and scope of the present invention.

E) Expression of PRIMATIZED® Antibodies in Chinese Hamster Ovary Cells

In order to isolate the PRIMATIZED® antibodies, the vectors encoding the antibodies were expressed in Chinese Hamster Ovary cells using the following protocol.

A large scale plasmid DNA was purified using the WIZARD® Maxipreps DNA Purification System (Promega Catalog # A7421). The purified DNA was digested with Ssp I and BspLU11 I, precipitated with ethanol once, and resuspended in sterile TE.

Purified, endonuclease restricted plasmid DNA was then introduced into Chinese hamster ovary (CHO) dihydrofolate reductase minus DG44 cells using electroporation. The electroporation technique used is described below.

Approximately $1.6 \times 10^8$ CHO cells were spun in an appropriate size sterile Corning tube for one minute at 1000 RPM. The media was removed and the cells were washed in fifteen milliliters of sterile ice cold SBS (sterile sucrose buffered solution is 272 mM sucrose, 7 mM sodium phosphate pH 7.4, 1 mM $MgCl_2$) and spun for 5 minutes at 1000 RPM. The SBS was removed and cells were suspended using fresh ice cold sterile SBS at a cell concentration of $1 \times 10^7$ cells were per ml and left on ice for 15 minutes. The BTX 600 electroporator was turned on and preset at 230 volts, with the maximum voltage knobs being set at 500 volts/capacitance & resistance. The capacitance was set at 400 microfaradays and the resistance was set at 13 ohms (setting Rl).

Plasmid DNA (4 μg DNA or 2 μg DNA) and 0.4 ml of cells ($4 \times 10^6$ cells) were then placed in BTX 0.4 ml cuvettes (BTX Catalog # 620). The cells were shocked by placing the cuvette into the BTX 600 stand and pressing the automatic charge & pulse button. Approximately 20 separate electroporations were performed with each mammalian expression plasmid.

After shocking, the cuvettes were left at ambient temperature for fifteen minutes. The cells and DNA were from each cuvette were resuspended in 20 ml of CHO-SSFMII containing no hypoxanthine or thymidine (Gibco BRL Catalog # 31033-012) to which HT supplement (100× supplement is 10 mM sodium hypoxanthine, 1.6 mM thymidine Gibco BRL Catalog # 11067-014) had been added. The cells from a single electroporated cuvette were then plated into a 96 well plates (200 μl/well) and placed into a 37° C. $CO_2$ incubator. Selection was started two or three days later by changing the media to the above media with the addition of 400 mg/ml of Geneticin® (G418, Gibco BRL Catalog # 10131-019). The cells were grown at 37° C. and the cell media were changed every 3–5 days. After sixteen days G418 resistant clones appeared in the wells and the supernatant was assayed for antibody expression by ELISA. The highest expressing clones were then expanded individually. Monoclonal antibodies were purified as described below.

Immunoglobulin ELISA

Plates (Immulon 2, Dynatech Laboratories, Inc. Catalog # 011-010-3455) are coated overnight at 4° C. with 200 ng unlabeled goat anti-human IgG antibody at 100 μl/well. This is effected using twenty milliliters of unlabeled goat anti-human IgG/10 mls Coating Buffer/plate (Boehringer Mannheim Ab Catalog # 605 400). (1:500 dilution of ~1 mg/ml stock.) The coating buffer is then removed from the plates and dried using a paper towel. One hundred microliters of a dilution buffer/well is then added.

Antibody solutions and standards (100 ng/ml–2.5 ng/ml) are then added in duplicate at 100 μl/well directly to the 100 ml dilution buffer. The antibody solutions and standards are contained in dilution buffer. The resultant solutions are then incubated for at least 1 hour at 37° C.

After incubation, the contents of each plate are removed and the plates are washed with tap water five times. The plates are then dried on a paper towel.

After drying of the plates, a second antibody is then added at 100 μl/well. This second antibody is either goat anti-human Kappa-HRPO: added at 1/10,000 dilution or 1 μl Ab/10 mls dilution buffer/plate, available from Southern Biotechnology Associates, Inc. Catalog # 2060-05 or a goat anti-human Lambda-HRPO; used at 1/20,000 dilution or 1 μl Ab/20 mls dilution buffer/2 plates (available from Southern Biotechnology Associates, Inc. Catalog # 2070-05).

The antibody and contents of the plate are allowed to incubate for one hour at 37° C. After incubation the contents of each plate are removed. The plates are again washed five time with tap water, and the washed plates are dried. To the dried plates is then added HRPO substrate (TMB Microwell—two component) in an amount of 100 μl/well. (Five milliliters of TMB Peroxidase Substrate+five milliliters of Peroxidase Solution B/plate (Kirdgaard and Perry Labs, TMB Microwell two component reagents Catalog # 50-76-00).

The reaction is stopped by the addition of one hundred microliters of 2M $H_2SO_4$ to each well when the weakest standard (2.5 ng/ml) is visible over background. The optical density of wells in plates is then read using a plate reader, e.g., Molecular Devices Emax precision microplate reader set at wavelength: OD 450 and OPT2 (OD 540).

ELISA BUFFERS

Coating Buffer
    Sodium Carbonate 0.8 gram/liter
    Sodium Bicarbonate 1.55 gram/liter
    Adjust pH to 9.5 with ~1 ml 1N HCl
Dilution Buffer
    0.5% Nonfat Dry Milk in PBS plus 0.01% Thimerosal
    (5 gm/L) (100 mg/L)

Examples of ELISA values obtained using the above-described assay are set forth below.

| Standard | OD 450 | OD450 | Average |
|---|---|---|---|
| 100 ng/ml | 0.805 | 0.876 | 0.841 |
| 50 ng/ml | 0.395 | 0.472 | 0.434 |
| 25 ng/ml | 0.213 | 0.252 | 0.233 |
| 10 ng/ml | 0.089 | 0.105 | 0.097 |
| 5 ng/ml | 0.054 | 0.055 | 0.055 |
| 2.5 ng/ml | 0.031 | 0.035 | 0.033 |
| 0 ng/ml | 0.004 | 0.006 | 0.005 |

Standards in Dilution Buffer

Appropriate dilution of stock AB (sterile filtered in normal saline, protein determination by OD) to give 1 mg/ml Example Chimeric monkey/human anti-CD4 (CE9.1) is 4.18 mg/ml 24 µl of above into 76 µl Dilution Buffer is 1 mg/ml 50 µl Stock Ab (1 mg/ml) into 450 µl Dilution Buffer (D.B.) is 100 µg/ml 50 µl of above mixture into 450 µl D.B. is 10 µg/ml 200 µl of above mixture into 1.8 mls D.B. is 1 µg/ml 1 ml of above mixture into 9 mls D.B. is 100 ng/ml *

5 ml of above mixture into 5 ml D.B. is 50 ng/ml *

5 ml of above mixture into 5 ml D.B. is 25 ng/ml *

4 ml of above mixture into 6 ml D.B. is 10 ng/ml *

5 ml of above mixture into 5 ml D.B. is 5 ng/ml *

5 ml of above mixture into 5 ml D.B. is 2.5 ng/ml *

* Standards used in the ELISA

Antibody purification by Protein A

Procedure

The culture supernatant is centrifuged to remove cells and debris. The centrifuge is then filtered through a 0.2 µm filter. A protein A sepharose Fast flow column (recombinant protein A Sepharose Fast floe) (Pharmacia Biotech Catalog # 71-5000-09) is then prepared and equilibrated using PBS (pH 7.4).

The supernatant is loaded on the column at an appropriate flow rate (e.g., 2 ml/min). After loading, the column is washed with 10 column volume of PBS (pH 7.4). The antibody is eluted from the column using an elution buffer (0.2M acetic acid, 0.1 M glycine pH 3.5) at 1 ml/min flow rate. One milliliter fractions/tube including 100 µl of Tris are then collected. A spectrophotometer absorbance reading is then taken at 280 nm. The antibody fractions are then collected and dialyzed against PBS (pH 7.9) overnight. The dialysate is then sterilized by filtration through a 0.22 µm membrane and stored at −20° C.

Assay Results

The PRIMATIZED® human gamma-4 anti-human CD23 antibodies which are described supra, were purified and assayed for induced IgE inhibitory activity in vitro. These results are contained in FIGS. 3 and 5. This was effected using the in vitro IL-4 IgE assay described supra.

These assay results surprisingly indicated that both human gamma-4 anti-human CD23 antibodies were not as active as the corresponding primate anti-human CD23 antibodies, i.e., they did not significantly inhibit induced IgE production in vitro.

However, because primate 5E8 and p5E8G4P have a potential asparagine linked glycosylation site in the heavy chain variable region, the effects of glycosylation at this site were investigated. (It was found that both these antibodies contain N-linked oligosaccharides at this site. (Data not shown.)) Therefore, in order to prevent glycosylation, the asparagine in the glycosylation site was changed to a lysine in order to eliminate carbohydrate addition. This mutated antibody was named p5E8G4PN-. Assay results demonstrated that this antibody behaved identically to p5E8G4P in the IL-4 IgE assay (see FIG. 3) and also exhibited an identical apparent affinity Kd for human CD23. (See FIG. 4.) Therefore, these results indicated that the difference in IgE inhibition observed from the 5E8 gamma 4 PRIMATIZED® antibody in comparison to primate 5E8 antibody was not attributable to glycosylation differences.

The three primate antibodies (p5E8G4P, p5E8G4PN-, and p6G5G4P) were then expressed as human gamma-1 versions using substantially the same methodology. All three human gamma-1 anti-human CD23 antibodies, respectively designated p5E8G1, p5E8G1N- and p6G5G1, were found to be active in the in vitro IL-4/IgE assay (FIGS. 3 and 5).

p5E8G1 was found to be statistically more suppressive than p5E8G4P at a concentration of 0.3 µg/ml (P[T,t] one tail+0.0055) and at 3 µg/ml (p[T<t] one tail+0.0019). In addition, p5E8G1N- is statistically more suppressive than p5E8G4PN- at both 0.3 µg/ml (p[T<t] one tail+0.0392) and at 3 µg/ml (p[T<t] one tail+0.0310) (FIG. 3).

Similarly, p6G5G1 completely inhibited induced IgE production at 3 mg/ml, while p6G5G4P did not. (These results are in FIG. 5).

Thus, these results suggested that an active Fc region, in particular that of human gamma-1, is significant for induced IgE inhibition by anti-human CD23 antibodies. These results also suggest that human anti-CD23 antibodies containing human gamma-3 constant regions will be significant for induced IgE inhibition because a gamma-3 constant region binds to the same FcγR receptors that gamma-1 binds to, and will likely mediate the same result.

EXAMPLE 2

To confirm our hypothesis as to the involvement of the Fc effector portion in IgE inhibition of anti-human CD23 antibodies, a third primate antibody, designated 2C8, also shown to inhibit IgE in in vitro) was converted to a F(ab')$_2$. IgE inhibitory activity was determined using the same IL-4/IgE assay described previously.

Materials

The following materials were used in this example.

ImmunoPure F(ab')$_2$ Preparation Kit (Pierce Catalog # 44888)

digestion buffer: 20 mM sodium acetate buffer, pH 4.5

0.1 M citric acid, pH 3.0 (adjust pH with NaOH)

0.1% sodium azide in water dialysis tubing; 50,000 MW cutoff (Spectra Por Catalog # 132 128)

shaking water bath capable of maintaining 37° C.

polystyrene culture tubes, 17×100 mm (Fisher Catalog # 14-956-6B)

BCA protein assay (Pierce Catalog # 23224)

Centricon-50 concentrators (Amicon Catalog # 4225).

Equilibration of Inmobilized Pepsin 0.25 milliliters of the 50% slurry of Immobilized Pepsin is added to a 17×100 mm test tube (0.125 ml of gel). Four milliliters of digestion buffer are then added. The pepsin is then separated from the buffer using the serum separator. The buffer is then discarded and the wash procedure repeated using another four milliliters of buffer. The immobilized pepsin is then resuspended in 0.5 ml of digestion buffer.

Preparation of Immobilized Protein A Column

Protein A AffinityPak® columns and ImmunoPure Binding and Elution buffers are brought to room temperature.

Preparation of 2C8 F(ab')$_2$ Fragments

2C8 F(ab')$_2$ fragments are prepared by methods well known in the antibody art. The inventors elected to use a commercially available kit, ImmunoPure F(ab')$_2$ Preparation Kit (Pierce Catalog # 44888), using the manufacturer's protocols.

Ten milligrams of lyophilized 2C8 antibody were dissolved in one milliliter of a digestion buffer (20 mM sodium acetate buffer, pH 4.5). One milliliter of the antibody containing sample was than added to a tube containing immobilized pepsin.

The antibody and immobilized pepsin were then incubated for four hours in a high speed shaker water bath at 37° C. (at high speed), taking care to maintain the mixing constant during the incubation.

The resultant solubilized F(ab')$_2$ and Fc fragments and the undigested IgGs were then recovered from the immobilized pepsin gel using a serum separator. The crude digest is then decanted into a clean tube.

In order to enhance recovery of F(ab')$_2$ fragments, the immobilized pepsin desirably is then washed with 1.5 of milliliters of the ImmunoPure IgG binding buffer. The wash is then added to the crude digest.

The antibody fragments were then recovered using a protein A column. This is effected by opening an immobilized protein A column. Care is taken to avoid air bubbles from being drawn into the gel. The storage solution (which contains 0.02% sodium azide) is discarded.

The immobilized protein A column was then equilibrated using twelve milliliters of binding buffer (contained in ImmunoPure Preparation Kit). The column was then transferred to a 17×100 mn test tube contained in the kit (labeled "F(ab')$_2$") to collect eluate.

Three milliliters of the crude digest was then applied to a column and are allowed to flow completely into the gel. The use of AffinityPak columns is desirable as these columns stop flowing automatically when the level reaches the top frit.

The column is then washed using six milliliters of binding buffer. The eluate which contains F(ab')$_2$ fragments was then collected. This eluate also contains small Fc fragments that can no longer bind protein A (which are not bound to the Protein A column). However, the substantial portion thereof was eliminated by dialysis.

Dialysis was effected by taking the F(ab')$_2$ containing eluate and dialyzing the eluate against pH 7.4 phosphate buffered saline, using dialysis tubing with a molecular weight cut-off of 50,000 so as to eliminate the small Fc fragment containments (Spectra Pur. Catalog # 132 128).

This resulted in a F(ab')$_2$ fraction having an optical density of 280 nm of 0.707 (6 ml). After dialysis and concentration with Centricon-50 concentrators (Amicon Catalog # 4225), the 2C8 F(ab')$_2$ product was assayed for protein content using a BCA protein assay (Pierce Catalog # 23224). The protein content was found to be 3.76 mg per milliliter.

The 2C8 F(ab)$_2$'s were assayed for IgE inhibitory activity and were found to be substantially incapable of inhibiting IgE production in the same in vitro assays described previously. These results are contained in FIG. 6. In fact, the F(ab')$_2$ was found to antagonize the suppressive effects of induced IgE on the monoclonal antibody 2C8. These results are in FIG. 7.

EXAMPLE 3

The PRIMATIZED® gamma 1 and gamma 4P versions of primate monoclonal 6G5 were both evaluated for their effect on inhibition of induced IgE production in vivo in the SCID mouse model described previously. p5E8G1N- was found to be as efficient as primate 5E8 in inhibiting induced IgE. (See FIGS. 8 and 9). While neither primate 6G5 nor the primatized p6G5G4P were effective at inhibiting induced IgE in vivo, primatized p6G5G1 inhibited induced IgE production. (See FIGS. 9 and 10) These results further substantiate our conclusion that an active Fc region is significant to the ability of an anti-human CD23 antibody to effectively inhibit induced IgE production.

Proposed Mechanism

Although the results of the present invention conclusively demonstrate that an active Fc region is significant to the ability of an anti-human CD23 antibody to effectively inhibit induced IgE production, the molecular mechanism has not been elucidated. However, several hypotheses may be made.

Firstly, it may be that the anti-CD23 antibodies of the present invention function to trigger a similar signal transduction pathway as is apparently triggered by cross-linking B cell receptor with anti-BCR gamma-1 antibodies. It has been hypothesized that the down-regulation of antigen receptor signaling in this case results from coligation of Fc gamma RII and surface Ig (B cell receptor) on the same B cell, leading to down regulation of Ig expression. (D'Ambrosia et al., 1995, Science, 268:293–297; Ono et al., 1997, Cell 90: 293–301). Indeed, CD23 is upregulated on the surface of IgE-expressing B cells, so it is possible that coligation of CD23 and the FcγRII-B receptor via the gamma-1 constant region results in a similar signal transduction pathway.

Alternatively, inhibition of induced IgE expression may be occurring through cross-linking of surface IgE on B cells at the same time as the Fc region interacts with an appropriate FcγR receptor on another cell type, i.e. a killer T cell, which may then "instruct" the B cell to undergo apoptosis, or lead to cell death in some other manner (i.e. phagocytosis). For instance, U.S. Pat. No. 5,543,144, herein incorporated by reference, proposes a similar mechanism for inhibiting IgE-expressing B cells with anti-IgE antibodies. As discussed therein, antibodies of certain IgG subclasses, such as mouse IgG2a and human IgG1 and IgG3, can mediate ADCC (Antibody Dependent Cellular Cytotoxicity) carried out by certain Fc receptor-bearing phagocytic leukocytes. For example, OKT3, a mouse IgG2a monoclonal antibody specific for human T cell surface antigen (which was the first monoclonal antibody product approved by the FDA for marketing as a therapeutic agent) is used in patients to provide rapid depletion of T cells in the blood and to induce an immunosuppressed state (for kidney transplantation). (Russell, P. S. et.al, Transpl. Proc. 17:39–41 (1985)). OKT3, at a dosage of 5 mg/day/subject, can completely deplete circulating T cells. The monoclonal antibodies described in U.S. Pat. No. 5,543,144, especially in the form of mouse gamma 2a antibodies or human or humanized antibodies bearing human gamma-1 or gamma-3 chains, are proposed to deplete IgE-expressing B cells by the ADCC mechanism in a similar manner.

But whatever the actual molecular mechanism for inhibiting IgE expression using anti-CD23 antibodies may be, it is clear that the Fc region, and accordingly effector function, of anti-CD23 antibodies are important considerations. As discussed previously, since complement is not present in the in vitro assays of the present invention, the phenomenon likely involves one or more FcγR receptors. Once the relevant molecular components are identified, as well as molecules internal to the cells involved which are involved in signal transduction pathways, it will be possible to design other therapeutics which may also be used to inhibit induced IgE expression.

Utility

Because of their ability to effectively inhibit IgE production, the subject anti-human CD23 antibodies which comprise human gamma-1 constant domains, and those that may also be constructed containing gamma-3, are effective in treating any disease wherein inhibition of IgE production is therapeutically desirable. Such diseases include by way of example allergic diseases, autoimmune diseases and inflammatory disease.

Specific conditions which are potentially treatable by administration of the subject anti-CD23 human gamma-1 gamma-3 constant domain containing antibodies include the following:

Allergic bronchopulmonary aspergillosis; Allergic rhinitis and conjunctivitis autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Graft-vs.-host disease; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis_X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis; Wiskott-Aldrich syndrome.

Of these, the preferred indications treatable or presentable by administration of anti-CD23 antibodies include allergic rhinitis and conjunctivitis, atopic dermatitis; eczema; Job's syndrome, asthma; allergic conditions; and chronic inflammatory diseases and conditions, including CLL chronic lymphocytic leukemia, typically characterized by high levels of membrane CD23 and high circulating levels of sCD23 (Sarfati et al., Blood 71: 94–98 (1988)).

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

One skilled in the art would be able, by routine experimentation, to determine what an effective, non-toxic amount of antibody would be for the purpose of effecting allergic diseases and inflammatory conditions. Generally, however, an effective dosage will be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody of the invention may be oral, parenteral, by inhalation or topical. The term parenteral as used herein includes intravenous, intramuscular, subcutaneous, rectal, vaginal or intraperitoneal administration. The intravenous form of parenteral administration is generally preferred.

The daily parenteral and oral dosage regimens for employing compounds of the invention to prophylactically or therapeutically induce immunosuppression will generally be in the range of about 0.05 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibody of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following are, therefore, to be construed as merely illustrative examples and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5 k by weight of an antibody or fragment thereof of the invention in 10 k by volume propylene glycol and water. The solution is sterilized by filtration.

Ointment Composition

Antibody or fragment thereof of the invention 10 g.
White soft paraffin to 100.0 g.
The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.
Polawax GP 200 20.0 g.

Lanolin Anhydrous 2.0 g.

White Beeswax 2.5 g.

Methyl hydroxybenzoate 0.1 g.

Distilled Water to 100.0 g.

The polawax, beeswax and lanolin are heated together at 60° C. A solution of methyl hydroxybenzoate is added and homogenization is achieved using high speed stirring. The temperature is then allowed to fall to SOOC. The antibody or fragment thereof of the invention is then added and dispersed throughout, and the composition is allowed to cool with slow speed stirring.

Topical Lotion Composition

Antibody or fragment thereof of the invention 1.0 g.

Sorbitan Monolaurate 0.6 g. Polysorbate 20 0.6 g.

Cetostearyl Alcohol 1.2 g. Glycerin 6.0 g.

Methyl Hydroxybenzoate 0.2 g.

Purified Water B.P. to 100.00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.

Methyl Hydroxybenzoate 0.01 g.

Propyl Hydroxybenzoate 0.04 g.

Purified Water B.P. to 100.00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 Am pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5 k of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration. Composition for Administration by Inhalation For an aerosol container with a capacity of 15–20 ml: dissolve 10 mg. of an antibody or fragment thereof of the invention in ethanol (6–8 ml.), add 0.1–0.2 k of a lubricating agent, such as polysorbate 85 or oleic acid; and disperse such in a propellant, such as freon, preferably in combination of (1–2 dichlorotetrafluoroethane) and difluorochloromethane, and put into an appropriate aerosol container adapted for either intranasal or oral inhalation administration.

Parenteral Administrable Antibody Compositions

The antibodies and pharmaceutical compositions of the invention are particularly useful for parenteral administration, i.e., subcutaneously, intramuscularly or intravenously. The compositions for parenteral administration will commonly comprise a solution of an antibody of the invention or a cocktail thereof dissolved in an acceptable carrier, preferably an aqueous carrier. A variety of aqueous carriers may be employed, e.g., water, buffered water, 0.4 k saline (normal saline), 0.3% glycine, and the like. The use of normal saline is preferred. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely. Such concentrations will be selected primarily based on fluid volumes, viscosities, etc., according to the particular mode of administration selected. Generally suitable intravenous concentrations range from about one to one hundred milligrams per milliliter.

Thus, a pharmaceutical composition of the invention for intravenous injection could comprise 10 mL normal saline containing 40–50 mg of an anti-human CD23 antibody of the invention. Methods for preparing parenterally administrable compositions are well-known or will be apparent to those skilled in the art, and are described in more detail in, for example, *Remington's Pharmaceutical Science*, 15th ed., Mack Publishing Company, Easton, Pa., hereby incorporated by reference herein.

The antibodies of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the subject anti-CD23 antibodies sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., *Science*, 253:792–795 (1991).

From the foregoing, it will be appreciated that, although specific embodiments of the invention have been described herein for purposes of illustration, various modifications may be made without diverting from the scope of the invention. Accordingly, the invention is not limited by the appended claims.

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
       (A) LENGTH: 390 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..390

(ix) FEATURE:
       (A) NAME/KEY: mat_peptide
       (B) LOCATION: 58..390

(xi) SEQUENCE DESCRIPTION: SEQ ID NO: 1:

```
ATG GCC TGG ACT CTG CTC CTC GTC ACC CTC CTC ACT CAG GGC ACA GGA      48
Met Ala Trp Thr Leu Leu Leu Val Thr Leu Leu Thr Gln Gly Thr Gly
-19         -15                 -10                 -5

TCC TGG GCT CAG TCT GCC CCG ACT CAG CCT CCC TCT GTG TCT GGG TCT      96
Ser Trp Ala Gln Ser Ala Pro Thr Gln Pro Pro Ser Val Ser Gly Ser
        -1   1               5                   10

CCT GGA CAG TCG GTC ACC ATC TCC TGC ACT GGA ACC AGC GAT GAC GTT     144
Pro Gly Gln Ser Val Thr Ile Ser Cys Thr Gly Thr Ser Asp Asp Val
    15                  20                  25

GGT GGT TAT AAC TAT GTC TCC TGG TAC CAA CAC CAC CCA GGC AAA GCC     192
Gly Gly Tyr Asn Tyr Val Ser Trp Tyr Gln His His Pro Gly Lys Ala
30                  35                  40                  45

CCC AAA CTC ATG ATT TAT GAT GTC GCT AAG CGG GCC TCA GGG GTC TCT     240
Pro Lys Leu Met Ile Tyr Asp Val Ala Lys Arg Ala Ser Gly Val Ser
            50                  55                  60

GAT CGC TTC TCT GGC TCC AAG TCT GGC AAC ACG GCC TCC CTG ACC ATC     288
Asp Arg Phe Ser Gly Ser Lys Ser Gly Asn Thr Ala Ser Leu Thr Ile
                65                  70                  75

TCT GGG CTC CAG GCT GAG GAC GAG GCT GAT TAT TAC TGT TGT TCA TAT     336
Ser Gly Leu Gln Ala Glu Asp Glu Ala Asp Tyr Tyr Cys Cys Ser Tyr
            80                  85                  90

ACA ACC AGT AGC ACT TTG TTA TTC GGA AGA GGG ACC CGG TTG ACC GTC     384
Thr Thr Ser Ser Thr Leu Leu Phe Gly Arg Gly Thr Arg Leu Thr Val
        95                  100                 105

CTA GGT                                                              390
Leu Gly
110
```

(2) INFORMATION FOR SEQ ID NO: 2:

(i) SEQUENCE CHARACTERISTICS:
       (A) LENGTH: 423 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..423

(ix) FEATURE:
         (A) NAME/KEY: mat_peptide
         (B) LOCATION: 58..423

(xi) SEQUENCE DESCRIPTION: SEQ ID NO: 2:

```
ATG AAA CAC CTG TGG TTC TTC CTC CTC CTG GTG GCA GCT CCC AGA TGG        48
Met Lys His Leu Trp Phe Phe Leu Leu Leu Val Ala Ala Pro Arg Trp
-19             -15                 -10                 -5

GTC CTG TCC CAG CTG CAG CTG CAG GAG TCG GGC CCA GGA GTG GTG AAG        96
Val Leu Ser Gln Leu Gln Leu Gln Glu Ser Gly Pro Gly Val Val Lys
         -1   1               5                   10

CCT TCG GAG ACC CTG TCC CTC ACC TGC GCT GTC TCT GGT GGC TCT GTC       144
Pro Ser Glu Thr Leu Ser Leu Thr Cys Ala Val Ser Gly Gly Ser Val
        15                  20                  25

AGC AGT AGT AAC TGG TGG ACC TGG ATC CGC CAG CCC CCA GGG AAG GGA       192
Ser Ser Ser Asn Trp Trp Thr Trp Ile Arg Gln Pro Pro Gly Lys Gly
    30                  35                  40                  45

CTG GAG TGG ATT GGA CGT ATC TCT GGT AGT GGT GGG GCC ACC AAC TAC       240
Leu Glu Trp Ile Gly Arg Ile Ser Gly Ser Gly Gly Ala Thr Asn Tyr
                50                  55                  60

AAC CCG TCC CTC AAG AGT CGA GTC ATC ATT TCA CAA GAC ACG TCC AAG       288
Asn Pro Ser Leu Lys Ser Arg Val Ile Ile Ser Gln Asp Thr Ser Lys
                65                  70                  75

AAC CAG TTC TCC CTG AAC CTG AAC TCT GTG ACC GCC GCG GAC ACG GCC       336
Asn Gln Phe Ser Leu Asn Leu Asn Ser Val Thr Ala Ala Asp Thr Ala
            80                  85                  90

GTG TAT TAC TGT GCC AGA GAT TGG GCC CAA ATA GCT GGA ACA ACG CTA       384
Val Tyr Tyr Cys Ala Arg Asp Trp Ala Gln Ile Ala Gly Thr Thr Leu
        95                  100                 105

GGC TTC TGG GGC CAG GGA GTC CTG GTC ACC GTC TCC TCA                   423
Gly Phe Trp Gly Gln Gly Val Leu Val Thr Val Ser Ser
110                 115                 120
```

(2) INFORMATION FOR SEQ ID NO: 3:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 1..387

(ix) FEATURE:
         (A) NAME/KEY: mat_peptide
         (B) LOCATION: 67..387

(xi) SEQUENCE DESCRIPTION: SEQ ID NO: 3:

```
ATG GAC ATG AGG GTC CCC GCT CAG CTC CTG GGG CTC CTT CTG CTC TGG        48
Met Asp Met Arg Val Pro Ala Gln Leu Leu Gly Leu Leu Leu Leu Trp
-22         -20                 -15                 -10

CTC CCA GGT GCC AGA TGT GAC ATC CAG ATG ACC CAG TCT CCA TCT TCC        96
Leu Pro Gly Ala Arg Cys Asp Ile Gln Met Thr Gln Ser Pro Ser Ser
        -5              -1   1               5                   10

CTG TCT GCA TCT GTA GGG GAC AGA GTC ACC ATC ACT TGC AGG GCA AGT       144
Leu Ser Ala Ser Val Gly Asp Arg Val Thr Ile Thr Cys Arg Ala Ser
                15                  20                  25

CAG GAC ATT AGG TAT TAT TTA AAT TGG TAT CAG CAG AAA CCA GGA AAA       192
Gln Asp Ile Arg Tyr Tyr Leu Asn Trp Tyr Gln Gln Lys Pro Gly Lys
            30                  35                  40
```

```
GCT CCT AAG CTC CTG ATC TAT GTT GCA TCC AGT TTG CAA AGT GGG GTC        240
Ala Pro Lys Leu Leu Ile Tyr Val Ala Ser Ser Leu Gln Ser Gly Val
        45                  50                  55

CCA TCA AGG TTC AGC GGC AGT GGA TCT GGG ACA GAG TTC ACT CTC ACC        288
Pro Ser Arg Phe Ser Gly Ser Gly Ser Gly Thr Glu Phe Thr Leu Thr
    60                  65                  70

GTC AGC AGC CTG CAG CCT GAA GAT TTT GCG ACT TAT TAC TGT CTA CAG        336
Val Ser Ser Leu Gln Pro Glu Asp Phe Ala Thr Tyr Tyr Cys Leu Gln
75                  80                  85                  90

GTT TAT AGT ACC CCT CGG ACG TTC GGC CAA GGG ACC AAG GTG GAA ATC        384
Val Tyr Ser Thr Pro Arg Thr Phe Gly Gln Gly Thr Lys Val Glu Ile
                95                  100                 105

AAA                                                                    387
Lys (2) INFORMATION FOR SEQ ID NO: 4:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..411

(ix) FEATURE:
        (A) NAME/KEY: mat_peptide
        (B) LOCATION: 58..411

(xi) SEQUENCE DESCRIPTION: SEQ ID NO: 4:

ATG GAG TTT GGG CTG AGC TGG GTT TTC CTT GTT CCT CTT TTG AAA GGT         48
Met Glu Phe Gly Leu Ser Trp Val Phe Leu Val Pro Leu Leu Lys Gly
-19             -15                 -10                 -5

GTC CAG TGT GAG GTG CAG CTG GTG GAG TCT GGG GGC GGC TTG GCA AAG         96
Val Gln Cys Glu Val Gln Leu Val Glu Ser Gly Gly Gly Leu Ala Lys
        -1   1               5                   10

CCT GGG GGG TCC CTG AGA CTC TGG TGC GCA GCC TCC GGG TTC AGG TTC        144
Pro Gly Gly Ser Leu Arg Leu Trp Cys Ala Ala Ser Gly Phe Arg Phe
        15                  20                  25

ACC TTC AAT AAC TAC TAC ATG GAC TGG GTC CGC CAG GCT CCA GGG CAG        192
Thr Phe Asn Asn Tyr Tyr Met Asp Trp Val Arg Gln Ala Pro Gly Gln
30                  35                  40                  45

GGG CTG GAG TGG GTC TCA CGT ATT AGT AGT AGT GGT GAT CCC ACA TGG        240
Gly Leu Glu Trp Val Ser Arg Ile Ser Ser Ser Gly Asp Pro Thr Trp
                50                  55                  60

TAC GCA GAC TCC GTG AAG GGC AGA TTC ACC ATC TCC AGA GAG AAC GCC        288
Tyr Ala Asp Ser Val Lys Gly Arg Phe Thr Ile Ser Arg Glu Asn Ala
            65                  70                  75

AAC AAC ACA CTG TTT CTT CAA ATG AAC AGC CTG AGA GCT GAG GAC ACG        336
Asn Asn Thr Leu Phe Leu Gln Met Asn Ser Leu Arg Ala Glu Asp Thr
        80                  85                  90

GCT GTC TAT TAC TGT GCG AGC TTG ACT ACA GGG TCT GAC TCC TGG GGC        384
Ala Val Tyr Tyr Cys Ala Ser Leu Thr Thr Gly Ser Asp Ser Trp Gly
    95                  100                 105

CAG GGA GTC CTG GTC ACC GTC TCC TCA                                    411
Gln Gly Val Leu Val Thr Val Ser Ser
110                 115

(2) INFORMATION FOR SEQ ID NO: 5:
```

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ATCACAGATC TCTCACCATG GACATGAGGG TCCCCGCTCA G        41

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

ATCACAGATC TCTCACCATG AGGCTCCCTG CTCAG               35

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 24
        (D) OTHER INFORMATION: /note= "Nucleotide 24 is N wherein
            N = A/G."

(ix) FEATURE:
        (A) NAME/KEY: misc_feature
        (B) LOCATION: 32
        (D) OTHER INFORMATION: /note= "Nucleotide 32 is N wherein
            N = T/G."

(xi) SEQUENCE DESCRIPTION: SEQ ID NO: 7:

ATCACAGATC TCTCACCATG GAANCCCCAG CNCAG               35

(2) INFORMATION FOR SEQ ID NO: 8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ATCACAGATC TCTCACCATG GTGTTGCAGA CCCAGGTC            38

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
         (A) NAME/KEY: misc_feature
         (B) LOCATION: 24
         (D) OTHER INFORMATION: /note= "Nucleotide 24 is N wherein
             N = C/T."

(ix) FEATURE:
         (A) NAME/KEY: misc_feature
         (B) LOCATION: 29
         (D) OTHER INFORMATION: /note= "Nucleotide 29 is N wherein
             N = G/C."

(xi) SEQUENCE DESCRIPTION: SEQ ID NO: 9:

GGTGCAGCCA CCGTAGCTTT GATNTCCAN                                              29

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 21
         (D) OTHER INFORMATION: /note= "Nucleotide 21 is N wherein
             N = G/A."

(ix) FEATURE:
         (A) NAME/KEY: misc_feature
         (B) LOCATION: 26
         (D) OTHER INFORMATION: /note= "Nucleotide 26 is N wherein
             N = G/C."

(xi) SEQUENCE DESCRIPTION: SEQ ID NO: 10:

ATCACAGATC TCTCACCATG NCCTGNTCCC CTCT                                        34

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 27
         (D) OTHER INFORMATION: /note= "Nucleotide 27 is N wherein
             N = A/G."

(ix) FEATURE:
         (A) NAME/KEY: misc_feature
         (B) LOCATION: 31
         (D) OTHER INFORMATION: /note= "Nucleotide 31 is N wherein
             N = T/C."

(xi) SEQUENCE DESCRIPTION: SEQ ID NO: 11:

ATCACAGATC TCTCACCATG GCCTGGNCTC NGCT                                        34

(2) INFORMATION FOR SEQ ID NO: 12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear
```

(ii) MOLECULE TYPE: DNA (genomic)

(ix) FEATURE:
            (A) NAME/KEY: misc_feature
            (B) LOCATION: 23
            (D) OTHER INFORMATION: /note= "Nucleotide 23 is N wherein
                N = A/C."

(ix) FEATURE:
            (A) NAME/KEY: misc_feature
            (B) LOCATION: 29
            (D) OTHER INFORMATION: /note= "Nucleotide 29 is N wherein
                N = T/C."

(xi) SEQUENCE DESCRIPTION: SEQ ID NO: 12:

ATCACAGATC TCTCACCATG GCNTGGANCC CTCTC                                   35

(2) INFORMATION FOR SEQ ID NO: 13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

CTTGGGCTGA CCTAGGACGG T                                                  21

(2) INFORMATION FOR SEQ ID NO: 14:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 14:

GCGACTAAGT CGACCATGGA CTGGACCTGG                                         30

(2) INFORMATION FOR SEQ ID NO: 15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

GCGACTAAGT CGACCATGAA ACACCTGTGG                                         30

(2) INFORMATION FOR SEQ ID NO: 16:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

GCGACTAAGT CGACCATGGA GTTTGGGCTG AGC                                     33

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GCGACTAAGT CGACCATGGG GTCAACCGCC ATC                              33

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GCGACTAAGT CGACCATGTC TGTCTCCTTC CTC                              33

(2) INFORMATION FOR SEQ ID NO: 19:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GCCAGGGGGA AGACCGATGG GCCCTTGGTG CTAGCTGAGG AGACGG                46

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GATGGGCCCT TGGTGCTAGC TGAGGAGACG G                                31

(2) INFORMATION FOR SEQ ID NO: 21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GGTGCTAGCT GAGGAGACGG TGACCAGGAC TCCCTGGCCC CAGAAGCCTA G          51

(2) INFORMATION FOR SEQ ID NO: 22:

(i) SEQUENCE CHARACTERISTICS:

(A) LENGTH: 17 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 22:

ATTTAGGTGA CACTATA                                                          17

(2) INFORMATION FOR SEQ ID NO: 23:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 23:

GTTTTCCCAG TCACGA                                                           16

(2) INFORMATION FOR SEQ ID NO: 24:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 24:

ATATACGACT CACTATAGGG                                                       20

(2) INFORMATION FOR SEQ ID NO: 25:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 25:

CCGTCAGATC GCCTGGAGAC GCCA                                                  24

(2) INFORMATION FOR SEQ ID NO: 26:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 26:

GCAGTTCCAG ATTTCAACTG                                                       20

(2) INFORMATION FOR SEQ ID NO: 27:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 27:

CCAGGCCACT GTCACGGCTT C                                              21

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

CAGAGCTGGG TACGTCCTCA                                                20

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GCCCCCAGAG GTGCTCTTGG                                                20

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

ACACAGACCC GTCGACATGG                                                20

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

GCTCTCGGAG GTGCTCCTGG                                                20

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
ACAGACCCGT CGACCATGGA GTTTGGGCTG                                              30

(2) INFORMATION FOR SEQ ID NO: 33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

CCCCTTGGTG CTAGCTGAGG AGACGGT                                                 27

(2) INFORMATION FOR SEQ ID NO: 34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

AGAGAGAACG CCAAGAACAC ACTGTTT                                                 27

(2) INFORMATION FOR SEQ ID NO: 35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

AAACAGTGTG TTCTTGGCGT TCTCTCT                                                 27
```

What is claimed is:

1. A chimeric anti-human CD23 antibody wherein the light chain variable domain consists of the polypeptide encoded by nucleotides 58–390 of SEQ ID NO: 1, the heavy chain variable domain consists of the polypeptide encoded by nucleotides 58–423 of SEQ ID NO:3, and the constant region is a human constant region selected from the group consisting of human gamma-1 and human gamma-3 constant regions.

2. The chimeric anti-human CD23 antibody of claim 1 wherein the human constant region is a human gamma-1 constant region.

3. The chimeric anti-human CD23 antibody of claim 1 wherein the human constant region is a human gamma-3 constant region.

4. A composition containing the chimeric anti-human CD23 antibody according to claim 1 and a pharmaceutically acceptable carrier.

5. A composition containing the chimeric anti-human CD23 antibody according to claim 2 and a pharmaceutically acceptable carrier.

6. A composition containing the chimeric anti-human CD23 antibody according to claim 3 and a pharmaceutically acceptable carrier.

7. A chimeric anti-human CD23 antibody wherein the light chain variable domain consists of the polypeptide encoded by nucleotides 67–387 of SEQ ID NO: 5, the heavy chain variable domain consists of the polypeptide encoded by nucleotides 58–411 of SEQ ID NO: 7, and the constant region is a human constant region selected from the group consisting of a human gamma-1 constant region and a human gamma-3 constant region.

8. A chimeric anti-human CD23 antibody wherein the light chain variable domain consists of the polypeptide encoded by nucleotides 67–387 of SEQ ID NO: 5 and the heavy chain variable domain consists of the polypeptide encoded by nucleotides 58–411 of SEQ ID NO: 7 with the exception that the asparagine codon encoded by nucleotides 289–291 of SEQ ID NO:7 is replaced with a lysine codon and the constant region is a human constant region selected from the group consisting of a human gamma-1 constant region and a human gamma-3 constant region.

9. The chimeric anti-human CD23 antibody according to claim 7 wherein the human constant region is a human gamma-1 constant region.

10. The chimeric anti-human CD23 antibody according to claim 7 wherein the human constant region is a human gamma-3 constant region.

11. The chimeric anti-human CD23 antibody according to claim 8 wherein the human constant region is gamma-1 constant region.

12. The chimeric anti-human CD23 antibody according to claim 8 which comprises a human gamma-3 constant region.

13. A composition comprising the chimeric anti-human CD23 antibody according to claim 8 and a pharmaceutically acceptable carrier.

14. A composition comprising the chimeric anti-human CD23 antibody according to claim 8 and a pharmaceutically acceptable carrier.

15. A composition comprising the chimeric anti-human CD23 antibody according to claim 9 and a pharmaceutically acceptable carrier.

16. A composition comprising the chimeric anti-human CD23 antibody according to claim 10 and a pharmaceutically acceptable carrier.

17. A composition comprising the chimeric anti-human CD23 antibody according to claim 11 and a pharmaceutically acceptable carrier.

18. A composition comprising the chimeric anti-human CD23 antibody according to claim 12 and a pharmaceutically acceptable carrier.

19. The composition of claim 4, which composition is a pharmaceutical composition.

20. The composition of claim 5, which composition is a pharmaceutical composition.

21. The composition of claim 6, which composition is a pharmaceutical composition.

22. The composition of claim 13, which composition is a pharmaceutical composition.

23. The composition of claim 14, which composition is a pharmaceutical composition.

24. The composition of claim 15, which composition is a pharmaceutical composition.

25. The composition of claim 16, which composition is a pharmaceutical composition.

26. The composition of claim 17, which composition is a pharmaceutical composition.

27. The composition of claim 18, which composition is pharmaceutical composition.

* * * * *

UNITED STATES PATENT AND TRADEMARK OFFICE
CERTIFICATE OF CORRECTION

PATENT NO.    : 6,893,636 B2
DATED         : May 17, 2005
INVENTOR(S)   : Reff et al.

It is certified that error appears in the above-identified patent and that said Letters Patent is hereby corrected as shown below:

Delete Columns 47-64 and Columns 65-66, lines 1-42 and insert the attached pages.

Signed and Sealed this

Ninth Day of May, 2006

JON W. DUDAS
*Director of the United States Patent and Trademark Office*

SEQUENCE LISTING

<110> REFF, MITCHELL E.
      KLOETZER, WILLIAM S.
      NAKAMURA, TAKEHIKO

<120> GAMMA-1 AND GAMMA-3 ANTI-HUMAN CD23 MONOCLONAL ANTIBODIES AND USE THEREOF AS THERAPEUTICS

<130> 037003-0275470

<140> 09/019,441
<141> 1998-02-05

<150> 08/803,085
<151> 1997-02-20

<160> 39

<170> PatentIn Ver. 2.1

<210> 1
<211> 390
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(57)
<223> leader sequence <220>
<221> mat_peptide
<222> (58)..(390)

<220>
<221> CDS
<222> (1)..(390)

<400> 1

```
atg gcc tgg act ctg ctc ctc gtc acc ctc ctc act cag ggc aca gga      48
Met Ala Trp Thr Leu Leu Leu Val Thr Leu Leu Thr Gln Gly Thr Gly
                -15                 -10                  -5 tcc tgg gct cag tct gcc ccg act cag cct ccc tct gtg tct ggg tct      96
Ser Trp Ala Gln Ser Ala Pro Thr Gln Pro Pro Ser Val Ser Gly Ser
            -1   1               5                  10 cct gga cag tcg gtc acc atc tcc tgc act gga acc agc gat gac gtt     144
Pro Gly Gln Ser Val Thr Ile Ser Cys Thr Gly Thr Ser Asp Asp Val
        15                  20                  25
```

```
ggt ggt tat aac tat gtc tcc tgg tac caa cac cac cca ggc aaa gcc      192
Gly Gly Tyr Asn Tyr Val Ser Trp Tyr Gln His His Pro Gly Lys Ala
 30              35              40              45 ccc aaa ctc atg att tat gat gtc gct aag cgg gcc tca ggg gtc tct      240
Pro Lys Leu Met Ile Tyr Asp Val Ala Lys Arg Ala Ser Gly Val Ser
             50              55              60 gat cgc ttc tct ggc tcc aag tct ggc aac acg gcc tcc ctg acc atc      288
Asp Arg Phe Ser Gly Ser Lys Ser Gly Asn Thr Ala Ser Leu Thr Ile
             65              70              75 tct ggg ctc cag gct gag gac gag gct gat tat tac tgt tgt tca tat      336
Ser Gly Leu Gln Ala Glu Asp Glu Ala Asp Tyr Tyr Cys Cys Ser Tyr
             80              85              90 aca acc agt agc act ttg tta ttc gga aga ggg acc cgg ttg acc gtc      384
Thr Thr Ser Ser Thr Leu Leu Phe Gly Arg Gly Thr Arg Leu Thr Val
     95             100             105 cta ggt                                                              390
Leu Gly
110
```

<210> 2
<211> 130
<212> PRT
<213> Artifical Sequence

<220>
<223> Description of Artificial Sequence: Mature peptide is derived from Old World Monkey (macaque); leader sequence is an artificial sequence to facilitate cloning

<400> 2

```
Met Ala Trp Thr Leu Leu Leu Val Thr Leu Leu Thr Gln Gly Thr Gly
                 -15             -10                  -5

Ser Trp Ala Gln Ser Ala Pro Thr Gln Pro Pro Ser Val Ser Gly Ser
         -1   1               5

Leu Gly
110

<210> 3
<211> 423
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(57)
<223> leader sequence <220>
<221> mat_peptide
<222> (58)..(423)

<220>
<221> CDS
<222> (1)..(423)

<400> 3

| atg | aaa | cac | ctg | tgg | ttc | ttc | ctc | ctc | ctg | gtg | gca | gct | ccc | aga | tgg | 48 |
|-----|-----|-----|-----|-----|-----|-----|-----|-----|-----|-----|-----|-----|-----|-----|-----|-----|
| Met | Lys | His | Leu | Trp | Phe | Phe | Leu | Leu | Leu | Val | Ala | Ala | Pro | Arg | Trp | |
| | | | -15 | | | | | -10 | | | | | -5 | | | |

| gtc | ctg | tcc | cag | ctg | cag | ctg | cag | gag | tcg | ggc | cca | gga | gtg | gtg | aag | 96 |
| Val | Leu | Ser | Gln | Leu | Gln | Leu | Gln | Glu | Ser | Gly | Pro | Gly | Val | Val | Lys | |
| | | -1 | 1 | | | | 5 | | | | | 10 | | | | |

| cct | tcg | gag | acc | ctg | tcc | ctc | acc | tgc | gct | gtc | tct | ggt | ggc | tct | gtc | 144 |
| Pro | Ser | Glu | Thr | Leu | Ser | Leu | Thr | Cys | Ala | Val | Ser | Gly | Gly | Ser | Val | |
| | 15 | | | | | 20 | | | | | 25 | | | | | |

| agc | agt | agt | aac | tgg | tgg | acc | tgg | atc | cgc | cag | ccc | cca | ggg | aag | gga | 192 |
| Ser | Ser | Ser | Asn | Trp | Trp | Thr | Trp | Ile | Arg | Gln | Pro | Pro | Gly | Lys | Gly | |
| 30 | | | | 35 | | | | 40 | | | | | | 45 | | |

| ctg | gag | tgg | att | gga | cgt | atc | tct | ggt | agt | ggt | ggg | gcc | acc | aac | tac | 240 |
| Leu | Glu | Trp | Ile | Gly | Arg | Ile | Ser | Gly | Ser | Gly | Gly | Ala | Thr | Asn | Tyr | |
| | | | | 50 | | | | | 55 | | | | | 60 | | |

| aac | ccg | tcc | ctc | aag | agt | cga | gtc | atc | att | tca | caa | gac | acg | tcc | aag | 288 |
| Asn | Pro | Ser | Leu | Lys | Ser | Arg | Val | Ile | Ile | Ser | Gln | Asp | Thr | Ser | Lys | |
| | | | 65 | | | | | 70 | | | | | 75 | | | |

| aac | cag | ttc | tcc | ctg | aac | ctg | aac | tct | gtg | acc | gcc | gcg | gac | acg | gcc | 336 |
| Asn | Gln | Phe | Ser | Leu | Asn | Leu | Asn | Ser | Val | Thr | Ala | Ala | Asp | Thr | Ala | |
| | | | 80 | | | | | 85 | | | | | 90 | | | |

| gtg | tat | tac | tgt | gcc | aga | gat | tgg | gcc | caa | ata | gct | gga | aca | acg | cta | 384 |
| Val | Tyr | Tyr | Cys | Ala | Arg | Asp | Trp | Ala | Gln | Ile | Ala | Gly | Thr | Thr | Leu | |
| | 95 | | | | 100 | | | | | 105 | | | | | | |

```
ggc ttc tgg ggc cag gga gtc ctg gtc acc gtc tcc tca            423
Gly Phe Trp Gly Gln Gly Val Leu Val Thr Val Ser Ser
110             115             120
```

<210> 4
<211> 141
<212> PRT
<213> Artifical Sequence

<220>
<223> Description of Artificial Sequence: Mature peptide is derived from Old World Monkey (macaque); leader sequence is an artificial sequence to facilitate cloning

<400> 4

```
Met Lys His Leu Trp Phe Phe Leu Leu Leu Val Ala Ala Pro Arg Trp
            -15                 -10                 -5

Val Leu Ser Gln Leu Gln Leu Gln Glu Ser Gly Pro Gly Val Val Lys
         -1   1              5              10

Pro Ser Glu Thr Leu Ser Leu Thr Cys Ala Val Ser Gly Gly Ser Val
     15              20              25

Ser Ser Ser Asn Trp Trp Thr Trp Ile Arg Gln Pro Pro Gly Lys Gly
 30              35              40              45

Leu Glu Trp Ile Gly Arg Ile Ser Gly Ser Gly Gly Ala Thr Asn Tyr
             50              55              60

Asn Pro Ser Leu Lys Ser Arg Val Ile Ile Ser Gln Asp Thr Ser Lys
             65              70              75

Asn Gln Phe Ser Leu Asn Leu Asn Ser Val Thr Ala Ala Asp Thr Ala
         80              85              90

Val Tyr Tyr Cys Ala Arg Asp Trp Ala Gln Ile Ala Gly Thr Thr Leu
     95              100             105

Gly Phe Trp Gly Gln Gly Val Leu Val Thr Val Ser Ser
110             115             120
```

<210> 5
<211> 387
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(66)
<223> leader sequence

<220>

<221> mat_peptide
<222> (67)..(387)

<220>
<221> CDS
<222> (1)..(387)

<400> 5

```
atg gac atg agg gtc ccc gct cag ctc ctg ggg ctc ctt ctg ctc tgg      48
Met Asp Met Arg Val Pro Ala Gln Leu Leu Gly Leu Leu Leu Leu Trp
        -20                 -15                 -10 ctc cca ggt gcc aga tgt gac atc cag atg acc cag tct cca tct tcc      96
Leu Pro Gly Ala Arg Cys Asp Ile Gln Met Thr Gln Ser Pro Ser Ser
     -5              -1   1               5                   10 ctg tct gca tct gta ggg gac aga gtc acc atc act tgc agg gca agt     144
Leu Ser Ala Ser Val Gly Asp Arg Val Thr Ile Thr Cys Arg Ala Ser
                 15                  20                  25 cag gac att agg tat tat tta aat tgg tat cag cag aaa cca gga aaa     192
Gln Asp Ile Arg Tyr Tyr Leu Asn Trp Tyr Gln Gln Lys Pro Gly Lys
             30                  35                  40 gct cct aag ctc ctg atc tat gtt gca tcc agt ttg caa agt ggg gtc     240
Ala Pro Lys Leu Leu Ile Tyr Val Ala Ser Ser Leu Gln Ser Gly Val
         45                  50                  55 cca tca agg ttc agc ggc agt gga tct ggg aca gag ttc act ctc acc     288
Pro Ser Arg Phe Ser Gly Ser Gly Ser Gly Thr Glu Phe Thr Leu Thr
     60                  65                  70 gtc agc agc ctg cag cct gaa gat ttt gcg act tat tac tgt cta cag     336
Val Ser Ser Leu Gln Pro Glu Asp Phe Ala Thr Tyr Tyr Cys Leu Gln
 75                  80                  85                  90 gtt tat agt acc cct cgg acg ttc ggc caa ggg acc aag gtg gaa atc     384
Val Tyr Ser Thr Pro Arg Thr Phe Gly Gln Gly Thr Lys Val Glu Ile
                 95                  100                 105 aaa                                                                  387
Lys
```

<210> 6
<211> 129
<212> PRT
<213> Artifical Sequence

<220>
<223> Description of Artificial Sequence: Mature peptide is derived from Old World Monkey (macaque); leader sequence is an artificial sequence to facilitate cloning

<400> 6

```
Met Asp Met Arg Val Pro Ala Gln Leu Leu Gly Leu Leu Leu Leu Trp
        -20                 -15                 -10

Leu Pro Gly Ala Arg Cys Asp Ile Gln Met Thr Gln Ser Pro Ser Ser
```

```
         -5              -1    1            5                     10
     Leu Ser Ala Ser Val Gly Asp Arg Val Thr Ile Thr Cys Arg Ala Ser
                     15                20                25

Gln Asp Ile Arg Tyr Tyr Leu Asn Trp Tyr Gln Gln Lys Pro Gly Lys
                 30                  35                  40

Ala Pro Lys Leu Leu Ile Tyr Val Ala Ser Ser Leu Gln Ser Gly Val
             45                  50                  55

Pro Ser Arg Phe Ser Gly Ser Gly Ser Gly Thr Glu Phe Thr Leu Thr
         60                  65                  70

Val Ser Ser Leu Gln Pro Glu Asp Phe Ala Thr Tyr Tyr Cys Leu Gln
     75                  80                  85                  90

Val Tyr Ser Thr Pro Arg Thr Phe Gly Gln Gly Thr Lys Val Glu Ile
                         95                  100                 105

Lys

<210> 7
<211> 411
<212> DNA
<213> Artifical Sequence

<220>
<223> Description of Artificial Sequence: Mature peptide is derived from Old
World Monkey (macaque); leader sequence is an artificial sequence to
facilitate cloning <220>
<221> misc_feature
<222> (1)..(57)
<223> leader sequence <220>
<221> mat_peptide
<222> (58)..(411)

<220>
<221> CDS
<222> (1)..(411)

<400> 7 atg gag ttt ggg ctg agc tgg gtt ttc ctt gtt cct ctt ttg aaa ggt    48
Met Glu Phe Gly Leu Ser Trp Val Phe Leu Val Pro Leu Leu Lys Gly
                -15                 -10                 -5 gtc cag tgt gag gtg cag ctg gtg gag tct ggg ggc ggc ttg gca aag    96
Val Gln Cys Glu Val Gln Leu Val Glu Ser Gly Gly Gly Leu Ala Lys
            -1   1               5                   10 cct ggg ggg tcc ctg aga ctc tcc tgc gca gcc tcc ggg ttc agg ttc   144
Pro Gly Gly Ser Leu Arg Leu Ser Cys Ala Ala Ser Gly Phe Arg Phe
        15                  20                  25
```

```
acc ttc aat aac tac tac atg gac tgg gtc cgc cag gct cca ggg cag     192
Thr Phe Asn Asn Tyr Tyr Met Asp Trp Val Arg Gln Ala Pro Gly Gln
 30                  35                  40                  45 ggg ctg gag tgg gtc tca cgt att agt agt agt ggt gat ccc aca tgg     240
Gly Leu Glu Trp Val Ser Arg Ile Ser Ser Ser Gly Asp Pro Thr Trp
             50                  55                  60 tac gca gac tcc gtg aag ggc aga ttc acc atc tcc aga gag aac gcc     288
Tyr Ala Asp Ser Val Lys Gly Arg Phe Thr Ile Ser Arg Glu Asn Ala
                 65                  70                  75 aac aac aca ctg ttt ctt caa atg aac agc ctg aga gct gag gac acg     336
Asn Asn Thr Leu Phe Leu Gln Met Asn Ser Leu Arg Ala Glu Asp Thr
         80                  85                  90 gct gtc tat tac tgt gcg agc ttg act aca ggg tct gac tcc tgg ggc     384
Ala Val Tyr Tyr Cys Ala Ser Leu Thr Thr Gly Ser Asp Ser Trp Gly
     95                 100                 105 cag gga gtc ctg gtc acc gtc tcc tca                                 411
Gln Gly Val Leu Val Thr Val Ser Ser
110             115
```

<210> 8
<211> 137
<212> PRT
<213> Artifical Sequence

<220>
<223> Description of Artificial Sequence: Mature peptide is derived from Old World Monkey (macaque); leader sequence is an artificial sequence to facilitate cloning

<400> 8

```
Met Glu Phe Gly Leu Ser Trp Val Phe Leu Val Pro Leu Leu Lys Gly
                -15                 -10                  -5

Val Gln Cys Glu Val Gln Leu Val Glu Ser Gly Gly Gly Leu Ala Lys
         -1   1               5                  10

Pro Gly Gly Ser Leu Arg Leu Ser Cys Ala Ala Ser Gly Phe Arg Phe
         15                  20                  25

Thr Phe Asn Asn Tyr Tyr Met Asp Trp Val Arg Gln Ala Pro Gly Gln
 30                  35                  40                  45

Gly Leu Glu Trp Val Ser Arg Ile Ser Ser Ser Gly Asp Pro Thr Trp
             50                  55                  60

Tyr Ala Asp Ser Val Lys Gly Arg Phe Thr Ile Ser Arg Glu Asn Ala
                 65                  70                  75

Asn Asn Thr Leu Phe Leu Gln Met Asn Ser Leu Arg Ala Glu Asp Thr
         80                  85                  90

Ala Val Tyr Tyr Cys Ala Ser Leu Thr Thr Gly Ser Asp Ser Trp Gly
     95                 100                 105
```

Gln Gly Val Leu Val Thr Val Ser Ser
110                 115

<210> 9
<211> 41
<212> DNA
<213> Artificial Sequence

<220>
<223> Description of Artificial Sequence: Primer

<400> 9
atcacagatc tctcaccatg gacatgaggg tccccgctca g        41

<210> 10
<211> 35
<212> DNA
<213> Artificial Sequence

<220>
<223> Description of Artificial Sequence: Primer

<400> 10
atcacagatc tctcaccatg aggctccctg ctcag              35

<210> 11
<211> 35
<212> DNA
<213> Artificial Sequence

<220>
<223> Description of Artificial Sequence: Primer

<400> 11
atcacagatc tctcaccatg gaarccccag ckcag              35

<210> 12
<211> 38
<212> DNA
<213> Artificial Sequence

<220>
<223> Description of Artificial Sequence: Primer

<400> 12
atcacagatc tctcaccatg gtgttgcaga cccaggtc           38

<210> 13
<211> 32
<212> DNA
<213> Artificial Sequence

<220>
<223> Description of Artificial Sequence: Primer

<400> 13
ggtgcagcca ccgtagcttt gatytccasc tt                                32

<210> 14
<211> 34
<212> DNA
<213> Artificial Sequence

<220>
<223> Description of Artificial Sequence: Primer

<400> 14
atcacagatc tctcaccatg rcctgstccc ctct                              34

<210> 15
<211> 34
<212> DNA
<213> Artificial Sequence

<220>
<223> Description of Artificial Sequence: Primer

<400> 15
atcacagatc tctcaccatg gcctggrctc ygct                              34

<210> 16
<211> 35
<212> DNA
<213> Artificial Sequence

<220>
<223> Description of Artificial Sequence: Primer

<400> 16
atcacagatc tctcaccatg gcmtggaycc ctctc                             35

<210> 17
<211> 21
<212> DNA
<213> Artificial Sequence

<220>
<223> Description of Artificial Sequence: Primer

<400> 17
cttgggctga cctaggacgg t                                            21

<210> 18
<211> 30

<212> DNA
<213> Artificial Sequence

<220>
<223> Description of Artificial Sequence: Primer

<400> 18
gcgactaagt cgaccatgga ctggacctgg           30

<210> 19
<211> 30
<212> DNA
<213> Artificial Sequence

<220>
<223> Description of Artificial Sequence: Primer

<400> 19
gcgactaagt cgaccatgaa acacctgtgg           30

<210> 20
<211> 33
<212> DNA
<213> Artificial Sequence

<220>
<223> Description of Artificial Sequence: Primer

<400> 20
gcgactaagt cgaccatgga gtttgggctg agc           33

<210> 21
<211> 33
<212> DNA
<213> Artificial Sequence

<220>
<223> Description of Artificial Sequence: Primer

<400> 21
gcgactaagt cgaccatggg gtcaaccgcc atc           33

<210> 22
<211> 33
<212> DNA
<213> Artificial Sequence

<220>
<223> Description of Artificial Sequence: Primer

<400> 22
gcgactaagt cgaccatgtc tgtctccttc ctc           33

<210> 23
<211> 46
<212> DNA
<213> Artificial Sequence

<220>
<223> Description of Artificial Sequence: Primer

<400> 23
gccaggggga agaccgatgg gcccttggtg ctagctgagg agacgg        46

<210> 24
<211> 31
<212> DNA
<213> Artificial Sequence

<220>
<223> Description of Artificial Sequence: Primer

<400> 24
gatgggccct tggtgctagc tgaggagacg g        31

<210> 25
<211> 51
<212> DNA
<213> Artificial Sequence

<220>
<223> Description of Artificial Sequence: Primer

<400> 25
ggtgctagct gaggagacgg tgaccaggac tccctggccc cagaagccta g        51

<210> 26
<211> 17
<212> DNA
<213> Artificial Sequence

<220>
<223> Description of Artificial Sequence: Primer

<400> 26
atttaggtga cactata        17

<210> 27
<211> 16
<212> DNA
<213> Artificial Sequence

<220>
<223> Description of Artificial Sequence: Primer

<400> 27
gttttcccag tcacga                                              16

<210> 28
<211> 20
<212> DNA
<213> Artificial Sequence

<220>
<223> Description of Artificial Sequence: Primer

<400> 28
atatacgact cactataggg                                          20

<210> 29
<211> 24
<212> DNA
<213> Artificial Sequence

<220>
<223> Description of Artificial Sequence: Primer

<400> 29
ccgtcagatc gcctggagac gcca                                     24

<210> 30
<211> 20
<212> DNA
<213> Artificial Sequence

<220>
<223> Description of Artificial Sequence: Primer

<400> 30
gcagttccag atttcaactg                                          20

<210> 31
<211> 21
<212> DNA
<213> Artificial Sequence

<220>
<223> Description of Artificial Sequence: Primer

<400> 31
ccaggccact gtcacggctt c                                        21

<210> 32
<211> 20
<212> DNA

<213> Artificial Sequence
<220>
<223> Description of Artificial Sequence: Primer

<400> 32
cagagctggg tacgtcctca                                    20

<210> 33
<211> 20
<212> DNA
<213> Artificial Sequence

<220>
<223> Description of Artificial Sequence: Primer

<400> 33
gcccccagag gtgctcttgg                                    20

<210> 34
<211> 20
<212> DNA
<213> Artificial Sequence

<220>
<223> Description of Artificial Sequence: Primer

<400> 34
acacagaccc gtcgacatgg                                    20

<210> 35
<211> 20
<212> DNA
<213> Artificial Sequence

<220>
<223> Description of Artificial Sequence: Primer

<400> 35
gctctcggag gtgctcctgg                                    20

<210> 36
<211> 30
<212> DNA
<213> Artificial Sequence

<220>
<223> Description of Artificial Sequence: Primer

<400> 36
acagacccgt cgaccatgga gtttgggctg                         30

<210> 37
<211> 27
<212> DNA
<213> Artificial Sequence

<220>
<223> Description of Artificial Sequence: Primer

<400> 37
ccccttggtg ctagctgagg agacggt                27

<210> 38
<211> 27
<212> DNA
<213> Artificial Sequence

<220>
<223> Description of Artificial Sequence: Primer

<400> 38
agagagaacg ccaagaacac actgttt                27

<210> 39
<211> 27
<212> DNA
<213> Artificial Sequence

<220>
<223> Description of Artificial Sequence: Primer

<400> 39
aaacagtgtg ttcttggcgt tctctct                27

SEQUENCE LISTING

<110> REFF, MITCHELL E.
      KLOETZER, WILLIAM S.
      NAKAMURA, TAKEHIKO

<120> GAMMA-1 AND GAMMA-3 ANTI-HUMAN CD23 MONOCLONAL ANTIBODIES AND USE THEREOF AS THERAPEUTICS

<130> 037003-0275470

<140> 09/019,441
<141> 1998-02-05

<150> 08/803,085
<151> 1997-02-20

<160> 39

<170> PatentIn Ver. 2.1

<210> 1
<211> 390
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(57)
<223> leader sequence <220>
<221> mat_peptide
<222> (58)..(390)

<220>
<221> CDS
<222> (1)..(390)

<400> 1

```
atg gcc tgg act ctg ctc ctc gtc acc ctc ctc act cag ggc aca gga    48
Met Ala Trp Thr Leu Leu Leu Val Thr Leu Leu Thr Gln Gly Thr Gly
            -15                 -10                 -5 tcc tgg gct cag tct gcc ccg act cag cct ccc tct gtg tct ggg tct    96
Ser Trp Ala Gln Ser Ala Pro Thr Gln Pro Pro Ser Val Ser Gly Ser
         -1   1               5                  10 cct gga cag tcg gtc acc atc tcc tgc act gga acc agc gat gac gtt   144
Pro Gly Gln Ser Val Thr Ile Ser Cys Thr Gly Thr Ser Asp Asp Val
     15                  20                  25
```

```
ggt ggt tat aac tat gtc tcc tgg tac caa cac cac cca ggc aaa gcc    192
Gly Gly Tyr Asn Tyr Val Ser Trp Tyr Gln His His Pro Gly Lys Ala
 30              35                  40                  45 ccc aaa ctc atg att tat gat gtc gct aag cgg gcc tca ggg gtc tct    240
Pro Lys Leu Met Ile Tyr Asp Val Ala Lys Arg Ala Ser Gly Val Ser
                 50                  55                  60 gat cgc ttc tct ggc tcc aag tct ggc aac acg gcc tcc ctg acc atc    288
Asp Arg Phe Ser Gly Ser Lys Ser Gly Asn Thr Ala Ser Leu Thr Ile
             65                  70                  75 tct ggg ctc cag gct gag gac gag gct gat tat tac tgt tgt tca tat    336
Ser Gly Leu Gln Ala Glu Asp Glu Ala Asp Tyr Tyr Cys Cys Ser Tyr
         80                  85                  90 aca acc agt agc act ttg tta ttc gga aga ggg acc cgg ttg acc gtc    384
Thr Thr Ser Ser Thr Leu Leu Phe Gly Arg Gly Thr Arg Leu Thr Val
     95                  100                 105 cta ggt                                                            390
Leu Gly
110
```

<210> 2
<211> 130
<212> PRT
<213> Artifical Sequence

<220>
<223> Description of Artificial Sequence: Mature peptide is derived from Old World Monkey (macaque); leader sequence is an artificial sequence to facilitate cloning

<400> 2

```
Met Ala Trp Thr Leu Leu Leu Val Thr Leu Leu Thr Gln Gly Thr Gly
                -15                 -10                  -5

Ser Trp Ala Gln Ser Ala Pro Thr Gln Pro Pro Ser Val Ser Gly Ser
         -1   1             5                  10

Pro Gly Gln Ser Val Thr Ile Ser Cys Thr Gly Thr Ser Asp Asp Val
     15                  20                  25

Gly Gly Tyr Asn Tyr Val Ser Trp Tyr Gln His His Pro Gly Lys Ala
 30              35                  40                  45

Pro Lys Leu Met Ile Tyr Asp Val Ala Lys Arg Ala Ser Gly Val Ser
                 50                  55                  60

Asp Arg Phe Ser Gly Ser Lys Ser Gly Asn Thr Ala Ser Leu Thr Ile
             65                  70                  75

Ser Gly Leu Gln Ala Glu Asp Glu Ala Asp Tyr Tyr Cys Cys Ser Tyr
         80                  85                  90

Thr Thr Ser Ser Thr Leu Leu Phe Gly Arg Gly Thr Arg Leu Thr Val
     95                  100                 105
```

```
Leu Gly
110

<210> 3
<211> 423
<212> DNA
<213> Artifical Sequence

<220>
<223> Description of Artificial Sequence: Mature peptide is derived from Old
World Monkey (macaque); leader sequence is an artificial sequence to
facilitate cloning <220>
<221> misc_feature
<222> (1)..(57)
<223> leader sequence <220>
<221> mat_peptide
<222> (58)..(423)

<220>
<221> CDS
<222> (1)..(423)

<400> 3 atg aaa cac ctg tgg ttc ttc ctc ctc ctg gtg gca gct ccc aga tgg      48
Met Lys His Leu Trp Phe Phe Leu Leu Leu Val Ala Ala Pro Arg Trp
                -15                 -10                  -5 gtc ctg tcc cag ctg cag ctg cag gag tcg ggc cca gga gtg gtg aag      96
Val Leu Ser Gln Leu Gln Leu Gln Glu Ser Gly Pro Gly Val Val Lys
         -1   1               5                  10 cct tcg gag acc ctg tcc ctc acc tgc gct gtc tct ggt ggc tct gtc     144
Pro Ser Glu Thr Leu Ser Leu Thr Cys Ala Val Ser Gly Gly Ser Val
         15                  20                  25 agc agt agt aac tgg tgg acc tgg atc cgc cag ccc cca ggg aag gga     192
Ser Ser Ser Asn Trp Trp Thr Trp Ile Arg Gln Pro Pro Gly Lys Gly
 30                  35                  40                  45 ctg gag tgg att gga cgt atc tct ggt agt ggt ggg gcc acc aac tac     240
Leu Glu Trp Ile Gly Arg Ile Ser Gly Ser Gly Gly Ala Thr Asn Tyr
                 50                  55                  60 aac ccg tcc ctc aag agt cga gtc atc att tca caa gac acg tcc aag     288
Asn Pro Ser Leu Lys Ser Arg Val Ile Ile Ser Gln Asp Thr Ser Lys
                 65                  70                  75 aac cag ttc tcc ctg aac ctg aac tct gtg acc gcc gcg gac acg gcc     336
Asn Gln Phe Ser Leu Asn Leu Asn Ser Val Thr Ala Ala Asp Thr Ala
             80                  85                  90 gtg tat tac tgt gcc aga gat tgg gcc caa ata gct gga aca acg cta     384
Val Tyr Tyr Cys Ala Arg Asp Trp Ala Gln Ile Ala Gly Thr Thr Leu
         95                 100                 105
```

```
ggc ttc tgg ggc cag gga gtc ctg gtc acc gtc tcc tca          423
Gly Phe Trp Gly Gln Gly Val Leu Val Thr Val Ser Ser
110             115                 120
```

<210> 4
<211> 141
<212> PRT
<213> Artifical Sequence

<220>
<223> Description of Artificial Sequence: Mature peptide is derived from Old World Monkey (macaque); leader sequence is an artificial sequence to facilitate cloning

<400> 4

```
Met Lys His Leu Trp Phe Phe Leu Leu Leu Val Ala Ala Pro Arg Trp
            -15             -10                 -5

Val Leu Ser Gln Leu Gln Leu Gln Glu Ser Gly Pro Gly Val Val Lys
        -1  1               5                   10

Pro Ser Glu Thr Leu Ser Leu Thr Cys Ala Val Ser Gly Gly Ser Val
    15                  20                  25

Ser Ser Ser Asn Trp Trp Thr Trp Ile Arg Gln Pro Pro Gly Lys Gly
30              35                  40                      45

Leu Glu Trp Ile Gly Arg Ile Ser Gly Ser Gly Gly Ala Thr Asn Tyr
                50              55                  60

Asn Pro Ser Leu Lys Ser Arg Val Ile Ile Ser Gln Asp Thr Ser Lys
            65                  70                  75

Asn Gln Phe Ser Leu Asn Leu Asn Ser Val Thr Ala Ala Asp Thr Ala
        80                  85                  90

Val Tyr Tyr Cys Ala Arg Asp Trp Ala Gln Ile Ala Gly Thr Thr Leu
    95                  100                 105

Gly Phe Trp Gly Gln Gly Val Leu Val Thr Val Ser Ser
110             115                 120
```

<210> 5
<211> 387
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(66)
<223> leader sequence

<220>

<221> mat_peptide
<222> (67)..(387)

<220>
<221> CDS
<222> (1)..(387)

<400> 5

| | | | | | | | | | | | | | | | | |
|---|---|---|---|---|---|---|---|---|---|---|---|---|---|---|---|---|
| atg | gac | atg | agg | gtc | ccc | gct | cag | ctc | ctg | ggg | ctc | ctt | ctg | ctc | tgg | 48 |
| Met | Asp | Met | Arg | Val | Pro | Ala | Gln | Leu | Leu | Gly | Leu | Leu | Leu | Leu | Trp | |
| | | -20 | | | | | -15 | | | | -10 | | | | | |

| ctc | cca | ggt | gcc | aga | tgt | gac | atc | cag | atg | acc | cag | tct | cca | tct | tcc | 96 |
|---|---|---|---|---|---|---|---|---|---|---|---|---|---|---|---|---|
| Leu | Pro | Gly | Ala | Arg | Cys | Asp | Ile | Gln | Met | Thr | Gln | Ser | Pro | Ser | Ser | |
| | -5 | | | | -1 | 1 | | | 5 | | | | | | 10 | |

| ctg | tct | gca | tct | gta | ggg | gac | aga | gtc | acc | atc | act | tgc | agg | gca | agt | 144 |
|---|---|---|---|---|---|---|---|---|---|---|---|---|---|---|---|---|
| Leu | Ser | Ala | Ser | Val | Gly | Asp | Arg | Val | Thr | Ile | Thr | Cys | Arg | Ala | Ser | |
| | | | | | 15 | | | | 20 | | | | | 25 | | |

| cag | gac | att | agg | tat | tat | tta | aat | tgg | tat | cag | cag | aaa | cca | gga | aaa | 192 |
|---|---|---|---|---|---|---|---|---|---|---|---|---|---|---|---|---|
| Gln | Asp | Ile | Arg | Tyr | Tyr | Leu | Asn | Trp | Tyr | Gln | Gln | Lys | Pro | Gly | Lys | |
| | | | 30 | | | | | 35 | | | | | 40 | | | |

| gct | cct | aag | ctc | ctg | atc | tat | gtt | gca | tcc | agt | ttg | caa | agt | ggg | gtc | 240 |
|---|---|---|---|---|---|---|---|---|---|---|---|---|---|---|---|---|
| Ala | Pro | Lys | Leu | Leu | Ile | Tyr | Val | Ala | Ser | Ser | Leu | Gln | Ser | Gly | Val | |
| | | 45 | | | | | 50 | | | | | 55 | | | | |

| cca | tca | agg | ttc | agc | ggc | agt | gga | tct | ggg | aca | gag | ttc | act | ctc | acc | 288 |
|---|---|---|---|---|---|---|---|---|---|---|---|---|---|---|---|---|
| Pro | Ser | Arg | Phe | Ser | Gly | Ser | Gly | Ser | Gly | Thr | Glu | Phe | Thr | Leu | Thr | |
| | 60 | | | | | 65 | | | | | 70 | | | | | |

| gtc | agc | agc | ctg | cag | cct | gaa | gat | ttt | gcg | act | tat | tac | tgt | cta | cag | 336 |
|---|---|---|---|---|---|---|---|---|---|---|---|---|---|---|---|---|
| Val | Ser | Ser | Leu | Gln | Pro | Glu | Asp | Phe | Ala | Thr | Tyr | Tyr | Cys | Leu | Gln | |
| 75 | | | | 80 | | | | 85 | | | | | | 90 | | |

| gtt | tat | agt | acc | cct | cgg | acg | ttc | ggc | caa | ggg | acc | aag | gtg | gaa | atc | 384 |
|---|---|---|---|---|---|---|---|---|---|---|---|---|---|---|---|---|
| Val | Tyr | Ser | Thr | Pro | Arg | Thr | Phe | Gly | Gln | Gly | Thr | Lys | Val | Glu | Ile | |
| | | | 95 | | | | | 100 | | | | | 105 | | | | aaa 387
Lys

<210> 6
<211> 129
<212> PRT
<213> Artifical Sequence

<220>
<223> Description of Artificial Sequence: Mature peptide is derived from Old World Monkey (macaque); leader sequence is an artificial sequence to facilitate cloning

<400> 6

Met Asp Met Arg Val Pro Ala Gln Leu Leu Gly Leu Leu Leu Leu Trp
        -20             -15                 -10

Leu Pro Gly Ala Arg Cys Asp Ile Gln Met Thr Gln Ser Pro Ser Ser

```
            -5                  -1    1              5                       10
    Leu Ser Ala Ser Val Gly Asp Arg Val Thr Ile Thr Cys Arg Ala Ser
                    15                  20                  25

Gln Asp Ile Arg Tyr Tyr Leu Asn Trp Tyr Gln Gln Lys Pro Gly Lys
                    30                  35                  40

Ala Pro Lys Leu Leu Ile Tyr Val Ala Ser Ser Leu Gln Ser Gly Val
                    45                  50                  55

Pro Ser Arg Phe Ser Gly Ser Gly Ser Gly Thr Glu Phe Thr Leu Thr
            60                  65                  70

Val Ser Ser Leu Gln Pro Glu Asp Phe Ala Thr Tyr Tyr Cys Leu Gln
    75                  80                  85                  90

Val Tyr Ser Thr Pro Arg Thr Phe Gly Gln Gly Thr Lys Val Glu Ile
                    95                  100                 105

Lys
```

<210> 7
<211> 411
<212> DNA
<213> Artifical Sequence

<220>
<223> Description of Artificial Sequence: Mature peptide is derived from Old World Monkey (macaque); leader sequence is an artificial sequence to facilitate cloning <220>
<221> misc_feature
<222> (1)..(57)
<223> leader sequence <220>
<221> mat_peptide
<222> (58)..(411)

<220>
<221> CDS
<222> (1)..(411)

<400> 7

```
atg gag ttt ggg ctg agc tgg gtt ttc ctt gtt cct ctt ttg aaa ggt    48
Met Glu Phe Gly Leu Ser Trp Val Phe Leu Val Pro Leu Leu Lys Gly
            -15                 -10                 -5 gtc cag tgt gag gtg cag ctg gtg gag tct ggg ggc ggc ttg gca aag    96
Val Gln Cys Glu Val Gln Leu Val Glu Ser Gly Gly Gly Leu Ala Lys
        -1  1               5                   10 cct ggg ggg tcc ctg aga ctc tcc tgc gca gcc tcc ggg ttc agg ttc   144
Pro Gly Gly Ser Leu Arg Leu Ser Cys Ala Ala Ser Gly Phe Arg Phe
        15                  20                  25
```

```
acc ttc aat aac tac tac atg gac tgg gtc cgc cag gct cca ggg cag    192
Thr Phe Asn Asn Tyr Tyr Met Asp Trp Val Arg Gln Ala Pro Gly Gln
 30              35                  40                  45 ggg ctg gag tgg gtc tca cgt att agt agt agt ggt gat ccc aca tgg    240
Gly Leu Glu Trp Val Ser Arg Ile Ser Ser Ser Gly Asp Pro Thr Trp
             50                  55                  60 tac gca gac tcc gtg aag ggc aga ttc acc atc tcc aga gag aac gcc    288
Tyr Ala Asp Ser Val Lys Gly Arg Phe Thr Ile Ser Arg Glu Asn Ala
                 65                  70                  75 aac aac aca ctg ttt ctt caa atg aac agc ctg aga gct gag gac acg    336
Asn Asn Thr Leu Phe Leu Gln Met Asn Ser Leu Arg Ala Glu Asp Thr
             80                  85                  90 gct gtc tat tac tgt gcg agc ttg act aca ggg tct gac tcc tgg ggc    384
Ala Val Tyr Tyr Cys Ala Ser Leu Thr Thr Gly Ser Asp Ser Trp Gly
         95                 100                 105 cag gga gtc ctg gtc acc gtc tcc tca                                411
Gln Gly Val Leu Val Thr Val Ser Ser
110             115
```

<210> 8
<211> 137
<212> PRT
<213> Artifical Sequence

<220>
<223> Description of Artificial Sequence: Mature peptide is derived from Old World Monkey (macaque); leader sequence is an artificial sequence to facilitate cloning

<400> 8

```
Met Glu Phe Gly Leu Ser Trp Val Phe Leu Val Pro Leu Leu Lys Gly
                -15                 -10                  -5

Val Gln Cys Glu Val Gln Leu Val Glu Ser Gly Gly

Gln Gly Val Leu Val Thr Val Ser Ser
110                 115

<210> 9
<211> 41
<212> DNA
<213> Artificial Sequence

<220>
<223> Description of Artificial Sequence: Primer

<400> 9
atcacagatc tctcaccatg gacatgaggg tccccgctca g          41

<210> 10
<211> 35
<212> DNA
<213> Artificial Sequence

<220>
<223> Description of Artificial Sequence: Primer

<400> 10
atcacagatc tctcaccatg aggctccctg ctcag                 35

<210> 11
<211> 35
<212> DNA
<213> Artificial Sequence

<220>
<223> Description of Artificial Sequence: Primer

<400> 11
atcacagatc tctcaccatg gaarccccag ckcag                 35

<210> 12
<211> 38
<212> DNA
<213> Artificial Sequence

<220>
<223> Description of Artificial Sequence: Primer

<400> 12
atcacagatc tctcaccatg gtgttgcaga cccaggtc              38

<210> 13
<211> 32
<212> DNA
<213> Artificial Sequence

<220>
<223> Description of Artificial Sequence: Primer

<400> 13
ggtgcagcca ccgtagcttt gatytccasc tt                               32

<210> 14
<211> 34
<212> DNA
<213> Artificial Sequence

<220>
<223> Description of Artificial Sequence: Primer

<400> 14
atcacagatc tctcaccatg rcctgstccc ctct                             34

<210> 15
<211> 34
<212> DNA
<213> Artificial Sequence

<220>
<223> Description of Artificial Sequence: Primer

<400> 15
atcacagatc tctcaccatg gcctggrctc ygct                             34

<210> 16
<211> 35
<212> DNA
<213> Artificial Sequence

<220>
<223> Description of Artificial Sequence: Primer

<400> 16
atcacagatc tctcaccatg gcmtggaycc ctctc                            35

<210> 17
<211> 21
<212> DNA
<213> Artificial Sequence

<220>
<223> Description of Artificial Sequence: Primer

<400> 17
cttgggctga cctaggacgg t                                           21

<210> 18
<211> 30

```
<212> DNA
<213> Artificial Sequence

<220>
<223> Description of Artificial Sequence: Primer

<400> 18
gcgactaagt cgaccatgga ctggacctgg                              30

<210> 19
<211> 30
<212> DNA
<213> Artificial Sequence

<220>
<223> Description of Artificial Sequence: Primer

<400> 19
gcgactaagt cgaccatgaa acacctgtgg                              30

<210> 20
<211> 33
<212> DNA
<213> Artificial Sequence

<220>
<223> Description of Artificial Sequence: Primer

<400> 20
gcgactaagt cgaccatgga gtttgggctg agc                          33

<210> 21
<211> 33
<212> DNA
<213> Artificial Sequence

<220>
<223> Description of Artificial Sequence: Primer

<400> 21
gcgactaagt cgaccatggg gtcaaccgcc atc                          33

<210> 22
<211> 33
<212> DNA
<213> Artificial Sequence

<220>
<223> Description of Artificial Sequence: Primer

<400> 22
gcgactaagt cgaccatgtc tgtctccttc ctc                          33
```

<210> 23
<211> 46
<212> DNA
<213> Artificial Sequence

<220>
<223> Description of Artificial Sequence: Primer

<400> 23
gccaggggga agaccgatgg gcccttggtg ctagctgagg agacgg      46

<210> 24
<211> 31
<212> DNA
<213> Artificial Sequence

<220>
<223> Description of Artificial Sequence: Primer

<400> 24
gatgggccct tggtgctagc tgaggagacg g      31

<210> 25
<211> 51
<212> DNA
<213> Artificial Sequence

<220>
<223> Description of Artificial Sequence: Primer

<400> 25
ggtgctagct gaggagacgg tgaccaggac tccctggccc cagaagccta g      51

<210> 26
<211> 17
<212> DNA
<213> Artificial Sequence

<220>
<223> Description of Artificial Sequence: Primer

<400> 26
atttaggtga cactata      17

<210> 27
<211> 16
<212> DNA
<213> Artificial Sequence

<220>
<223> Description of Artificial Sequence: Primer

```
<400> 27
gttttcccag tcacga                                                    16

<210> 28
<211> 20
<212> DNA
<213> Artificial Sequence

<220>
<223> Description of Artificial Sequence: Primer

<400> 28
atatacgact cactataggg                                                20

<210> 29
<211> 24
<212> DNA
<213> Artificial Sequence

<220>
<223> Description of Artificial Sequence: Primer

<400> 29
ccgtcagatc gcctggagac gcca                                           24

<210> 30
<211> 20
<212> DNA
<213> Artificial Sequence

<220>
<223> Description of Artificial Sequence: Primer

<400> 30
gcagttccag atttcaactg                                                20

<210> 31
<211> 21
<212> DNA
<213> Artificial Sequence

<220>
<223> Description of Artificial Sequence: Primer

<400> 31
ccaggccact gtcacggctt c                                              21

<210> 32
<211> 20
<212> DNA
```

```
<213> Artificial Sequence
<220>
<223> Description of Artificial Sequence: Primer

<400> 32
cagagctggg tacgtcctca                                          20

<210> 33
<211> 20
<212> DNA
<213> Artificial Sequence

<220>
<223> Description of Artificial Sequence: Primer

<400> 33
gcccccagag gtgctcttgg                                          20

<210> 34
<211> 20
<212> DNA
<213> Artificial Sequence

<220>
<223> Description of Artificial Sequence: Primer

<400> 34
acacagaccc gtcgacatgg                                          20

<210> 35
<211> 20
<212> DNA
<213> Artificial Sequence

<220>
<223> Description of Artificial Sequence: Primer

<400> 35
gctctcggag gtgctcctgg                                          20

<210> 36
<211> 30
<212> DNA
<213> Artificial Sequence

<220>
<223> Description of Artificial Sequence: Primer

<400> 36
acagacccgt cgaccatgga gtttgggctg                               30
```

```
<210> 37
<211> 27
<212> DNA
<213> Artificial Sequence

<220>
<223> Description of Artificial Sequence: Primer

<400> 37
ccccttggtg ctagctgagg agacggt                                    27

<210> 38
<211> 27
<212> DNA
<213> Artificial Sequence

<220>
<223> Description of Artificial Sequence: Primer

<400> 38
agagagaacg ccaagaacac actgttt                                    27

<210> 39
<211> 27
<212> DNA
<213> Artificial Sequence

<220>
<223> Description of Artificial Sequence: Primer

<400> 39
aaacagtgtg ttcttggcgt tctctct                                    27
```

UNITED STATES PATENT AND TRADEMARK OFFICE
CERTIFICATE OF CORRECTION

PATENT NO.        : 6,893,636 B2                                   Page 1 of 1
APPLICATION NO.   : 09/019441
DATED             : May 17, 2005
INVENTOR(S)       : Mitchell E. Reff et al.

It is certified that error appears in the above-identified patent and that said Letters Patent is hereby corrected as shown below:

Col. 27, line 64
replace "6G5"
with --5E8--.

Claim 13
replace "8"
with --7--.

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,893,636 B2 | Page 1 of 1 |
| APPLICATION NO. | : 09/019441 | |
| DATED | : May 17, 2005 | |
| INVENTOR(S) | : Mitchell E. Reff et al. | |

It is certified that error appears in the above-identified patent and that said Letters Patent is hereby corrected as shown below:

Col. 27, line 64
replace "6G5"
with --5E8--.

Col. 67, Claim 13, line 4
replace "8"
with --7--.

This certificate supersedes the Certificate of Correction issued December 23, 2008.

Signed and Sealed this

Twenty-seventh Day of January, 2009

JOHN DOLL
*Acting Director of the United States Patent and Trademark Office*